US006992759B2

(12) United States Patent
Nakayama et al.

(10) Patent No.: US 6,992,759 B2
(45) Date of Patent: Jan. 31, 2006

(54) SAMPLE HOLDER FOR SPECTRUM MEASUREMENT AND SPECTROPHOTOMETER

(75) Inventors: Kin-ichi Nakayama, Ibo-gun (JP); Shingo Kataoka, Ibaraki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 188 days.

(21) Appl. No.: 10/683,116

(22) Filed: Oct. 14, 2003

(65) Prior Publication Data

US 2004/0233423 A1 Nov. 25, 2004

(30) Foreign Application Priority Data

Oct. 21, 2002 (JP) ............................ 2002-306057

(51) Int. Cl.
*G01N 21/01* (2006.01)

(52) U.S. Cl. ...................... 356/244; 356/301; 356/246; 356/440; 250/339.07

(58) Field of Classification Search ................ 356/244, 356/246, 440, 319, 323, 325, 326, 328; 250/339.07
See application file for complete search history.

(56) References Cited

U.S. PATENT DOCUMENTS

| | | | | |
|---|---|---|---|---|
| 4,090,789 A * | 5/1978 | Macemon et al. | .......... | 356/318 |
| 4,609,991 A * | 9/1986 | Minton et al. | ................ | 702/25 |
| 5,338,935 A * | 8/1994 | Truett et al. | ........... | 250/339.08 |

FOREIGN PATENT DOCUMENTS

| | | |
|---|---|---|
| JP | 01-170843 | 7/1989 |
| JP | 06-242005 | 9/1994 |
| JP | 11-304689 | 11/1999 |

OTHER PUBLICATIONS

Maruzen, "Chemical experiment lecture 6, Spectroscopy 1, 4th Edition", The Chemical Society of Japan,Jul. 25, 1991, pp. 230-237.

"Near infrared spectroscopy, Measurement Series 32," Japan Society of Spectroscopy, Academy Publication Center, 1st edition, May 20, 1996, 2nd edition, Nov. 30, 1998, pp. 148-156.

* cited by examiner

*Primary Examiner*—F. L. Evans
(74) *Attorney, Agent, or Firm*—Connolly, Bove, Lodge & Hutz, LLP

(57) ABSTRACT

The present invention is a sample holder for spectrum measurement settable in a measuring chamber of a spectrophotometer and being used for measuring a spectrum of a liquid sample, which comprises a holding block (11) having a hole (111) and a light introducing path (112) being provided crosswise, and a light introducing path position adjusting means (12) being located under the holding block (11), said the light introducing path position adjusting means (12) comprising a light introducing path horizontal direction position adjusting means (12-1) and/or a light introducing path vertical direction position adjusting means (12-2), for adjusting so as to the irradiation light is introduced into the liquid sample by aligning a position of the light introducing path (112) with a propagating route of the irradiation light for spectrum measurement, said the holding block (11) further comprising a device for controlling a temperature of said liquid sample.

28 Claims, 32 Drawing Sheets

(a)

(b)

(a)

(b)

(c)

(a)

(b)

Data of measurment on uv curing of MMA (a)

(b)

(a)

(b)

SAMPLE HOLDER FOR SPECTRUM MEASUREMENT AND SPECTROPHOTOMETER

TECHNICAL FIELD

The present invention relates to a sample holder which holds a sample upon analysis of the molecular structure of the sample by irradiating the sample with light of specific wavelength and obtaining the absorption spectrum, and to a spectrophotometer using said sample holder, and more specifically, it relates to the sample holder and the spectrophotometer which can be used, for example, for measuring near infrared and infrared absorption spectrum or a Raman spectrum of the sample in the process of the chemical reaction, and which enables the position adjustment and the temperature adjustment.

BACKGROUND ART

When various light is irradiated at a substance, an absorption spectrum, a scattered light spectrum and the like are obtained. Conventionally, the spectrum analysis method which measures and utilizes the absorption spectrum, the scattered spectrum, and the like is put in practical use in order to analyze the molecular structure of the substance.

For example, when an infrared ray is emitted to a certain molecule and the wavelength thereof is varied continuously, the infrared ray of the same frequency as the natural frequency of the molecule is absorbed, and a near infrared and infrared absorption spectra (it is sometimes referred to as an infrared spectrum hereafter) corresponding to the molecular structure are obtained. Thus, a method in which the infrared spectrum obtained by emitting an infrared ray to a sample is measured in order to analyze the molecular structure thereof is called infrared absorption spectrum analysis method.

Moreover, when light is emitted to a substance, a strong elastic scattering light which has the same frequency as that of the incident light, and a very weak inelastic scattering light which has the frequency slightly deviated from the frequency of the incident light are scattered. Among these, the Raman scattered light, which is scattered by the vibrating atom and ion in the substrate, is included in the inelastic scattering light. Thus, a method in which a spectrum of the Raman scattered light (it is sometimes referred to as a Raman spectrum hereafter) obtained by irradiating light (especially laser beam) to a sample is measured in order to analyze the molecular structure thereof is called Raman absorption spectrum analysis method.

In these spectrum analysis methods, a substance to be analyzed is prepared as a sample for measurement; the measurement of the spectrum by emitting light to the sample is generally carried out in the condition of atmospheric pressure and room temperature (in ordinary temperature and ordinary pressure condition).

Specifically, a technique which measures an infrared spectrum while heating a sample, such as the heating diffuse reflection method, that is one of the infrared absorption spectrum methods, is known (for example, "Chemical experiment lecture 6. Spectroscopy 1.4th Edition", the Chemical Society of Japan, Maruzen, published on July 25, Heisei 3 (1991), pp. 230–237, etc.).

According to this reference, an infrared spectrophotometer called diffuse reflectance spectroscopy (DRS) is used, and a powdered material obtained by mixing a substance (solid) to be measured and potassium bromide (KBr) in an equal amount is used as a sample in the heating diffuse reflection method. Infrared light is emitted to the powdered sample, reflection and refraction (transmission) are repeated while varying the depth of penetration, and thereby diffuse reflection phenomenon in which the infrared light is reflected in various directions take place; and the infrared spectrum is measured efficiently by making use of this phenomenon.

Further, in this reference, it is described that, although the measurement in a condition of ordinary temperature and ordinary pressure conditions is common for the heating diffuse reflection method, an infrared spectrum is sometimes measured in a vacuum and heating condition in order to make use in analysis of a compound absorbed on a surface of a catalyst, in the case of infrared spectrum measurement in the field of the catalyst, and that, in such case, a vacuum heating type measurement cell different from an ordinary measurement cell is used in the spectrum measurement chamber of DRS. However, for this method, the target of measurement described in the reference is solid and there is no description how to practically apply heat to a liquid sample. Additionally, what described in the reference is a configuration equipped to the fixed and specific apparatus and there is no description of a contrivance which can be applied to various spectrophotometers by allowing adjust the position of a sample holder to various directions, so as to measure more precise spectrum.

Furthermore, a technology which is called as near infrared optical fiber analysis method in reaction and process controls and in which light is brought from a spectrometer to the site of the sample by means of an appropriate optical fiber, a transmission or reflection light by the sample is brought back to the spectrometer and measurement is carried out. (For example, "Near infrared spectroscopy," Measurement Series 32 by Japan Society of Spectroscopy, ed. by Y. Ozaki, S. Kawada, et al., published by Academy Publication Center, 1st edition, May 20, 1996, 2nd edition, Nov. 30, 1998, pp. 148–156, etc.)

Although a sample is placed in a sample chamber of a spectrometer and the spectrum is measured for the ordinary spectrometric analysis method, FIG. 4.3.13 in page 150 in this reference describes a method in which light is brought from a spectrometer to the site of the sample by appropriate optical fiber, a transmission or reflection light from the sample is returned to the spectrometer and measurement is carried out and in which a reaction solution is lead from a reaction container cooled with water to the cell through a quartz bypass. Although there is described a method which tracks a polymerization reaction of methyl methacrylate (MMA) while cooled with water, description about the spectrum measurement with heating, the possibility of heating or specific apparatus or structure for heating is not shown. Moreover, the measurement method described in the publication relates to the technique in which light is brought from a spectrometer to the site of the sample by the optical fiber, a transmission or reflection light from the sample is returned to the spectrometer and measurement is carried out; however, a description which specifically suggests a sample holder for spectrum measurement which can be installed in a measurement chamber of the various spectrophotometer and which comprises longitudinal hole for holding a liquid sample, a mechanism controlling the temperature of the liquid sample and a position adjusting means which is to move the position of the holder to be adjusted to the light path of spectrum is not found.

Japanese Patent Publication Hei-01-170843 (pages 1 and 4–6) discloses a thermal analysis/microspectrometry and an apparatus therefor carrying out the thermal analysis and spectrum measurement simultaneously by an optical microscope, which comprises placing a sample on a stage of the microscope, irradiating an infrared ray to reach to the sample from a light source of an infrared spectrophotometer, irradiating an infrared ray transmitted the sample to reach to the infrared spectrophotometer through object lens and aperture of the microscope, detecting light intensity of specific wavelength by the infrared spectrophotometer while varying the temperature of the sample, and measuring an infrared spectrum of the micro-region of the sample at the temperature when light intensity of the specific wavelength changes abruptly or at the temperature before and after that.

The apparatus disclosed in Japanese Patent Publication Hei-01-170843 is common to the present invention in that this apparatus analyzes a molecular structure relation through changes of the spectrum condition of the functional group of the sample by heating the sample; however, this apparatus is one to observe changes in physical properties upon heating of the sample in solid state by the microscope. Specifically, this apparatus is one which macroscopically analyzes phase changes of the sample with changing the temperature of the sample placed on the stage of the microscope and carries out the microscopic observation and infrared spectrum observation simultaneously to thereby captures changes in chemical structure or changes of spatial distribution in micro-scale. However, the object of measurement in the present invention is a liquid sample so that the object of measurement originally differs from that of the reference. The technology disclosed in the reference is the attachment for the microscopic apparatus and has no relation with the present invention. There is no description suggesting the possibility that the similar technology can be applied to the spectrophotometer as disclosed in the present invention.

Japanese Patent Publication Hei-06-242005 (pages 1 and 3) discloses a measuring apparatus which is provided with an internal reflection element penetrated disposed in the center of a container which is a cell or the like, and in which curable resin is held into a cell chamber having windows in front of and behind the internal reflection element and the resin is cured while emitting ultraviolet ray or the like from the window, and, simultaneously, infrared ray is irradiated from a part of the internal reflection element and infrared spectrophotometric absorbance spread by total-reflecting in the internal reflection element is measured. This technology relates to the apparatus which detects the reaction proceeding state of the resin attaching to the internal reflection element by measuring the reflection spectrum from the surface of the internal reflection element of the infrared spectrum.

The technology disclosed in Japanese Kokai Publication Hei-6-242005 is not a technology for spectrum measurement under the condition in which the temperature of a liquid sample is controlled, but it is one of special equipments for observing behavior of curing reaction of the curable resin be attaching to the internal reflection element, in which curing is initiated by heating or by ultraviolet by irradiating infrared spectrum of internal resin to the internal reflection element. The internal reflection element is specifically a prism, and into the cell chamber capable of being inserted with the prism, liquid resin sample is held into the cell and cured, and curing state is observed. However, in order to precisely observe the curing state of the resin by measuring the spectrum, the sensitivity is not enough with this measurement apparatus.

In Japanese Kokai Publication Hei-6-242005, since it only discloses the technology to introduce the light for spectrum measurement to the inside of the liquid resin sample by using the prism, a position adjusting means which can adjust the position of an introducing path of the measuring light in order to apply to the various spectrum measuring equipment is not disclosed or the necessity thereof is not disclosed. A holding block configuration for adjusting the temperature of the liquid sample is not disclosed neither. Therefore, it is a different technology from the present invention.

As the whole, the technology disclosed in Japanese Kokai Publication Hei-6-242005 is one of methods to measure the curing behavior of the resin by the infrared ray and is a method to measure an infrared spectrum by introducing the infrared ray to the internal of the liquid sample by using the prism. This technology is a different technology from the present invention, which is an object of the present invention, regarding a holding block provided with a temperature controlling device for the liquid sample and a holding block provided with a position adjusting means to be used in an ordinary spectrum measurement equipment such as transmission IR, surface reflection IR, Raman scattering spectrum or the like.

Furthermore, in Japanese Patent Publication Hei-11-304689, it is disclosed a sample holder which comprises a sample holding plane being distributed with multiple number of micro-groove for holding a solid sample and which allows to provide a diffused/reflected light necessary for the measurement from the sample within the sample holding plane. In this technology, the usage of a metal file and the like as the solid sample holding plane of the sample holder is disclosed and it is described that incident light upon the sample holding plane, is detected as a diffused/reflected light from the sample in the plurality of micro-grooves, and the condition of the sample on the metal file is solid such as powder or a very small member. However, there is no description about a member on which a liquid sample is applied to thereby measuring transmission and/or reflection of the sample. Moreover, no reference is available which specifically discloses a sample holder for spectrum measurement for measuring the condition of the liquid sample altered by irradiating a light other than a light for spectrum measurement.

SUMMARY OF THE INVENTION

In conventional methods of spectrum analysis, as mentioned above, the technology of measuring the spectrum while heating a solid sample and the technology of measuring the solution at ordinary temperature by using an optical fiber are known among the heating diffuse reflection method, but in case that the target is a liquid sample, almost no technology of measuring the spectrum in the reaction state while heating the liquid sample is known. Besides, almost nothing has been known about a technology of measuring the spectrum at very low temperature. Moreover, configurations disclosed are those to be installed directly to the spectrum measurement apparatus, but not those provided with a position adjusting means in various directions for being applied to various spectrum measurement apparatus.

Liquid samples include, for example, curable compositions having unsaturated double bond (for example, unsaturated polyester resin, vinyl ester resin, polymerizable monomer having unsaturated double bond) and the like. They are thermopolymerizable or photopolymerizable also, but it is required to observe the polymerization reaction behavior or curing reaction behavior induced by light, aside from observation of polymerization reaction behavior or curing reaction behavior upon heating. Recently, in particular, the development of photocurable composition for color filter of high precision, or of curing compositions by electron beams aside from light has been actively conducted, and for the purpose of fundamental development of these compositions, there is a mounting need for easy and accurate observation of polymerization reaction behavior or curing reaction behavior inducted by light or electron beams. At the same time, there is an increasing need for real-time analysis of such behavior. These photopolymerizable compositions are cured also by high energy beams such as gamma-rays and laser beam, and application thereof into semiconductor element substrate of high precision is also studied widely, which give rise to necessity of real-time analysis technique of curing behavior of these photocurable resins by high energy beams.

For example, in synthesis of various organic compounds and polymers, liquid phase conditions are widely employed to execute synthesis by adding material compounds or monomers to various solvents. In synthesis of novel compound or polymer, it is very important to analyze the process of the synthesis, but in the process of synthesis in such liquid phase, it is substantially difficult to measure the near infrared or infrared spectrum or Raman spectrum with the lapse of time. In particular, it is difficult to obtain precise spectrum information by monitoring the polymerization of polymer or synthesis status of the composition in low temperature state or under heating. Further, other reaction than the polymerization may possibly occur during polymerization reaction, which may sometimes be monitored. Moreover, aside from the synthesis reaction behavior of various organic compounds or polymerization behavior of polymers by heat, it is required to observe the changes of synthesis reaction or polymerization behavior of various organic compounds and polymers by irradiation with light or electron beams.

Basically, in the conventional spectrophotometers, as mentioned above, although it is assumed to measure the spectrum from the sample in ordinary temperature and ordinary pressure condition, it is not assumed to use the spectrophotometer by applying heat to the liquid sample in stable state. Besides, depending on the heating temperature of the sample, heat may be also applied to the spectrophotometer, and in such application as to measure the spectrum while heating the liquid sample, there was a possibility of having an adverse effect on the spectrophotometer which is a precision instrument. Moreover, the temperature of the liquid sample may increase in the case of ultraviolet irradiation to the sample, and it is difficult to observe spectrum change of the liquid sample precisely under ultraviolet irradiation while maintaining the temperature of the sample to a certain stable condition.

In order to measure the near infrared and infrared spectrum exactly in the time course of synthesis process in liquid phase, the scale of measurement becomes small. Therefore, it is required to adjust the position and the condition of the irradiation light to the sample delicately, and a problem may occur to impede accurate measurement of spectrum. Similarly, fine adjustment is also needed for irradiation light other than the irradiation light for spectrum measurement used in irradiation of liquid sample with light or electron beams.

This invention is devised in the solution of the above-mentioned problems, and it is hence an object thereof to provide a sample holder for spectrophotometer capable of measuring the spectrum accurately while controlling (specifically, heating or cooling) the temperature of a liquid sample in stable condition or, a sample holder can be applied to in-situ reaction monitoring, and also to provide a spectrophotometer using such sample holder.

This invention also provides a method of measuring the polymerization behavior or reaction behavior of photopolymerizable or photoreactive compound by irradiating UV or electron beam or the like by using the sample holder for spectrophotometer specified in this invention and the spectrophotometer using the same sample holder. The invention further provides a technology for developing or investigating the photopolymerizable or photoreactive compounds by measuring the polymerization behavior or reaction behavior of photopolymerizable or photoreactive compound irradiated by UV or electron beam or the like, by using the above sample holder and the spectrophotometer using the above sample holder.

Specifically, the present invention is a sample holder for spectrum measurement settable in a measuring chamber of a spectrophotometer and being used for measuring a spectrum of a liquid sample, said measuring chamber being provided in a way of an irradiation light being emitted from a light irradiating means 21 to a light detecting means 22 for spectrum measurement, which comprises a holding block 11 having a hole 111 and a light introducing path 112 being provided crosswise, said the hole 111 being for holding a sample container 30 filled with the liquid sample, said the light introducing path 112 being for introducing the irradiation light for spectrum measurement into the liquid sample held by said hole 111, said the irradiation light for spectrum measurement being emitted from the light irradiating means 21 toward the liquid sample held by the hole 111 by passing through the light introducing path 112 and reaching to the light detecting means 22 of the spectrophotometer, a light introducing path position adjusting means 12 being located under the holding block 11, said the light introducing path position adjusting means 12 comprising a light introducing path horizontal direction position adjusting means 12-1 and/or a light introducing path vertical direction position adjusting means 12-2, for adjusting so as to the irradiation light is introduced into the liquid sample by aligning a position of the light introducing path 112 with a propagating route of the irradiation light for spectrum measurement, when the sample holder for spectrum measurement is set in the measuring chamber of the spectrophotometer, said the light introducing path vertical direction position adjusting means 12-2 adjusting the position of the light introducing path 112 in a vertical direction relative to the propagating route of the irradiation light for spectrum measurement, said the holding block 11 further comprising a device for controlling a temperature of said liquid sample.

The present invention is a spectrum measuring method which comprises setting the above sample holder for spectrum measurement in a spectrophotometer, adjusting the light introducing path 112 to the optical path by moving the light introducing path 112 in order to match light detecting sensitivity of the spectrophotometer by means of the light introducing path horizontal direction position adjusting means 12-1 and/or the light introducing path vertical direction position adjusting means 12-2, introducing the irradiation light for spectrum measurement into the liquid sample controlled with temperature, and measuring the spectrum of the liquid sample by detecting the irradiation light for spectrum measurement by means of the light detecting means 22, said irradiation light for spectrum measurement being originated from the light irradiating means 21 and reaching to the light detecting means 22 of the spectrophotometer.

The present invention is a spectrophotometer which comprises the above sample holder for spectrum measurement.

BRIEF DESCRIPTION OF THE DRAWINGS

FIG. 35(*a*) shows a configuration in which the part above the light introducing path position adjusting means 12 can be rotated. FIG. 35(*b*) shows a configuration in which a part above the insulating means 13 can be rotated.

DESCRIPTION OF REFERENCE NUMERALS

-continued

Figure 1:
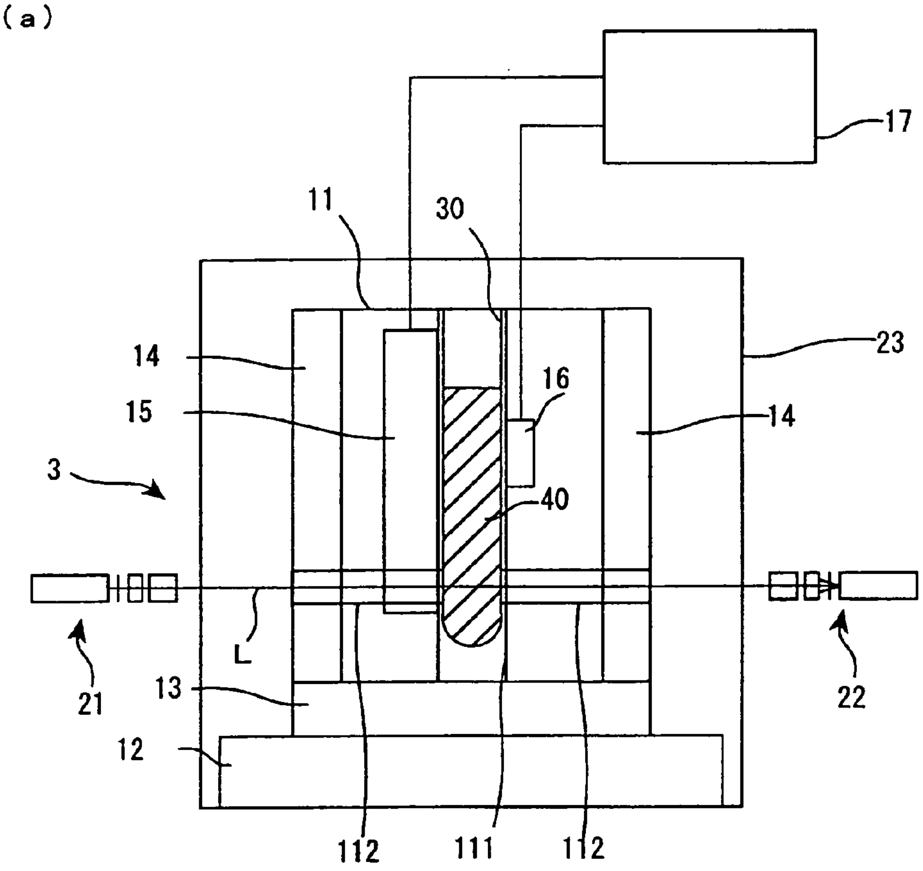
FIG. 1(*a*) is a schematic diagram showing an example of configuration of sample holder 3 in an embodiment of the invention, and (b) is a perspective view showing an example of configuration of holding block 11 of the sample holder 3 of (a). The configuration of FIG. 1(*b*) includes a second temperature sensor in order to measure the temperature in the vicinity of the sample more precisely.
Figure 1:
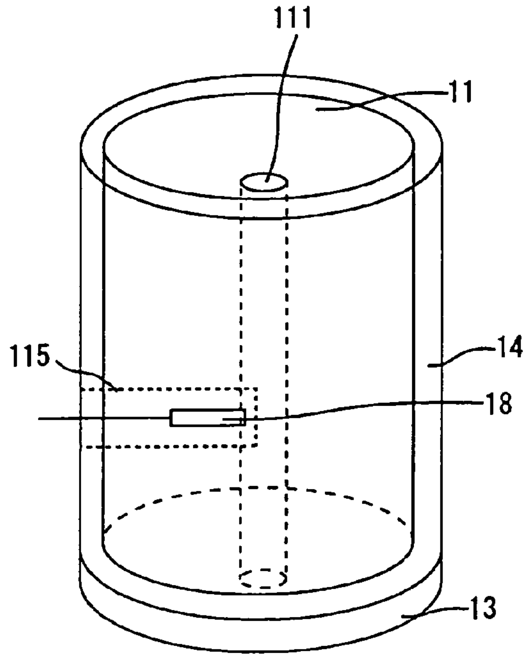

| DESCRIPTION OF REFERENCE NUMERALS | |
|---|---|
| 3 | Sample holder (sample holder for spectrum measurement) |
| 6 | Ray or electron beam irradiating device of a ray other than the light for spectrum measurement |
| 11 | Holding block |
| 12 | Light introducing path position adjusting means |
| 13 | Lower insulating unit (insulating means) |
| 14 | Insulating cover (insulating means) |
| 15 | Heater (heating means) |
| 16 | Temperature sensor |
| 17 | Temperature controller |
| 18 | Second temperature sensor |
| 21 | Light irradiating unit (light irradiating means) |
| 22 | Light detecting unit (light detecting means) |
| 23 | Measuring chamber |
| 30 | Sample container of liquid sample |
| 40 | Liquid sample |
| 41 | Agitating device |
| 42 | Nitrogen blow piping for rotating sample container |
| 50 | Refrigerant |
| 51 | Apparatus for circulating refrigerant |
| 53 | Piping |
| 55 | Liquid nitrogen circulating device |
| 60 | Cooling water circulating device |
| 61, 63, 64, 65 | Joint |
| 66 | Bolt (central axis) |
| 67 | Screw |
| 68 | Head of a bolt |
| 69 | Screw nut |
| 70 | Washer |
| 71 | Optical fiber light sensor |
| 72 | Laser beam irradiating device for Raman measurement |
| 73 | Raman scattering light detecting apparatus |
| 74 | Raman light introducing port |
| 81 | Sample container holding hole for Raman measurement |
| 82 | Sample container for Raman measurement |
| 83 | Sample container holding hole for Raman measurement |
| 84 | Sample container for Raman measurement |
| 85 | Infrared sample container |
| 86 | Thin film holder component |
| 87 | Diamond cell |
| 88 | Sample for Raman measurement |
| 100 | Rotating means (turntable) |
| 111 | Sample holding hole |
| 112 | Light introducing path |
| 113 | Heater hole |
| 114 | Lower part of the holding block (cross shape) |
| 115 | Temperature measuring side hole |
| 116 | Ray introducing path of other ray than the light for spectrum measurement |
| 120 | Installation fixing stage |
| 121 | X-direction moving stage |
| 122 | Y-direction moving stage |
| 123 | X-direction operation unit |
| 124 | Y-direction operation unit |
| 125 | X-direction position fixing screw |
| 126 | Y-direction position fixing screw |
| 127 | Z-direction operation unit |
| 128 | Z-direction position fixing screw |
| 129 | Z-direction moving stage |
| 200 | Position operation unit of light holding means |
| 201 | Light holding means |
| 202 | Position fixing screw of light holding means |
| 400 | Z-direction |
| B | Direction of irradiation light for spectrum measurement from light irradiating unit of spectrometer |
| L | Propagating route of irradiation light for spectrum measurement |
| L' | Propagating route of laser beam for Raman measurement |
| M | Propagating direction of the ray other than the light for spectrum measurement |
| R | Rotating direction of holding block rotating means |
| S | Raman scattering light |

DETAILED DESCRIPTION OF THE INVENTION

The invention is specifically described below.

The sample holder for spectrum measurement of the invention is a sample holder for spectrum measurement which can be installed in a measuring chamber of a spectrophotometer, and which comprises a fixing means of a liquid sample, a means for introducing an irradiation light for spectrum measurement emitted from a light irradiating means of the spectrophotometer to the liquid sample, a device for controlling a temperature of the liquid sample, and further a means for moving the position of a light introducing path in a horizontal direction and/or a vertical direction so as to introduce the irradiation light for spectrum measurement into the liquid sample (herein after, also referred to as a light introducing path position adjusting means).

The above device for controlling the temperature of the liquid sample may be any means which can control the temperature of the liquid sample stably, and preferably a device comprising a means for heating or cooling and a means for measuring the temperature. Such a device includes a heating device for heating the liquid sample and a cooling device for cooling the liquid sample, in which one of them or both of them may be used. The cooling device for cooling the liquid sample is preferably an apparatus 51 for introducing and circulating a refrigerant 50 in the holding block 11 for keeping the liquid sample at low temperature of 10° C. or less.

Although the sample holder for spectrum measurement of the present invention comprises the device for controlling the temperature of the liquid sample, it may be used at an ordinary temperature without controlling the temperature of the liquid sample while measurement.

The sample holder 3 for spectrum measurement of the invention is a sample holder 3 for spectrum measurement which can be installed in a measuring chamber of a spectrophotometer, and which comprises a holding block 11 having a hole 111 for holding a liquid sample and a light introducing path 112 for introducing the irradiation light for spectrum measurement emitted from light irradiating means 21 and to be reached to a light detecting means 22 of the spectrophotometer into the liquid sample held in the hole 111 being provided crosswise, and a light introducing path horizontal direction position adjusting means 12-1 and/or a light introducing path vertical direction position adjusting means 12-2, as a light introducing path position adjusting means 12, for adjusting so as to the irradiation light is introduced into the liquid sample by aligning a position of the light introducing path 112 with a propagating route of the irradiation light for spectrum measurement in case the sample holder for spectrum measurement is installed in the measuring chamber of the spectrophotometer, and in which the holding block 11 has a heating device 15 for heating the liquid sample, as the device for controlling the temperature of the liquid sample.

The sample holder 31 for spectrum measurement of the invention is a sample holder 31 for spectrum measurement which can be installed in a measuring chamber of a spectrophotometer, and which comprises a holding block 11 having a hole 111 for holding a liquid sample and a light introducing path 112 for introducing the irradiation light for spectrum measurement emitted from light irradiating means 21 and to be reached to a light detecting means 22 of the spectrophotometer into the liquid sample held in the hole 111 being provided crosswise, and a light introducing path horizontal direction position adjusting means 12-1 and/or a light introducing path vertical direction position adjusting means 12-2, as a light introducing path position adjusting means 12, for adjusting so as to the irradiation light is introduced into the liquid sample by aligning a position of the light introducing path 112 with a propagating route of the irradiation light for spectrum measurement in case the sample holder for spectrum measurement is installed in the measuring chamber of the spectrophotometer, and in which the holding block 11 has an apparatus 51 for introducing and circulating a refrigerant 50 in the holding block 11 so as to keep the liquid sample at low temperature of 10° C. or less, as the device for controlling the temperature of the liquid sample.

The above hole 111 may be any insertion hole for holding a sample container 30 of the liquid sample, which can hold the liquid sample and has no problem for the spectrum measurement, and may be provided in any direction of longitudinal, lateral or oblique, however, a longitudinal hole of a hole shape is preferred. The above longitudinal hole is preferable to have a configuration provided from the upper plane of the holding block toward the lower part of the holding block in a longitudinal direction.

The position to provide the light introducing path 112 is not specified as long as it is parallel to the propagating route of the irradiation light for spectrum measurement and the irradiation light can enter the light introducing path 112, and it may be provided at the upper part of the holding block or the lower part of the holding block.

Figure 32:
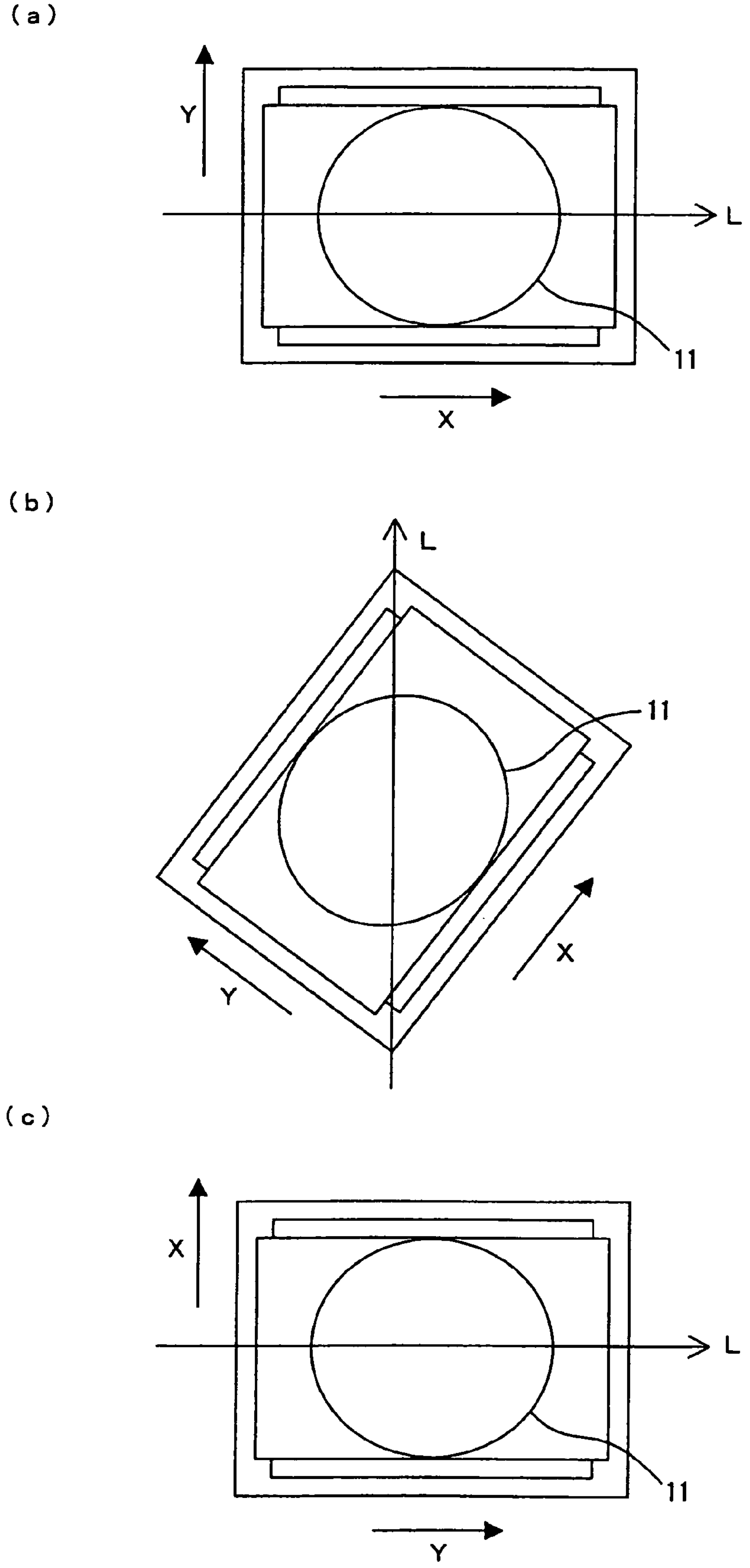
FIG. 32 is a diagram showing an example of the X-direction and Y-direction and the propagating route of the irradiation light for spectrum measurement.

Moreover, regarding the sample holder for spectrum measurement, it is preferable that the light introducing path horizontal direction position adjusting means 12-1 for adjusting the position so as to be introduced into the liquid sample is to adjust the position in an X-direction and in a Y-direction orthogonal to the X-direction, and the light introducing path vertical direction position adjusting means 12-2 provided as required is to adjust the position in a Z-direction perpendicular to the X-direction and Y-direction, a plane including the X-direction and a plane including the Y-direction being on the same plane or parallel. The above X-direction exists on the same plane as the plane including the propagating route of the irradiation light for spectrum measurement or on a plane parallel to the plane including the above propagating route. The above Y-direction is perpendicular to the X-direction and exists on the same plane as the plane including the propagating route of the irradiation light for spectrum measurement or on a plane parallel to the plane including the above propagating route. In FIG. 32, a configuration of the X-direction and Y-direction and the propagating route L of the irradiation light for spectrum measurement is shown; however, it is not limitative of the present invention. The preferable configuration of the present invention is a configuration in which the X-direction is along with the propagating route of the irradiation light for spectrum measurement as shown in FIG. 32(*a*); however, a configuration in which the X-direction is not parallel the propagating route of the irradiation light for spectrum measurement as shown in FIGS. 32(*b*) and (*c*) may be feasible.

According to the above structure, by means of the light introducing path position adjusting means, the relative position of the light introducing path to the propagating route of the irradiation light can be changed so that the irradiation light emitted from the light irradiating means can be securely introduced into the sample. Therefore, from the liquid sample of which temperature is stably controlled in heated state or in cooled state, the spectrum can be detected instantly and in the time course in more proper manner. As a result, the spectrum can be measured, in particular, in the process of synthesis of various organic compounds and polymers while maintaining the heating state or the low temperature state of 10° C. or less. On the basis of those results, hence, re-evaluation of the developing technique and the calculation of the composition suited for the purpose in case that, for example, the high curing or reactive property is required can be realized. If the purpose is not obtaining high curing or reactive property, by using the measuring apparatus having the sample holder for spectrum measurement of the invention, the composition suited for the purpose can be assessed easily. When the holder is provided with an apparatus which can circulate the refrigerant for measuring the liquid sample in a very-low-temperature condition, a precise spectrum analysis of the reaction mechanism and polymerization reaction mechanism under a very-low-temperature condition can be carried out.

The sample holder for spectrum measurement is preferably provided with an insulating means between the holding block 11 of the sample holder for spectrum measurement and the light introducing path position adjusting means 12. The above insulating means is preferably a lower insulating means to be provided under the holding block. Further, the sample holder is preferably provided with an insulating cover outside of the holding block.

According to the above structure, the transfer of heat of the holding block 11 to the light introducing path position adjusting means or to the spectrophotometer is suppressed or prevented. Hence, adverse effects are not caused on the precision instruments such as light introducing path position adjusting means or the spectrophotometer. Similarly, by the above insulating means, it is possible to suppress or prevent the transmission of heat to the irradiating means of the light or electron beam irradiated from the irradiating means of the light or electron beam other than that for spectrum measurement or the vicinity of the optical fiber sensor light at its leading end. In case that the device for controlling the temperature of the liquid sample is in a configuration of keeping the holding block 11 at low temperature by circulating the refrigerant, it is preferred to have the heat insulating means because dew condensation is prevented where necessary.

The insulating means is also important for protecting the precision instruments from heat when tracing the state changes for a long period when measuring the polymerization state of photopolymerizable compound, in particular.

Preferably, the sample holder for spectrum measurement of the invention is provided externally with an irradiating means 6 for irradiating at least one species of ray or electron beam selected from the group consisting of electron beam, gamma-ray, laser beam, X-ray, ultraviolet ray, visible ray, and far infrared ray as the irradiating means 6 of the ray or electron beam other than the ray for spectrum measurement, at a position where the ray other than the light for spectrum measurement is to be introduced into the liquid sample, and further provided with a ray introducing path 116 for introducing the ray emitted from the irradiating means 6 aside from the light introducing path 112 for introducing the irradiation light for spectrum measurement into the liquid sample, and is to be used for measuring, by means of spectrum, a state of the liquid sample being changed by the ray irradiated from the irradiating means 6.

The irradiating means 6 of the ray or electron beam other than the light for spectrum measurement is preferred to be an ultraviolet ray irradiating means.

In this configuration, the ultraviolet ray irradiating means, for example, is provided as the irradiating means of the ray or electron be a mother than the light for spectrum measurement, and the ultraviolet ray irradiating means is disposed at a position that the ultra violet ray irradiated from the ultraviolet ray irradiating means is to be introduced into the sample, and therefore the change behavior, reaction behavior and polymerization behavior of the liquid sample due to the ultraviolet ray can be observed by the spectrum.

The ray irradiated by the irradiating means 6 of the light or electron beam other than that for spectrum measurement includes electron beam, gamma-ray, laser beam, X-ray, ultraviolet ray (UV), visible ray, and far infrared ray, excluding the light for spectrum measurement (infrared, near infrared, Raman ray). Such ray may also include electromagnetic waves such microwave, radio wave, audio frequency, and electron beam (EB). The above ray is preferred to have a wavelength range of $10^{-16}$ to $10^{-6}$ cm, and electromagnetic waves are preferred to have a wavelength range of $10^{-1}$ to $10^{10}$ cm. More preferably, the ray is an ultraviolet ray. In this specification, the light or electron beam other than the light for spectrum measurement is sometimes described as the ray, for convenience.

The irradiating means 6 of the ray or electron beam other than the light for spectrum measurement can be the hitherto known irradiating means and can be selected appropriately according to the species of the ray or electron beam.

The sample holder for spectrum measurement of the invention preferably has a configuration which is applied to an equipment that uses a liquid sample obtained by blending a specified amount of photopolymerization initiator to a compound having an unsaturated double bond represented by photocurable resin or photocurable monomer, and aims to observe the extinction or change behavior of the unsaturated double bond such as vinyl group from the spectrum by irradiating such liquid sample with the light mentioned above. In the case of a high energy beam, blending of photopolymerization initiator may not be required in some cases. The compound having an unsaturated double bond represented by photocurable resin or photocurable monomer is excited to light if blended with photo acid initiator, too, and can induce chemical changes. Therefore, depending on the type and purpose of the liquid sample, the liquid sample for the above measuring apparatus can be prepared also by blending a photo acid initiator.

The light for spectrum measurement preferably includes a transmission light, a reflected diffusion light or a scattering light. More preferably, it is a transmission light or a scattering light.

The transmission light is preferred to be an infrared or near infrared spectrum. Infrared spectrum is more preferable. The scattering light is preferred to be a Raman spectrum.

The Raman spectrum is included in laser beam and has higher wavelength energy than that of the infrared light. The infrared spectrum measurement method is a method to detect a specific wavelength absorbed by the specific molecular structure in the sample irradiated. When Raman light (laser beam), which has a higher energy than infrared light, is irradiated to the substance, a strong elastic scattering light having the same wavelength as the incident light and a weak inelastic scattering light having a slightly different wavelength from that of the incident light are scattered. The inelastic scattering light includes a Raman scattering light scattered by atoms or ions vibrating in the sample. The method which measures such Raman scattering light is called the Raman spectrum measuring method. In carrying out the Raman spectrum measuring method, it is required to focalize to the specified irradiating position (the position of the sample) and, it has been difficult to sufficiently carry out the measurement with controlling the temperature of the sample in the conventional Raman spectrophotometer. However, since the sample holder for spectrum measurement of the present invention is provided with the light introducing path position adjusting means, it is possible to precisely focus on the Raman irradiating position, as in the same manner as to adjust the position of the light introducing path for infrared spectrum measurement, whereby it is possible to measure reaction behavior and the like with the lapse of time while heating or cooling the liquid sample when Raman light is used as the light for spectrum measurement.

The liquid sample may be prepared by diluting, if necessary, with a solvent not polymerizing or reacting with the light, such as methyl isobutyl ketone or toluene. Usually, the amount of the photopolymerization initiator is appropriately selected in a range of 0.1 to 5 parts by weight in 100 parts by weight of the compound having an unsaturated double bond responding to the light of wavelength of $10^{-16}$ to $10^{-6}$ cm, represented by photocurable resin or photocurable monomer. The blending amount of photo acid initiator is also a known amount. According to the kind of the light to be irradiated, the compound having an unsaturated double bond itself may be excited. There is also a case that the photopolymerization initiator formulated in the liquid sample generates a radical and the radical acts on the compound having an unsaturated double bond.

When the light introducing path position adjusting means which changes the relative position of the light introducing path 112 relative to the propagating route of the irradiation light for spectrum measurement to thereby align the position to the propagating route of the irradiation light is in such structure which has a light introducing path position adjusting means that can change the position of the light introducing path at least in one direction of the X-direction and Y-direction perpendicular to the X-direction, and the Z-direction vertical to the X-direction and Y-direction, it becomes easy to adjust the strongest light of the spectrum to be used for detecting the state of the liquid sample being varied by the ray other than spectrum or electromagnetic wave to the light introducing path. As a result, the spectrum can be measured more stably.

The light introducing path position adjusting means preferably included in the sample holder for spectrum measurement of the invention is more specifically described by referring to an example of infrared spectrum among other spectra. The infrared spectrum radiates several beams of light, and while observing the strongest light by detecting the value of the interferogram of the infrared light device, the optical axis of the strongest infrared spectrum is adjusted to the light introducing path 112 of the in-situ infrared spectrum measurement attachment (sample holder for infrared spectrum measurement) provided with the light introducing path position adjusting means by means of the light introducing path position adjusting means. More preferably, the optical axis of the strongest infrared spectrum coincides to the center of the light introducing path 112. By moving so that the center of the optical path coincides to the center of the light introducing path 112, precision of the spectrum measurement is improved and the comparison of the spectra under approximately the same condition is possible while using different analytical apparatus. As a result, the sample holder of the invention can be applied not only to the qualitative analysis but also to the quantitative analysis. By adjusting the position to obtain the maximum interferogram intensity, the position of the light introducing path 112 and the position of the spectrum light can be adjusted to approximately to the same position so that a convenient, easy and stable measurement is enabled. Also, the reproducibility is obtained easily.

The sample holder for spectrum measurement of the invention is often detached and attached, or installed in an apparatus by other manufacturer owing to its role as an attachment for a spectrophotometer. In such a case, if the light introducing path of the attachment (sample holder) is deviated from the center of the optical axis of the above infrared spectrum, it is required to adjust the optical axis of the strongest infrared spectrum to the center of the light introducing path of the infrared spectrum measurement attachment (sample holder for infrared spectrum measurement). It is an advantage that such adjustment is easy by using the light introducing path position adjusting means. In particular, the change state of liquid sample changed from time to time by other ray than the light for spectrum measurement or electromagnetic wave such as the photocuring state or photopolymerization state is faster in change than curing or polymerization by general heat, and the light introducing path position adjusting means is an effective technique for more accurate measurement of the spectrum.

According to the above configuration, since the device for controlling the temperature of the liquid sample, specifically a device for heating or cooling, is provided together with the irradiating means 6 of at least one species of ray or electron beam selected from electron beam, gamma-ray, laser beam, X-ray, ultraviolet ray, visible ray, and far infrared ray, the liquid sample can be heated or cooled according to the irradiation of the liquid sample by at least one species of ray selected from electron beam, gamma-ray, laser beam, X-ray, ultraviolet ray, visible ray, and far infrared ray, so that the spectrum can be measured in more diversified conditions. Thus, spectrum measurements of the liquid sample of which temperature is precisely controlled under various conditions can be realized. As a result, analysis of the photopolymerizable composition, measurement of physical properties, development of that composition, process control during production and the like can be efficiently carried out by the configuration of the present invention.

The spectrophotometer of the invention comprises the above sample holder for spectrum measurement. The above spectrophotometer preferably comprises a light irradiating means, a light detecting means and a measuring chamber, and the sample holder for spectrum measurement is preferably disposed in the measuring chamber.

Preferred embodiments of the sample holder for spectrum measurement of the invention are described below while referring to FIG. 1 to FIG. 37. It must be noted, however, that the invention is not limited to these embodiments alone.

Regarding the sample holder 3 for spectrum measurement or the sample holder 31 for spectrum measurement (hereinafter, both of them are referred as the sample holder for spectrum measurement without distinguishing each other) of the invention, a structural example of the holding block 11 and the light introducing path position adjusting means 12 (specifically, the light introducing path position adjusting means 12 includes the light introducing path horizontal direction position adjusting means 12-1 and/or the light introducing path vertical direction position adjusting means 12-2) is schematically shown in FIG. 1(*a*). Specifically, this is a sample holder comprising a holding block 11 in a columnar form and a light introducing path position adjusting means 12 provided beneath the holding block 11.

The sample holder for spectrum measurement in FIG. 1 comprises, aside from the holding block 11 and light introducing path position adjusting means 12, a lower insulating means 13 and an insulating cover 14 and, a heater 15 and a temperature sensor 16 as a device for controlling a temperature, as shown schematically in FIGS. 1(*a*) and (*b*). Of course, it may also comprise other structure or members.

Figure 4:
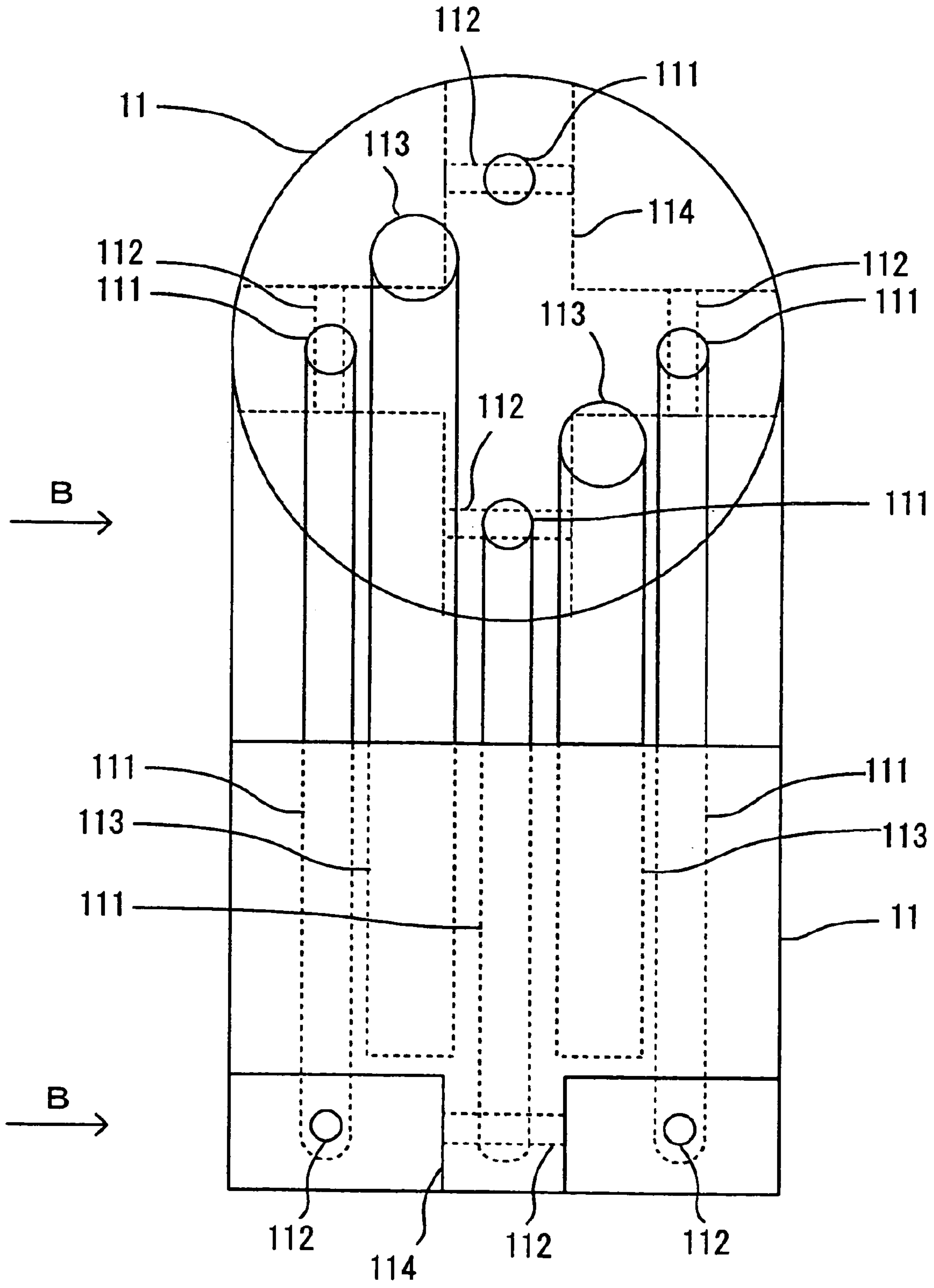
FIG. 4 is an elevation view from the above showing relation of sample holding hole 111 for holding a sample container 30 of a liquid sample and a hole 113 for the heater to be equipped with the heater as a heating device 15 in the holding block 11 in a top view, which is a plan view showing emission of a light for the spectrum measurement from spectrophotometer, and the bottom view is a side view of the holding block having the same structure.
Figure 5:
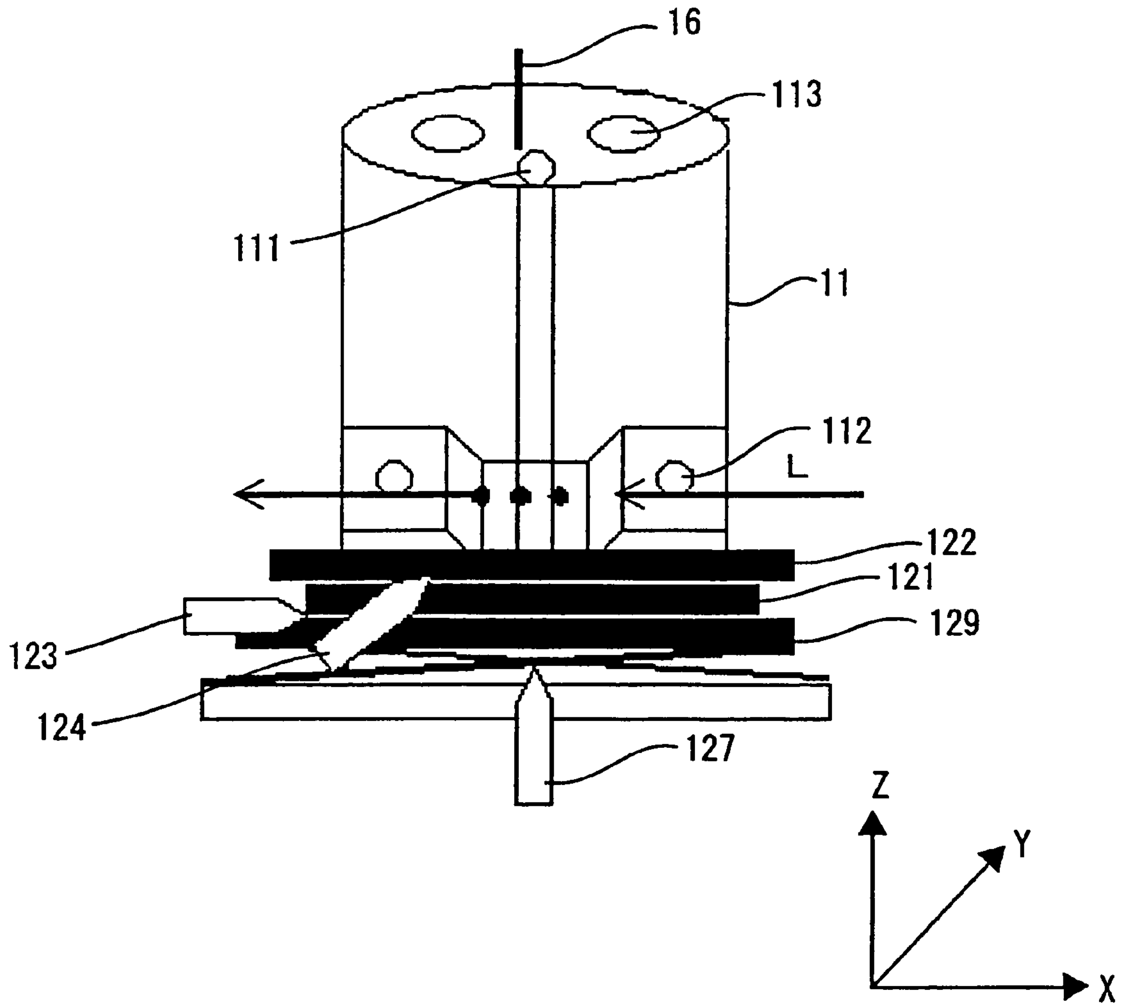
FIG. 5 is a diagram showing the relation of X-direction, Y-direction and Z-direction position adjusting means and moving stages. The right side is a schematic view showing the motion of the X-Y-Z axis.

The holding block 11 in FIG. 1 includes a hole 111 (referred as a sample holding hole 111, hereinafter) formed along the vertical direction, capable of holding a sample container (container for measurement) 30 filled with a liquid sample 40 stably in its inside, as well as a light introducing path 112 provided so as to cross almost orthogonal to the sample holding hole 111. The light introducing path 112 is preferably provided in the lower part of the holding block 11, however, the lower part of the holding block may be cut in columnar shape, or part of the columnar bottom may be cut out in a sector columnar shape as shown in FIG. 5. By cutting out part of the columnar bottom in a sector columnar shape, the weight of the entire holding block can be reduced. Specifically, as shown in FIG. 4, the bottom of the sample holding hole 111 is disposed at four positions in a cross as viewed from the above in the lower part of the holding block 11 so as to surround the central part of the circular columnar holding block 11. That is, the lower part is cut out to be a cross shape in a manner that a bottom of the hole 111 is held at the lower part of the holding block, and the light introducing paths 112 are provided at four positions so as to be nearly orthogonal to the sample holding hole 111. In FIG. 4, the light introducing path 112 is provided so as to be nearly vertical to the sample holding hole 111, however, the sample holding hole 111 and the light introducing path 112 maybe crossed in a manner that the spectrum measurement is carried out without problem.

As shown schematically in FIG. 1(*a*), the spectrophotometer in a preferred embodiment of the invention comprises at least a light irradiating means 21 and a light detecting means 22 disposed linearly and opposingly, and a measuring chamber 23 disposed so as to be enclosed by them, and the sample holder for spectrum measurement is disposed in the measuring chamber 23, in order to introduce a transmission spectrum into the liquid sample. In this configuration, as shown in FIG. 1(*a*), the light introducing path 112 provided in the sample holder for spectrum measurement is disposed at a position so as to coincide nearly with the propagating route L of the irradiation light, that is, the linear route until reaching the light detecting means 22 irradiated from the light irradiating means 21.

In order to dispose the light introducing path 112 provided in the sample holder for spectrum measurement at a position so as to coincide nearly with the linear route until reaching the light detecting means 22 irradiated from the light irradiating means 21, the sample holder for spectrum measurement having the holding block 11 of the invention further comprises the light introducing path horizontal direction position adjusting means 12-1 and/or the light introducing path vertical direction position adjusting means 12-2 for adjusting the position of the light introducing path of the holder in the vertical direction relative to the propagating route of the irradiation light. FIG. 1 does not show the light introducing path horizontal direction position adjusting means 12-1 or the light introducing path vertical direction position adjusting means 12-2. They are described in detail below.

In order that the irradiation light for spectrum measurement irradiated from the light irradiating means 21 may be guided into the liquid sample, a configuration in which the light introducing path horizontal direction position adjusting means 12-1 adjusts the position of the holding block in the X-direction and the Y-direction orthogonal to the X-direction, and the light introducing path vertical direction position adjusting means 12-2 adjusts the position in the Z-direction perpendicular to the X-direction and Y-direction is preferable.

Thus, the sample holder for spectrum measurement having the holding block 11 of the invention includes an X-direction operation unit 123 for moving the holding block 11 in the X-direction, a Y-direction operation unit 124 for moving in the Y-direction orthogonal to the X-direction, and a Z-direction operation unit 127 for moving in the Z-direction perpendicular to the X-direction and Y-direction, and therefore the light introducing path 112 provided in the holding block 11 can be disposed more accurately at a position nearly coinciding with the linear route of the light to reach the light detecting means 22 irradiated from the light irradiating means 21 of the spectrophotometer. If the manufacture of the spectrophotometer to be connected is different, the position can be adjusted easily. These operation units are not shown in FIG. 1. They are described below. The relation between the operation units and the stages on which the holding block is mounted is shown in FIG. 2, FIG. 3, FIG. 5, FIG. 6, FIG. 8, and FIG. 9.

Regarding the sample holder for spectrum measurement of the invention, it is preferred that the irradiation light for spectrum measurement being originated from the light irradiating means 21 and reaching to the light detecting means 22 reaches to the light detecting means 22 by transmitting or scattering the liquid sample after entering into the liquid sample.

In FIG. 1, the light irradiating means 21 and the light detecting means 22 of the spectrophotometer are disposed linearly and opposingly, but the position of the light detecting means 22 is not limited as far as the transmission light scattering light or the like from the liquid sample 40 can be detected by the light detecting means 22 securely and efficiently. Therefore, it may be changed properly depending on the spectrum to be used. When the light for spectrum measurement is an infrared spectrum, a configuration in which the light irradiating means 21 and the light detecting means 22 are disposed linearly and opposingly, and the irradiation light for spectrum measurement reaches to the light detecting means 22 by transmitting the liquid sample after entering into the liquid sample is preferable. The configuration in which the light irradiating means 21 and light detecting means 22 of the spectrophotometer are disposed linearly and opposingly is preferably employed when measuring the transmission type spectrum.

When the irradiation light for spectrum measurement is a Raman spectrum, a configuration in which the irradiation light for spectrum measurement is introduced into said liquid sample and then a scattering light irradiated from the liquid sample is detected by said light detecting means 22 is preferable. The above scattering light is preferred to be detected by the detecting means disposed vertically to the sample or at an angle of 90 degrees relative to the light introducing path of the irradiation light. A configuration in which the scattering light is detected by using an optical sensor as the light detecting means 22 provided with the light irradiating means, or detected by the light detecting means 22 provided at an angle of 90 degrees relative to the irradiation light irradiated from the light irradiating means 21 is more preferred.

Figure 33:
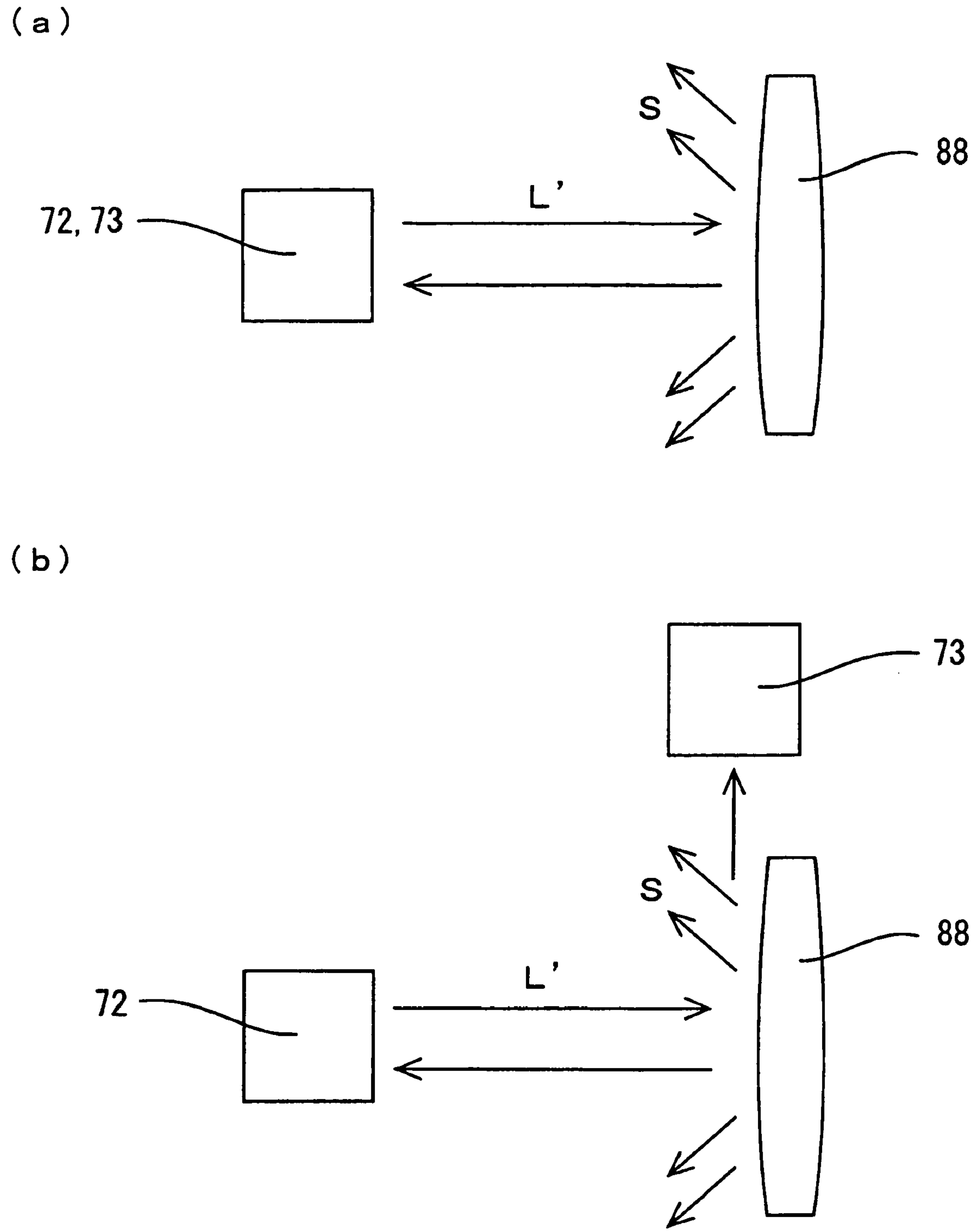
FIG. 33 shows the relation of a laser irradiating device, a Raman scattering light detecting device and a sample in a Raman spectrum analysis.
Figure 34:
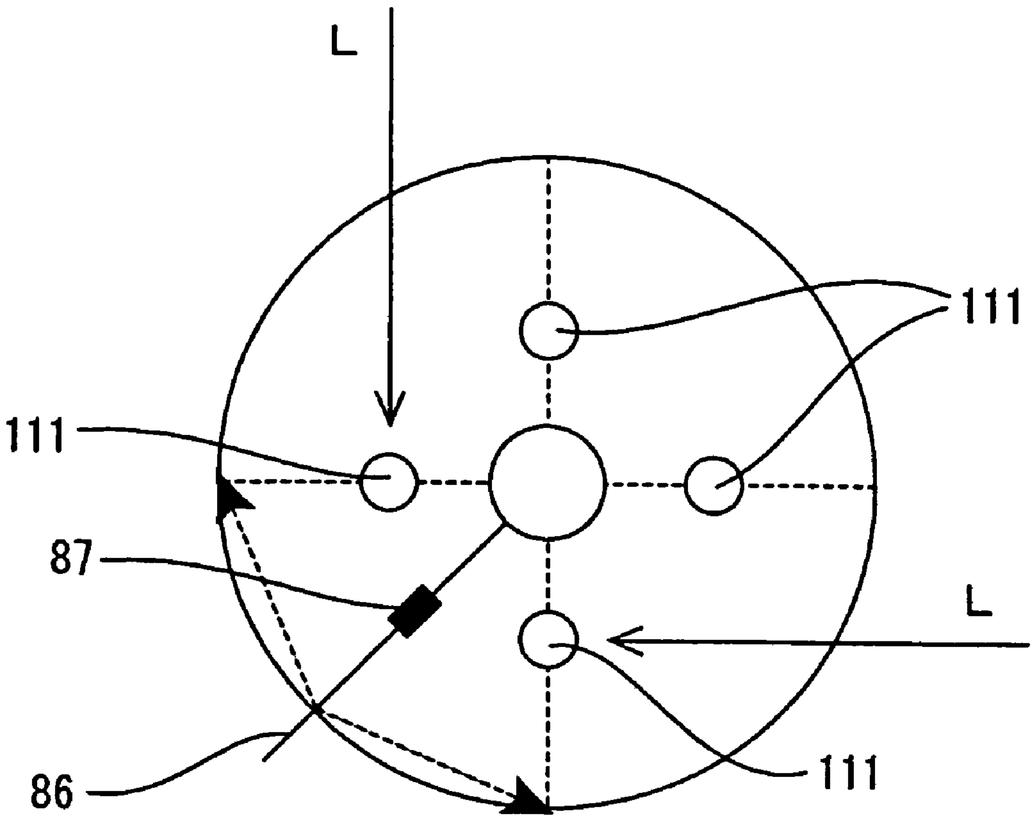
FIG. 34 is a schematic view showing the sample holder from the above in case that the thin film holder component is provided.

In FIG. 33, a preferable configuration of the relative position of a irradiating apparatus 72 irradiating the light for spectrum measurement (laser beam) to the sample for Raman measurement and a Raman scattering light detecting apparatus 73 is shown. FIG. 33(*a*) shows a preferable configuration in which the Raman scattering light is detected at a position perpendicular to the sample. In this configuration, it is preferred that the laser irradiating apparatus 72 and the Raman scattering light detecting apparatus 73 are provided concomitantly. FIG. 33(*b*) shows a preferable configuration in which the Raman scattering light is detected at a position of 90 degrees relative to the light introducing path of the irradiation light.

The holding block 11 is designed to heat or cool the liquid sample 40 in the sample container 30 by heating the entire piece by the heater 15, or, cooling the entire piece by the apparatus circulating the refrigerant while stably holding the liquid sample 40 (that is, the sample container 30 filled with liquid sample 40) stably in the sample holding hole 111. Therefore, the material of the holding block 11 is preferred to be high in heat conductivity. The holding block 11 is preferred to be formed of, for example, aluminum, copper or other metal, and more preferably an aluminum block made of aluminum. When the holding block 11 is an aluminum block, not only the thermal conductivity is high, but also the weight is light as compared with copper or the like, and it is easy to handle when mounting and dismounting the sample holder for spectrum measurement in the measuring chamber 23, hence it is preferable.

The shape of the holding block 11 is not particularly specified as far as the irradiation light from the light irradiating means 21 can be irradiated to the liquid sample 40 securely and efficiently, and the irradiation light from the liquid sample 40 can be detected securely and efficiently by the light detecting means 22. Specifically, the holding block is preferable to be circular columnar or polygonal columnar in a shape. In this embodiment, the holding block 11 having a cylindrical shape is preferably used as shown in FIG. 1(*b*), FIG. 4, FIG. 5, FIG. 9, FIG. 15 to FIG. 18, etc.

The holding block 11 is more specifically explained in FIG. 4. In FIG. 4, the sample holding holes 111 are formed at four positions in a cross form so as to surround the central part of the cylinder, and heater holes 113 for installing the heater 15 are formed at two positions so as to be positioned between two sample holding holes 111. The number, position or shape of the sample holding holes 111 and heater holes 113 are not limited as far as there is no adverse effect on the heating state of the holding block 11 or on low temperature state in the case of the holding block 11 having an apparatus for circulating a refrigerant, however, at least the sample holding holes 111 are preferred to be provided with two or more, and the position thereof is preferred to be at equal distance from the heater hole 113. Moreover, the holes 111 are preferably provided radially relative to the vertical center of the holding block as an axis at equal distance.

When the sample holding holes 111 are provided with two or more and are at equal distance from the heater hole 113, by measuring the actual sample for measuring the spectrum and reference sample (control) in the sample holding holes, the both samples can be heated and held under the same condition, hence is preferable.

When number of the hole 111 is too many, the propagating route of the irradiation light passing through the light introducing path 112 toward one of holes 111 is sometimes blocked by the portion where another hole 111 exists internally in the holding block, no matter when the holding block is circular columnar or polygonal columnar in a shape. The number of hole 111 is preferably six or less. When the number of the hole 111 is more than six, such problem may happen and it maybe difficult to hold the hole 111 in the holding block sufficiently and to control the temperature of the liquid sample thoroughly. FIG. 4 shows the configuration having four holes 111.

When the holding block 11 is a circular columnar in a shape, the heat from the heater 15 can be uniformly transmitted to the plurality of sample holding holes 111. It becomes also easy to dispose at equal distance from the center of the plurality of sample holding holes. As a result, only by rotating the holding block 11, the sample container 30 to be measured can be switched easily. For example, assuming the position indicated by arrow B in FIG. 4 to be the exit position (position corresponding to the propagating route L of the irradiation light) of the irradiation light from the light irradiating means 21, only by rotating the holding block 11, the sample container 30 held in the four sample holding holes 111 can be easily moved to the position of arrow B. Hence, more preferably, the holding block 11 of the invention is circular columnar in a shape, and the holding block 11 and light introducing path position adjusting means 12, specifically the bottom of the holding block 11, is provided with a holding block horizontal direction rotating means 80. The mechanism of the holding block rotating means 80 is not particularly specified as far as the holding block 11 can be rotated. For example, the rotating means may be disposed between the holding block 11 and the light introducing path position adjusting means 12. The holding block rotating means 80 is not shown in FIG. 1 and other figures.

As for more simple mechanism, it is preferable that the rotating means 80 is provided between the holding block and the light introducing path position adjusting means 12. By using this mechanism, the sample holding hole is not be changed in the relative position to the light introducing path when the samples are switched by rotating the holding block.

The rotating means 80 is preferably comprises a ratchet apparatus of a rotating means fixing apparatus in order to fix the holding block 11 at a specified position when adjusting the position of the sample holding hole 111 holding the next sample to the propagating route L of the irradiation light for spectrum measurement so as to the irradiation light is properly introduced. When provided with such a rotating means fixing apparatus, the rotating means 80 is prevented from rotating unexpectedly during measurement. The rotating means 80 is specifically a rotating means in horizontal direction.

Figure 35:
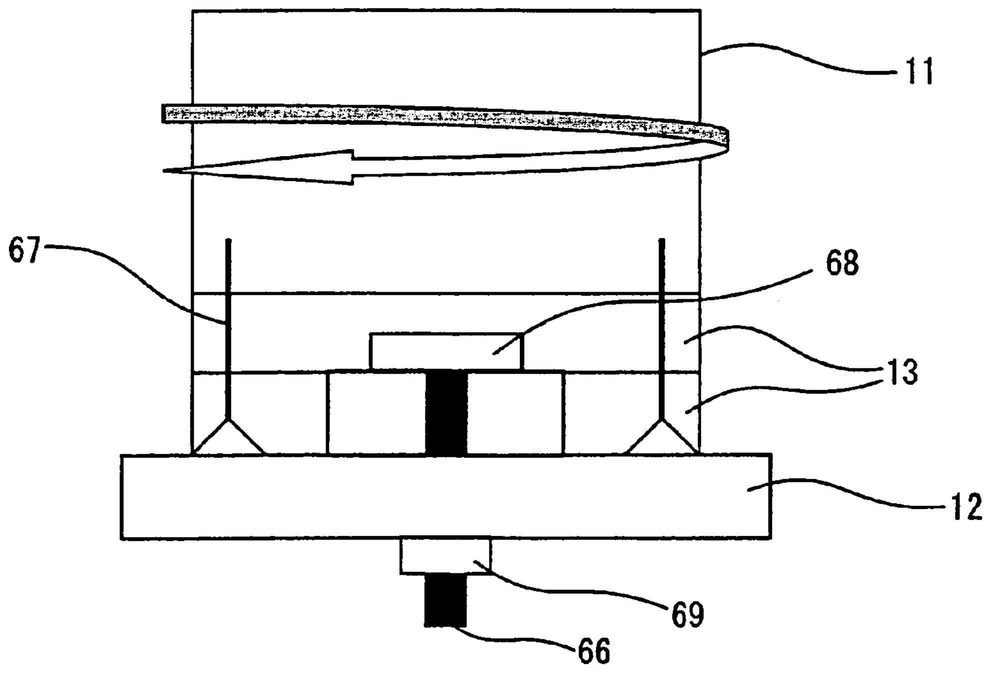
FIG. 35 is a diagram showing a preferable embodiment of the rotating means 80.
Figure 35:
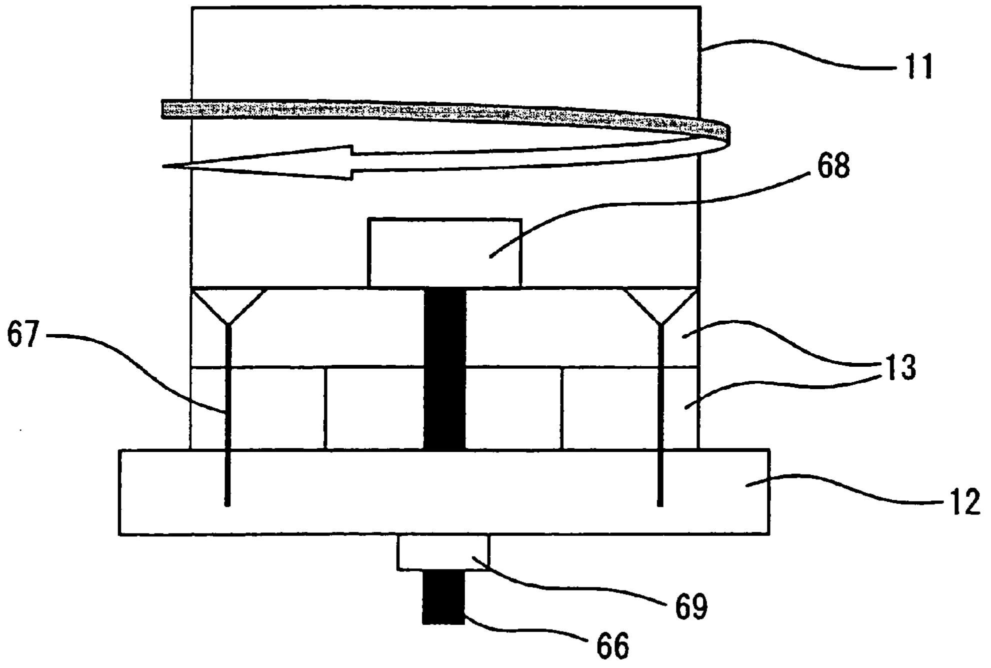

The rotating means 80 is not limited as far as it can rotate the holding block and, preferably, is a configuration which can rotate the holding block around the center thereof as an axis. The rotating means may be one rotating the holding block 11 fixed to the lower insulating means 13 together with the lower insulating means 13 on upper surface of the light introducing path position adjusting means 12 in a horizontal direction. Such configuration preferably includes, as shown in FIG. 35(*a*), a configuration which comprises the lower insulating means 13 and the holding block 11 being fixed together, and rotates the holding block 11 and the lower insulating means 13 together horizontally on an upper plane of the light introducing path position adjusting means 12, said lower insulating means 13 being provided to the light introducing path position adjusting means 12, by a bolt 66 and a screw nut 69, so as the bolt 66 to be a center of the lower insulating means 13 as an axis. The rotating means may be one rotating the holding block alone on upper surface of the lower insulating means around a head of a bolt as an axis in a condition that the lower insulating means 13 fixed to the light introducing path position adjusting means 12 in a manner that a central axis of the lower insulating means 13 is penetrated by the bolt. Such configuration includes, as shown in FIG. 35(*b*), a configuration which comprises the lower insulating means 13 and the light introducing position adjusting means 12 being fixed together in a manner that a center axis of the lower insulating means is penetrated by a bolt 66, and rotates the holding block 11 alone on an upper plane of the lower insulating means 13, a head of the bolt 66 being embed to the holding block 11 and supporting the holding block 11.

Figure 38:
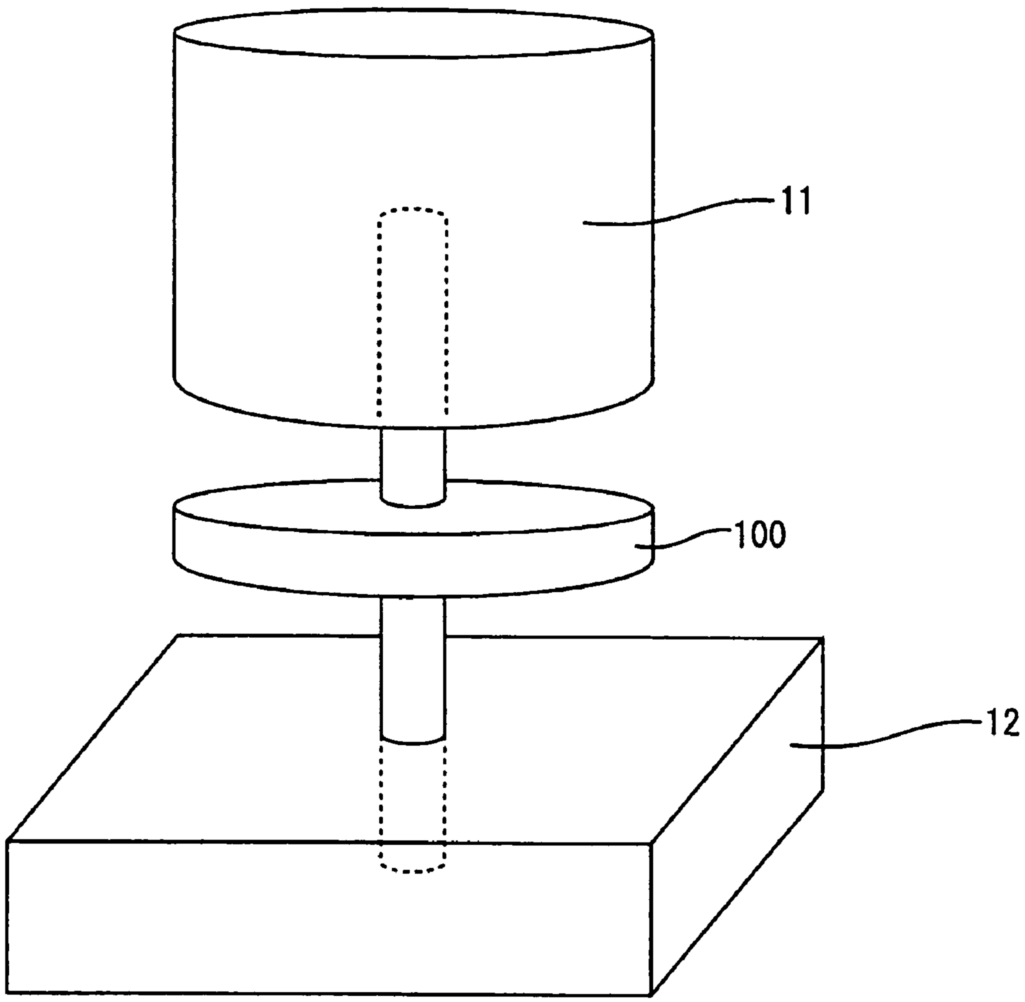
FIG. 38 is a schematic view showing a relative position of the central axis, the holding block 11, rotating means (turntable) 100 and light introducing path position adjusting means 12 in a preferred embodiment of the sample holder for spectrum measurement of the present invention. The table-shaped rotating means is provided between the holding block 11 and the light introducing position adjusting means 12, and the lower insulating means 13 (not shown) is provided on the top or at bottom of the rotating means.

The rotating means 80 may include a configuration in which a turntable 100 for holding block is placed at the bottom of the holding block 11, the holding block is held or fixed to the turntable by means of a bolt extended from a central part of the holding block and the turntable 100 is to be rotated. It may include a configuration in which a bolt extended from the central part of the holding block is extended to the light introducing path position adjusting means to fix and the rotation is carried out around the bolt as an axis. The lower insulating means 13 may be provided between the turntable and holding block 11 and/or, between the turntable and light introducing path position adjusting means 12. The structure of the bolt 66 may be a rod-like member, as shown in FIG. 38, as far as it can be applied for the center axis of the holding block 11. The lower insulating means 13 is not shown in FIG. 38.

Figure 36:
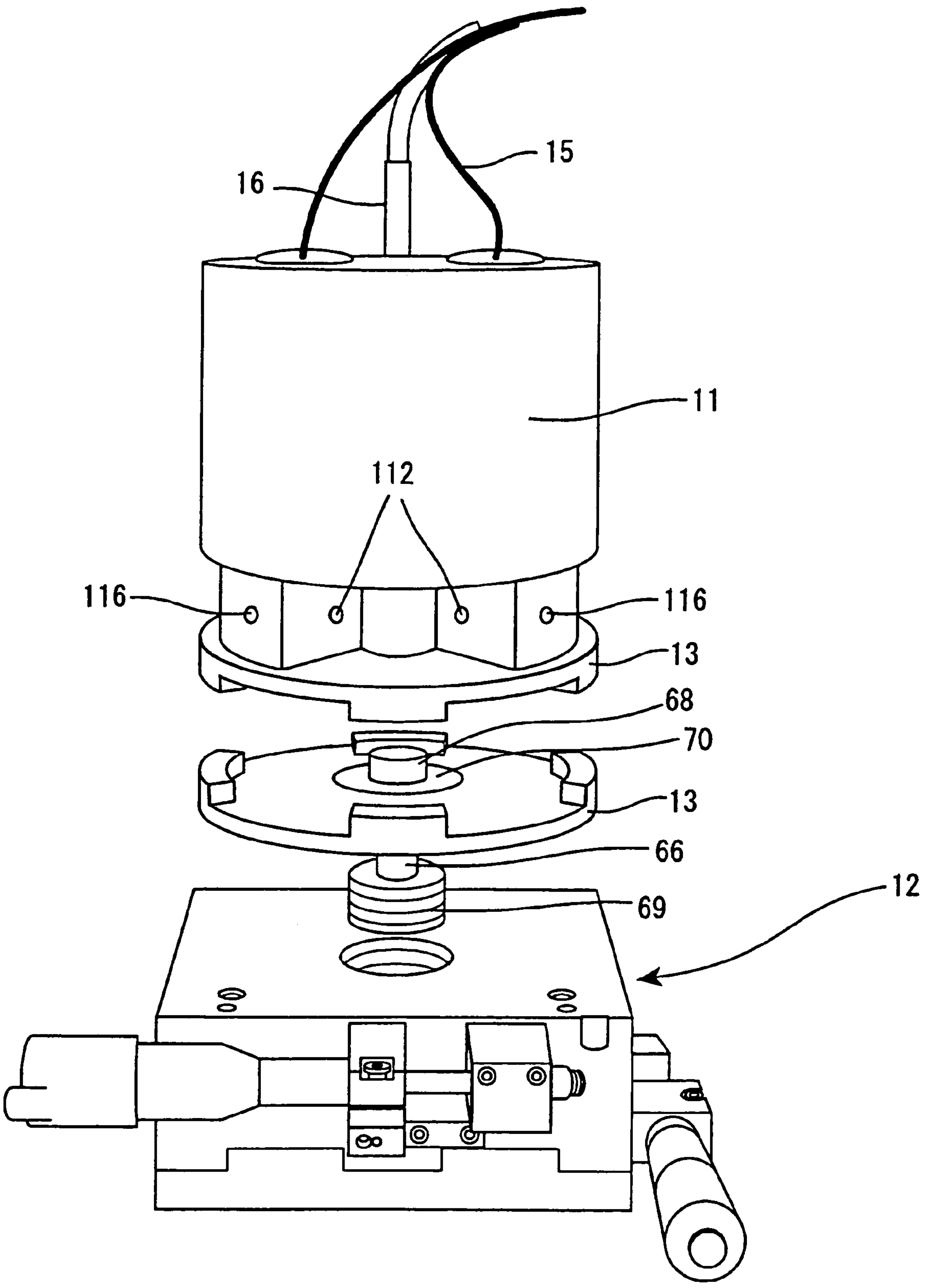
FIG. 36 is a schematic diagram showing the configuration in which the rotating means is embed between the holding block and the insulating means.
Figure 37:
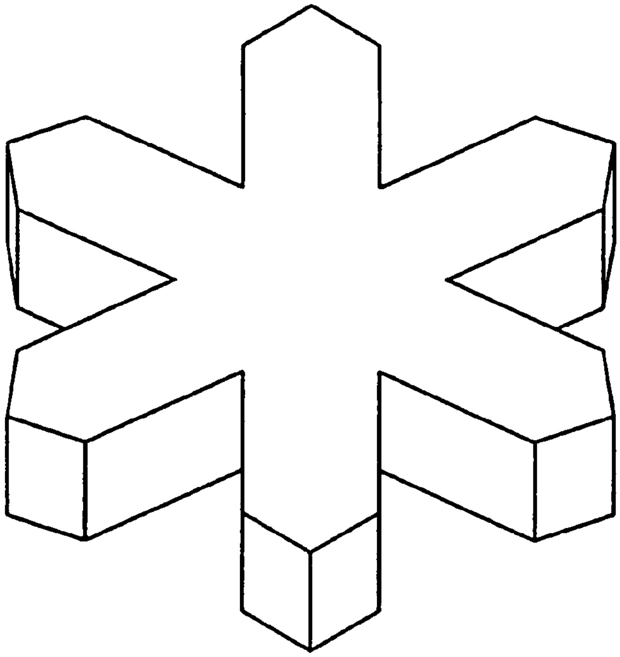
FIG. 37 shows a preferable mode of the section of the lower part of the holding block 11 being cut with a horizontal plane including a central line of the light introducing path 112 and being viewed from above, regarding the sample holder for spectrum measurement of the invention.
Figure 37:
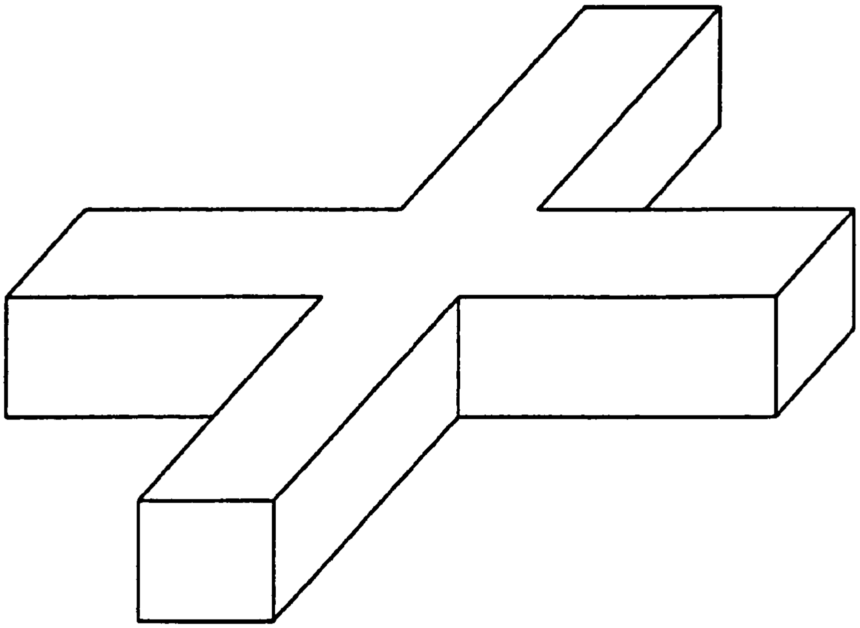

As the simple configuration among the mechanism to rotate the holding block around the center thereof as an axis in the present invention, as shown in FIG. 36, the configuration in which the insulating means 13 provided between the bottom of the holding block 11 and the light introducing path position adjusting means 12 is held or fixed to the light insulating path position adjusting means 12 by means of a bolt, a head of the bolt is plugged in a center of the bottom of the holding block and the holding block 11 is rotated around the head of the bolt by supporting the holding block with the bolt as the axis is preferable.

FIG. 36 shows a configuration in which the lower insulating means 13 is formed by two plates and the lower plate of the lower insulating means 13 and the light introducing path position adjusting means 12 are fixed by means of the bolt 66 by screwing a screw nut 69 having a bigger diameter than the diameter of the axis of the bolt 66 and being screwed outside thereof to the bolt 66. In this case, the screw nut 69 is a circular columnar shape. In this case, a washer 70 is enchased between a head 68 of the bolt and the lower plate of the lower insulating means to thereby rotate freely. The two plates of the lower insulating means 13 may be fixed each other by means of a screw and the like. The screw nut 69 having a bigger diameter than the diameter of the axis of the bolt 66 is screwed to the hole provided at the center of the light introducing path position adjusting means 12 to thereby both of the holding block 11 and the lower insulating means 13 finally obtained as the rotating means, is provided on the light introducing path position adjusting means 12. When the screw nut 69 is not screwed outside thereof, it is fixed by inserting to the hole provided at the center of the light introducing path position adjusting means 12. The screw nut 69 may be a hexagonal nut. When it is the hexagonal nut, it is preferred to be inserted to the hole provided at the center of the light introducing path position adjusting means 12 via a packing such as rubber or the like, or it is preferred that the hole is provided in a shape corresponding to the shape of the screw nut 69.

The above rotating means may be one obtained by inserting a rod-like member to the light introducing position adjusting means 12 instead of the bolt 66 as the rotating axis to the light introducing path position adjusting means 12, aside from screwing the bolt 66 or fixing by means of a screw nut. As the material of the rod-like member or the bolt 66, there can be used resin, iron, aluminum, SUS, ceramics and the like. Iron or SUS can be welded when it is inserted to the light introducing path position adjusting means. The rotating axis may be fixed with the given adhesive binder, however, it is preferred to be fixed by screwing to the hole, in view of the easiness of dismounting of the sample holder for spectrum measurement and maintenance. The diameter of the bolt 66 or the rod-like member as the rotating axis can be appropriately selected.

When the rotating axis is used, the lower insulating means 13 and the holding block 11 preferably have a hole with the specified diameter in order to introduce or hold the bolt 66 as the rotating axis. In such case, the rotating axis provided by protruding from the light introducing path position adjusting means 12, can be inserted into the insulating means 13 and/or the holding block 11 so as to give the rotating means 80 in the horizontal direction. The structure in which the center of the upper member of the lower insulating means 13 is provided with a protruding part and this protruding part protruding against the holding block 11 replaces the central axis or the head of the bolt 66 may be employed.

The specific installation configuration of the rotating means 80 of the invention is shown in FIG. 35. More simple and convenient configuration in which the rotating means 80 and the lower insulating means may be separated is shown in FIG. 38.

Specifically, the rotating means 80 may be a member in which the bolt 66 or the rod-like member as the central axis of the holding block 11 is inserted to form a rotating axis, and the representative member of such rotating means 80 is a turntable or the like. In FIG. 38, it is shown as the turntable 100. The insulating means 13 may be provided to one of top and bottom surfaces or both of them of the turntable or the like. The turntable and the insulating means are preferred to be provided between the holding block 11 and the light introducing path position adjusting means.

In such configuration, the material of the turntable as the rotating means may be metal such as SUS, iron, aluminum, inorganic material such as ceramic, heat resistant resin, or the like. The material, shape or the like of the insulating means to be used in this case may be a plate-like structure which can sufficiently serve the effect of the same. It may be, for example, a heat resistant resin such as fluororesin or polyamide, or a fiber-like material such as Kevlar or asbestos. As described above, when the rotating means 80 and the lower insulating means 13 may be provided separated parts, the sample holder for spectrum measurement of the invention can be produced in a simple and convenient manner with low cost. The functional and convenient configuration in which a partial structure of the insulating means 13 is included in the rotating means 80 is already described in the above, although the structure of the insulating means 13 is more complicated.

A material having insulating and low friction properties may preferably be used for the insulating means 13 because the holding block 11 can be rotated easily with low friction, and, for example, fluororesin material such as disk (3 to 10 mm thickness) of Teflon (trademark) or the like may be used. The insulating means may be disk of heat resistant resin such as polyamideimide, polyimide, polyetheretherketone or the like. The insulating means 13 is preferably formed from two disks made of Teflon as shown in FIG. 36, and by providing a gap between these disks that can hold nitrogen or air therein, effective heat insulating is enabled. The insulating means is preferably such that a washer 70 is enchased between a head 68 of the bolt and the lower member of the disk and is protruded from the lower member of two plates and the screw part of the bolt 66 is screwed into the hole provided on the light introducing path position adjusting means 12 directly to fix the insulating means to the light introducing path position adjusting means 12. The material of the insulating means may be a fiber-like material or expanded material.

A configuration in which the rotating means 80 is provided between the holding block 11 and the light introducing path position adjusting means 12 is preferable because, once the position is adjusted to one of the light introducing paths 112 for spectrum measurement, the adjustment of the position to another light introducing path for spectrum measurement is possible even though by using the rotating means, without changing the position in the vertical direction again. In case that the holding block of the invention includes the plurality of holding holes 111 of the liquid samples and, further, the rotating means, it is enabled easily to adjust the position of the light introducing path to the propagating route of the light for spectrum measurement even when the position of the plurality of the light introducing paths for spectrum measurement disagrees in the vertical direction because of having the position adjusting means. It is preferable, to enable easier spectrum analysis for the plurality of the liquid samples, that the rotating means 80 is installed so as to the position of the sample holding holes 111 coincides each other and it is parallel to the lower part of the horizontal surface of the holding block. And further, the rotating axis, such as the bolt 66, is preferred to be perpendicular to the lower part of the horizontal surface of the holding block.

As for the sample holder for spectrum measurement, a configuration in which spectra of two or more liquid samples are measured serially by rotating the holding block 11, by means of the rotating means 80, to a position of the light introducing path 112 aligning to the propagating route of the irradiation light for spectrum measurement, and adjusting again is preferable.

The above rotating means may be a manual one or an electromotive one. One example of the electromotive rotating means is described below.

At the edge of the installation fixing stage 120 or the light introducing path position adjusting means 12, an electric motor is installed in lengthwise or broadwise, and a gear is provided to an axis of the motor and the bolt 66 which is a central axis of the holding block 11 also, and the bolt 66 is rotated by transmitting the rotating power of the motor by a belt or the like. The bolt 66 may be directly connected to a rotating axis of a low-speed motor in a manner of direct-drive. A gear ratio is smaller for the motor side and larger for the central axis of the holding block side, to thereby enable fine adjustment by controlling the rotating speed by a computer or the like. By installing such an electromotive rotating means 80, a remote control becomes possible, and together with the temperature controlling device having a heating or cooling program, an automatic measurement of plural number of samples becomes possible.

Figure 2:
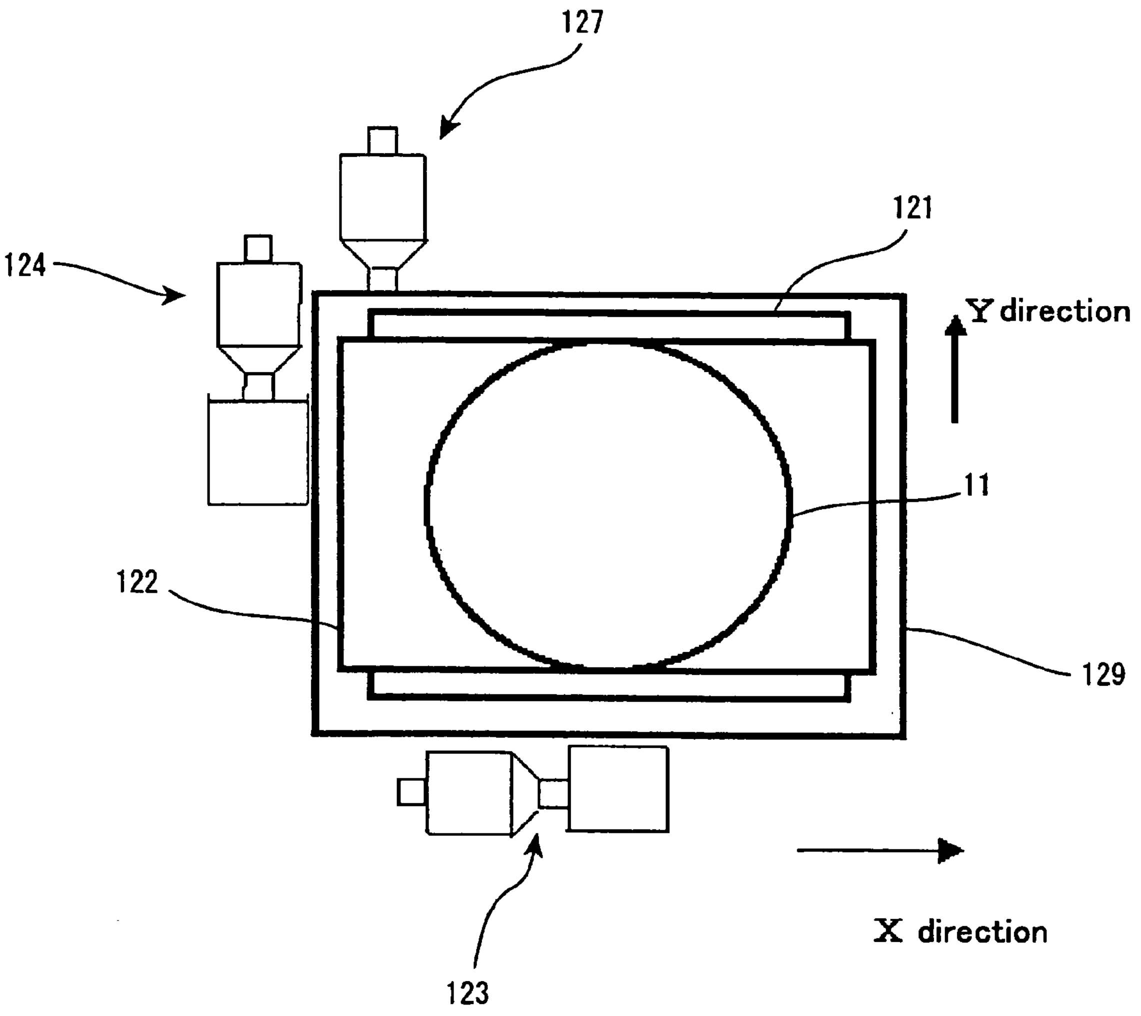
FIG. 2 is an elevation view (top view) as seen from above of each moving stage of the sample holder of the invention comprising, as a light introducing path horizontal direction position adjusting means 12-1 of the holding block 11, an X-direction operation unit 123 for adjusting the position in the X-direction along the propagating route of irradiation light, and a Y-direction operation unit 124 for adjusting the position in the Y-direction perpendicular to the X-direction, and, as a light introducing path vertical direction position adjusting means 12-2, a Z-direction operation unit 127 for adjusting the position in the Z-direction perpendicular to the X-direction and Y-direction.
Figure 3:
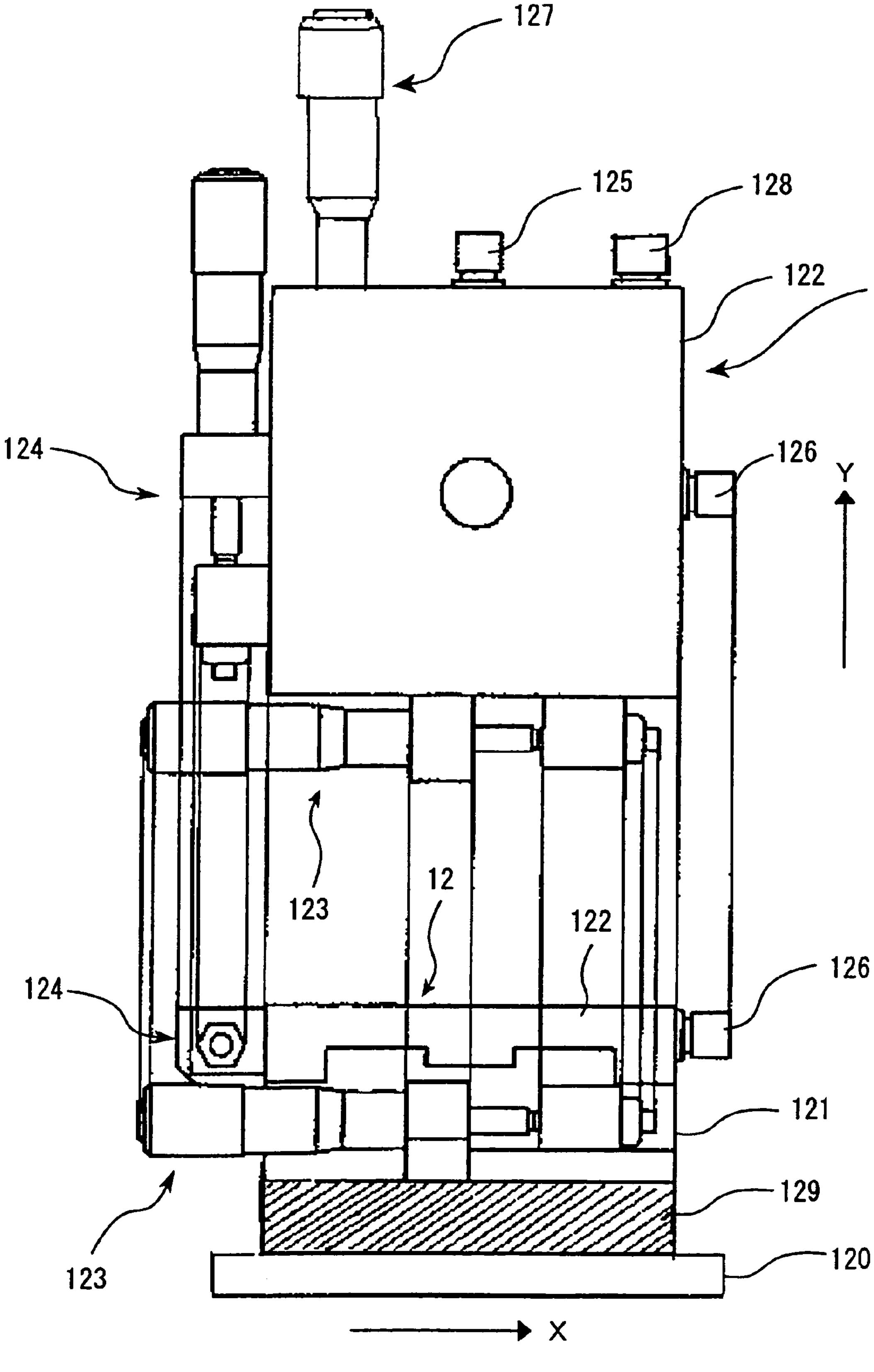
FIG. 3 shows an elevation view (top view) from above and a side view (bottom view) showing an example of a specific configuration of the position adjusting means in FIG. 2, further showing the Z-direction moving stage 129 in a shaded area, operation units for adjusting in each of X, Y and Z directions and fixing screws, and each moving stage movable in the X-direction, Y-direction and Z-direction.

FIG. 2 shows a mode of the holding block 11 having a moving stage comprising light introducing path horizontal direction position adjusting means 12-1 for adjusting the position of the light introducing path for introducing the irradiation light for spectrum measurement to the liquid sample in the sample holder for spectrum measurement of the invention so as to be introduced into the liquid sample by adjusting to the propagating route of the irradiation light for spectrum measurement, and the light introducing path vertical direction position adjusting means 12-2 for adjusting the position of the light introducing path of the holder in the vertical direction relative to the propagating route of the irradiation light, in a plan view as seen from the top of the holding block 11. FIG. 3 shows magnified plan view and side view of the stage portion of the position adjusting means as X-direction operation unit 123, Y-direction operation unit 124, and Z-direction operation unit 127.

As shown in FIG. 4, the lower part of the holding block 11 of the embodiment is a cross-shaped bottom 114 projecting in a cross shape when four sample holding holes 111 are provided at the equal distance. The cross-shaped bottom 114 is formed as a cross bump by cutting out, for example, four positions of the lower part of the holding block in a sector columnar shape so as to the bottom of the sample holding holes 111 are held in the lower part of the holding block and remained in the lower part of the holding block with adjusting the positions of the four sample holding holes 111.

When the lower side of the holding block 11 is thus formed as the cross-shaped bottom 114, as shown in the bottom view of FIG. 4, the light introducing path 112 is exposed on the wall surface projecting in a cross shape. Accordingly, as shown in the top view of FIG. 4, the light introducing path 112 is not required to penetrate through the holding block 11 entirely, but it is enough to penetrate through the projecting portion of the cross-shaped bottom 114. Hence, the light introducing path 112 can be shortened, so that the precise position adjustment by the light introducing path position adjusting means 12 described later can be enhanced. The above cross-shaped bottom is called as a star-shaped bottom according to the number of the sample holding hole 111.

As the configuration of the holding block 11, a lower part thereof is preferably formed by cutting out one or more sector columnar shape parts so as to form a sector columnar gap in the lower part of the holding block 11, so that a bottom of the hole 111 is still held at the lower part of the holding block 11, and also is still remained in the lower part of the holding block. Thus, the shape of the lower part of the holding block in which the introducing path of the light for spectrum measurement goes through is preferably a shape in which one or more sector columnar shape parts are cut out from the lower part so as to a sector columnar gap is formed and the sufficient part of the holding block for the safe control of the liquid sample temperature is remained around the sample holding hole 111 which can safely control the sample temperature. The lower part of the holding block after being cut out so as to form a sector columnar gap may be any configuration which can stably control the temperature of the sample holding hole 111, however, is preferably a configuration in which a plane being cut in a horizontal plane including a central line of the light introducing path 112 and viewed from above is cross-shaped or star-shaped. The star-shaped means, regarding the shape of the lower part of the holding block, when the plurality of the sample holding holes 111 are provided in a position equal from the heating apparatus, the star-like shape in which each of the sample holding holes 111 is placed at the apex of the star shape by cutting out the lower part of the holding block in a sector columnar shape so as to remain the sample holding holes 111. The cross-shaped is such case that the number of the sample holding hole 111 is four. The lower part of the holding block after being cut out so as to form a sector columnar gap is preferably a shape having six or less sample holding holes and, may be a shape having three sample holding holes or a shape having five sample holding holes, in viewpoints that the remaining part of the holding block after being cut out the sector columnar gap is enough and the thermal control of the sample holding block can be carried out stably. When the ray other than the light for spectrum measurement is introduced, the number of the sample holding hole is preferably four or six so that the ray introduced from the ray introducing path 116 other than for spectrum measurement can penetrate the holding block.

Figure 15:
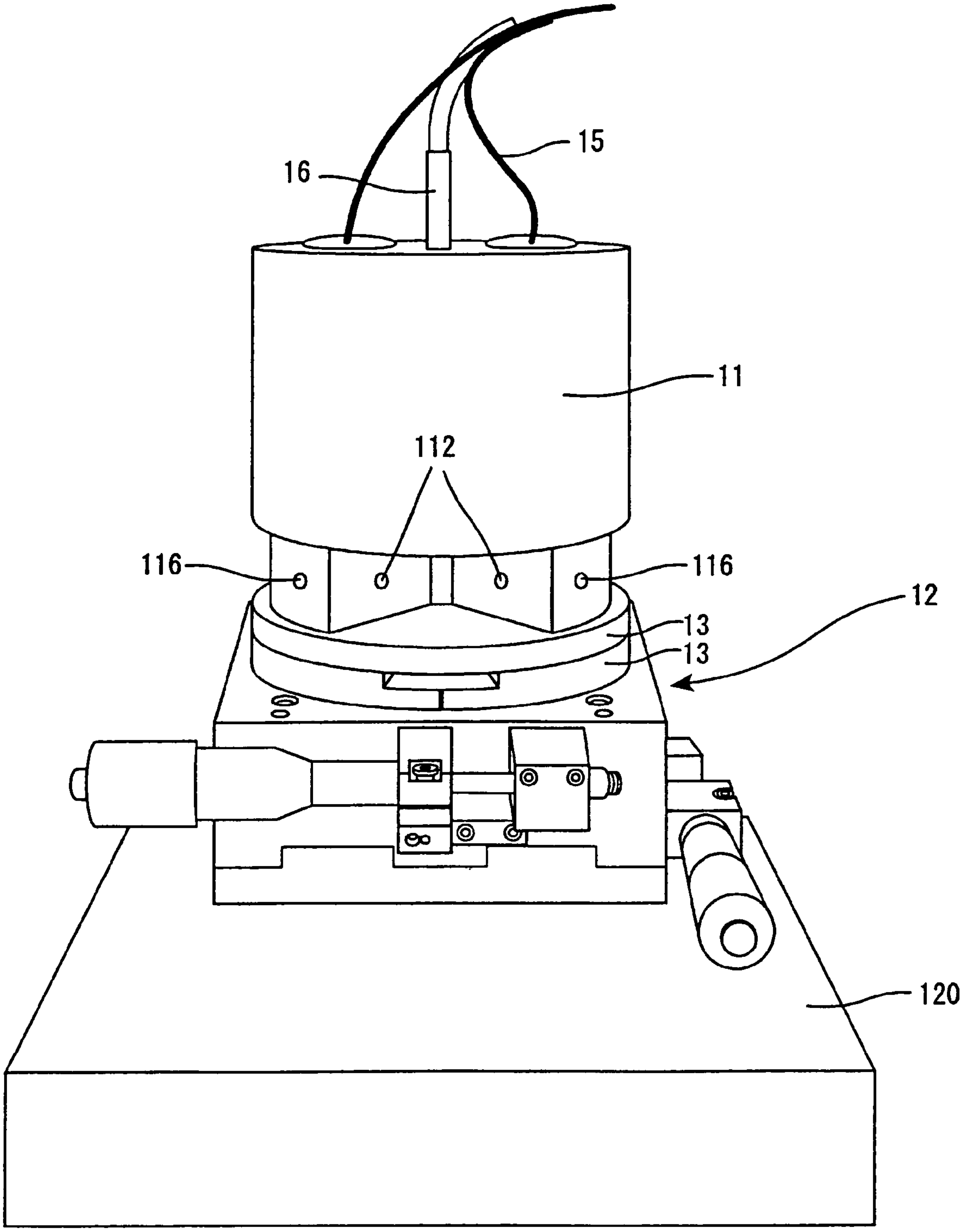
FIG. 15 is a front view of a preferred embodiment of the sample holder for spectrum measurement of the invention.
Figure 16:
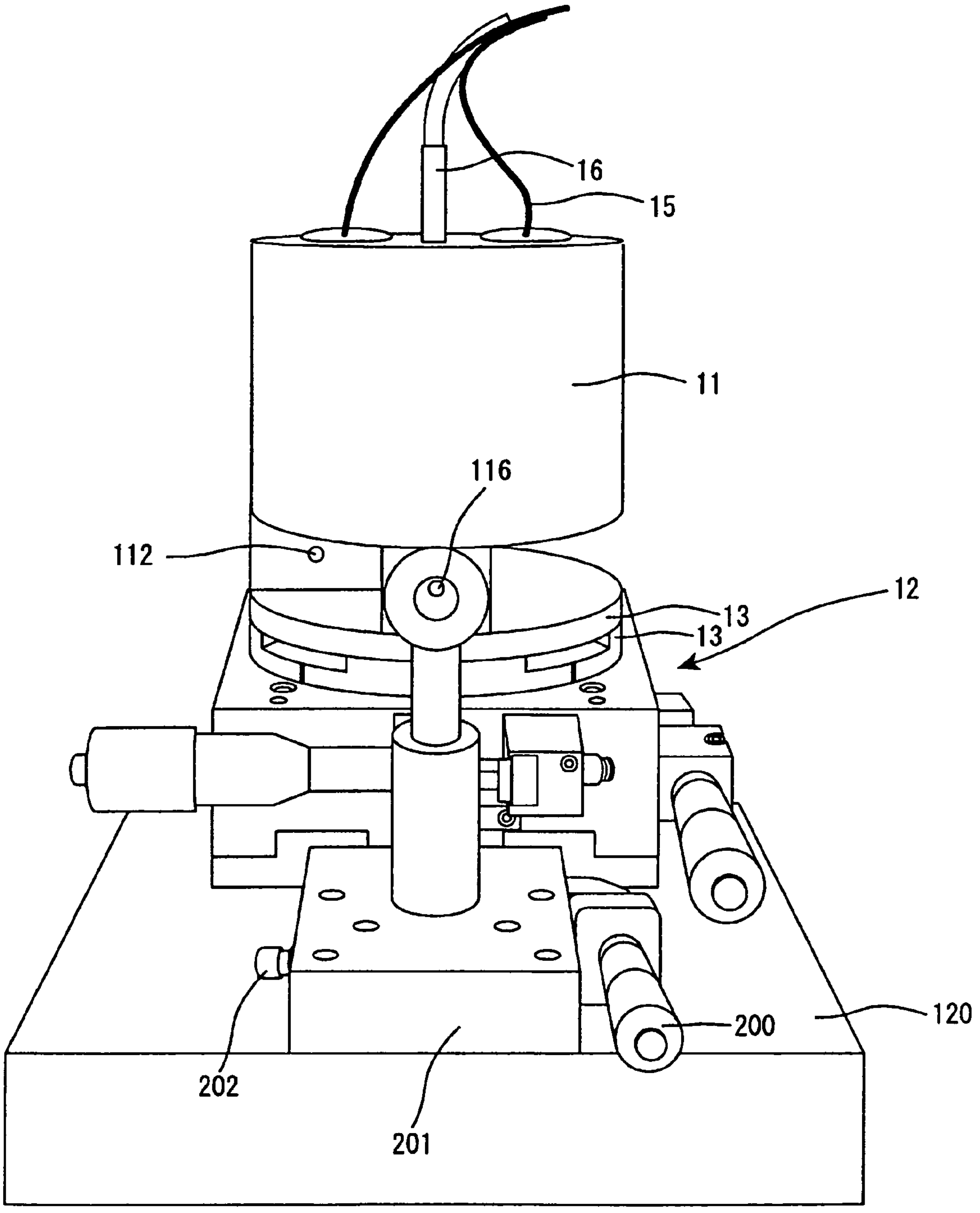
FIG. 16 is a front view of a preferred embodiment of the sample holder for spectrum measurement of the invention. In this diagram, ray irradiating means of the ray or electron beam other than the light for spectrum measurement is designed to be irradiated to the ray introducing path 116 of the ray other than that for spectrum measurement from the front side of the drawing. In this figure, a light holding means which is to be used when a optical fiber sensor light is used in order to introduce the ray other than the light for spectrum measurement. The light holding means 201 includes a vertical direction moving operation unit 200 and a position fixing screw 202 in order to easily align the position with the ray introducing path 116. The Z-direction operation unit to adjust the position of the holding block in the vertical direction is hidden in this figure.
Figure 17:
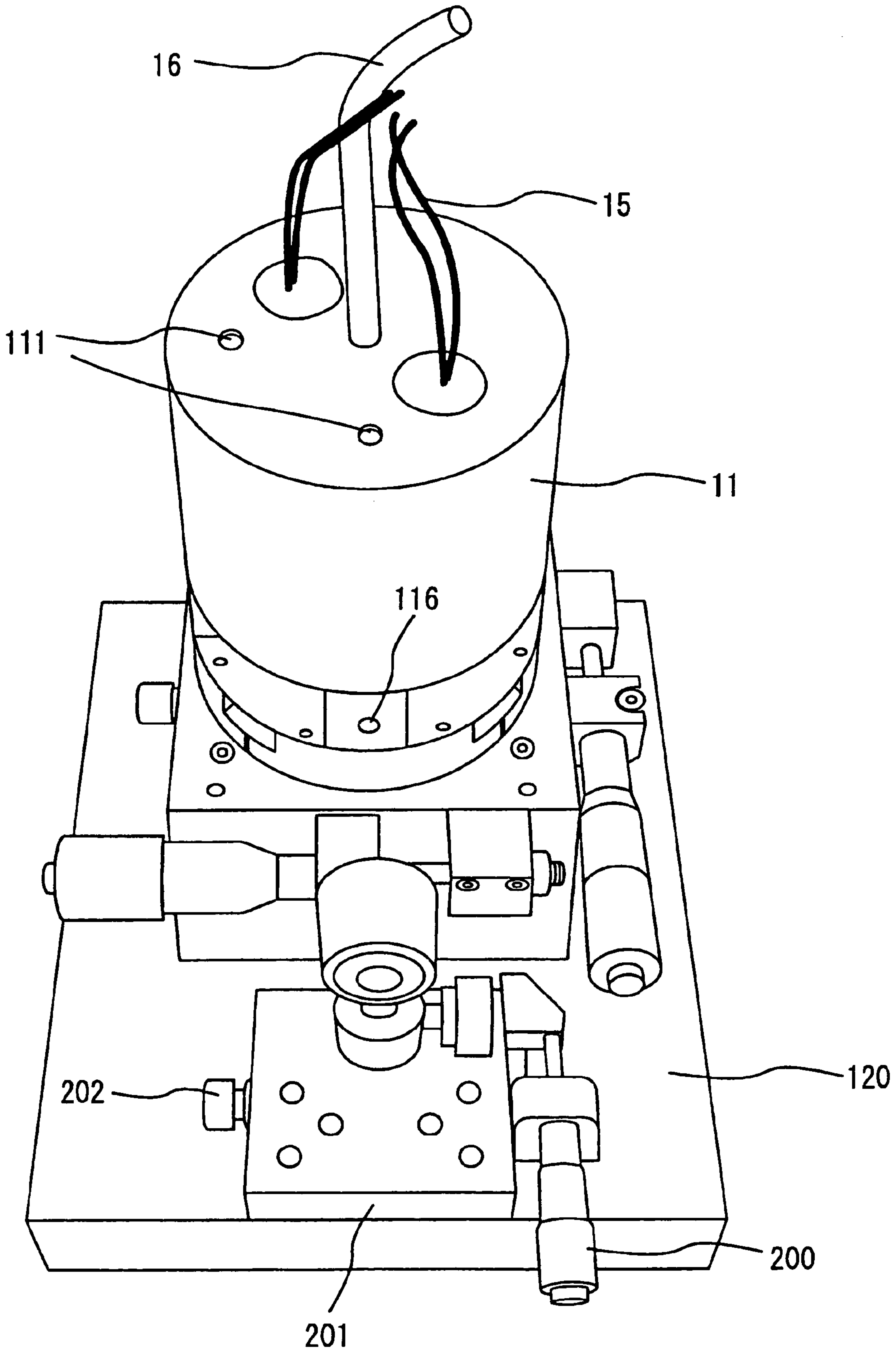
FIG. 17 is an oblique above view of the sample holder for spectrum measurement in FIG. 16.
Figure 18:
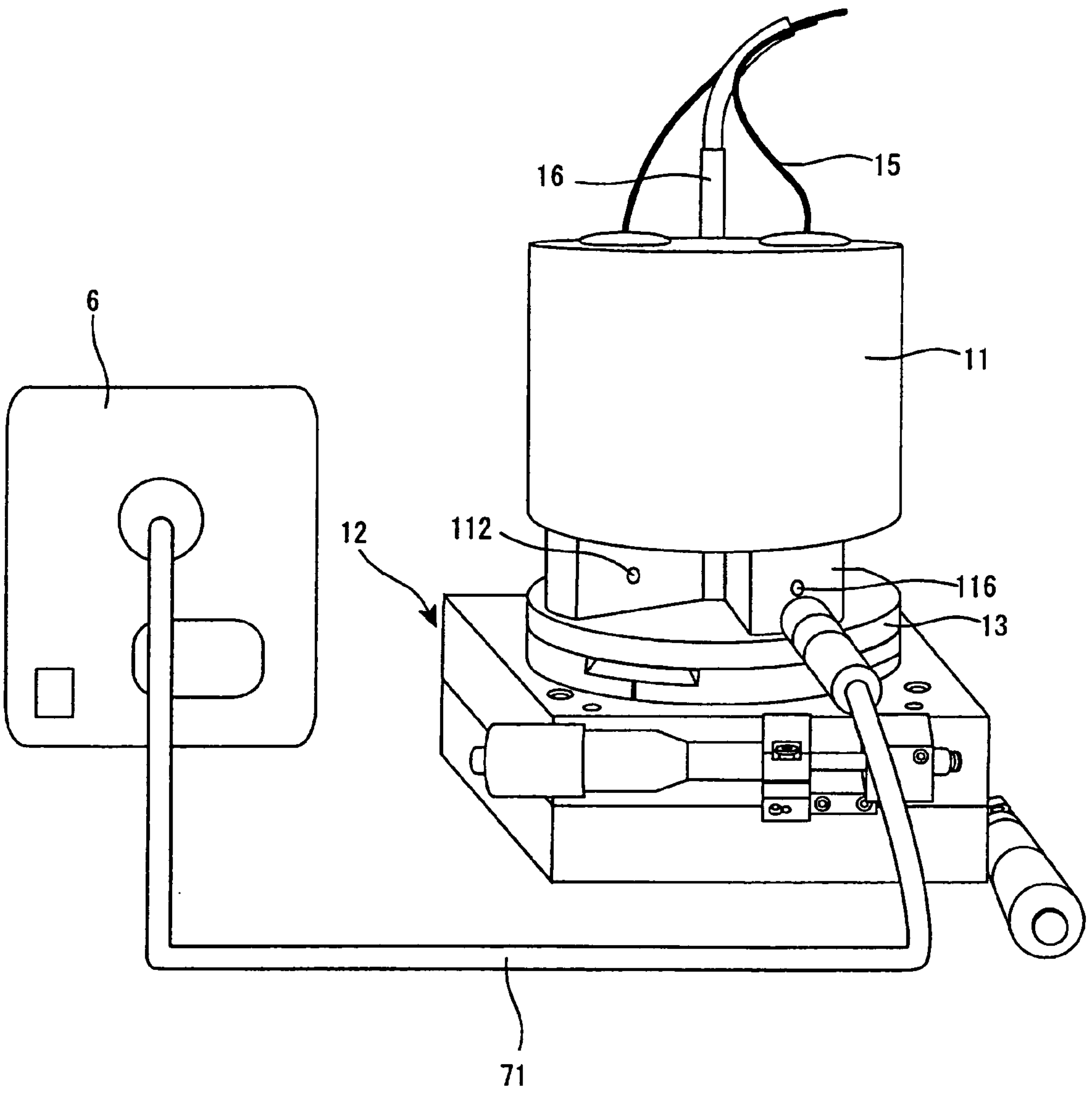
FIG. 18 is a view of a preferred embodiment of the sample holder for spectrum measurement of the invention. In this diagram, the ray other than that for spectrum measurement emitted from a ray irradiating apparatus 6 of the ray other than the light for spectrum measurement is introduced from a ray introducing path 116 of the light other than that for spectrum measurement. In this figure, the Z-direction operation unit is hidden.
Figure 19:
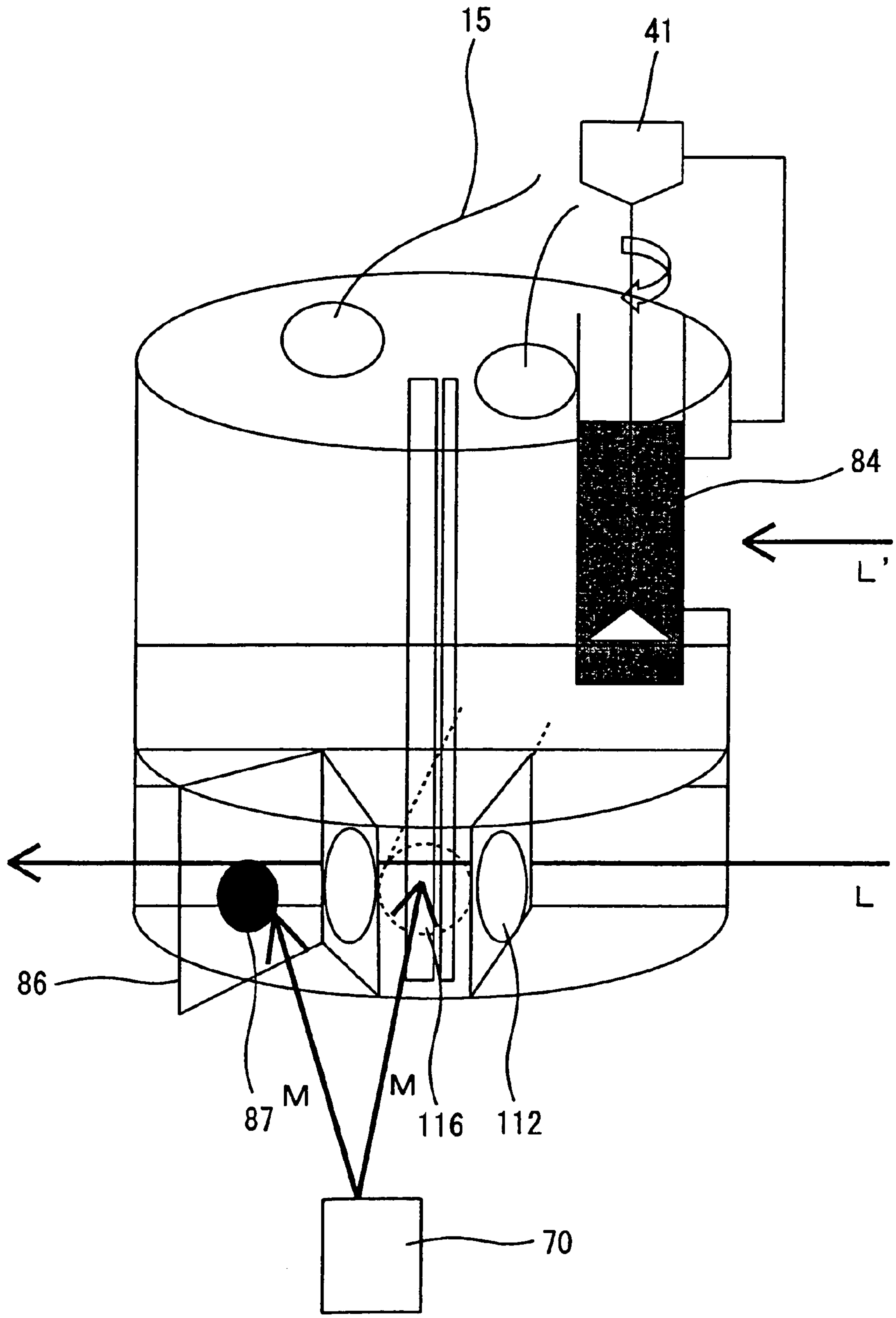
FIG. 19 is a diagram showing a configuration of using thin film holder component and a configuration of emitting Raman light regarding the sample holder for spectrum measurement of the invention.

The lower part of the holding block may have a structure which can internally include a bolt 66 or a head 68 of the bolt as a member of the rotating means 80 and as a central axis. Thus, as shown in FIG. 4 or FIG. 19, the lower part of the holding block is preferably cross-shaped with sufficient width. The lower part of the holding block may have a structure in which a part of the central part thereof partly has a side of the circular column in order to hold a bolt 66 or a head 68 of the bolt as a central axis, as shown in FIG. 15, FIG. 18 or FIG. 36.

The light introducing path 112 is formed in the horizontal direction (lateral direction) relative to the sample holding holes 111 formed in the vertical direction (longitudinal direction), but since they are formed to penetrate through the cross bottom 114, the light introducing path 112 intersects at the lower part of the sample holding hole 111. When the light introducing path 112 intersects at the lower part of the sample holding hole 111, it is preferred because the spectrum can be measured from the liquid sample 40 if the amount (volume) of the liquid sample 40 dispensed into the sample container 30 held in the sample holding hole 111 is relatively small.

The structure of the lower side of the holding block 11 is not limited to the cross bottom 114, but may be formed in any structure as far as the distance of the light introducing path 112 can be shortened relatively.

In FIG. 1, the sample holder 3 is schematically shown so that the heater 15 and temperature sensor 16 are formed integrally with the holding block 11 in order to enable the temperature control. The heater and the temperature sensor may be integrated. For example, as shown in FIG. 4, the heater 15 may be put into the heater hole 113. Similarly, the temperature sensor 16 may be provided in the holding block by forming a temperature sensor hole (not shown) and putting the same therein, but more preferably it is provided in the holding block 11 by putting the same into any of four sample holding holes 111. Thus, the temperature can be measured in a condition similar to the heated liquid sample 40. The bottom part of the heater 15 is preferably located in the upper part of the holding block above the lower part of the holding block, when the lower part of the holding block is cut out so as to form the sector columnar gap.

The heater 15 may be any heater or heat medium capable of heating the liquid sample 40, but as in this embodiment, it is preferred to heat the liquid sample 40 indirectly by heating the entire holding block 11. Therefore, as compared with direct heating by the heater 15, it is possible to heat the liquid sample 40 more stably. The structure of the heater 15 is preferably a conventional structure generally known as throw-in heater. It also includes a technique to heat by installing a piping around the holding block 11 and circulating heat medium in the piping. As the temperature sensor 16, various known thermometers and sensors may be used.

The heater 15 and temperature sensor 16 are preferably connected electrically to the temperature controller 17 as shown in FIG. 1(*a*). The temperature controller 17 is not particularly specified as far as the heating temperature by the heater 15 can be adjusted and controlled on the basis of the temperature measured by the temperature sensor 16. The temperature controller 17 may be integrated with the spectrophotometer, or may be included in the sample holder 3 for spectrum measurement, or it may be an optional structure independent from the sample holder 3 for spectrum measurement or the spectrophotometer main body.

The heating temperature by the heater 15 in the invention may be about 200° C. in the upper limit in the application of polymerization of monomer such as methyl acrylate as mentioned in the examples below. If heating is possible up to this temperature, it is enough to proceed polymerization sufficiently. If the heating temperature is too high, it is not preferable as adverse effects by heat are caused on the spectrophotometer main body or light introducing path position adjusting means 12 in spite of insulating means such as the lower insulating means 13.

Figure 9:
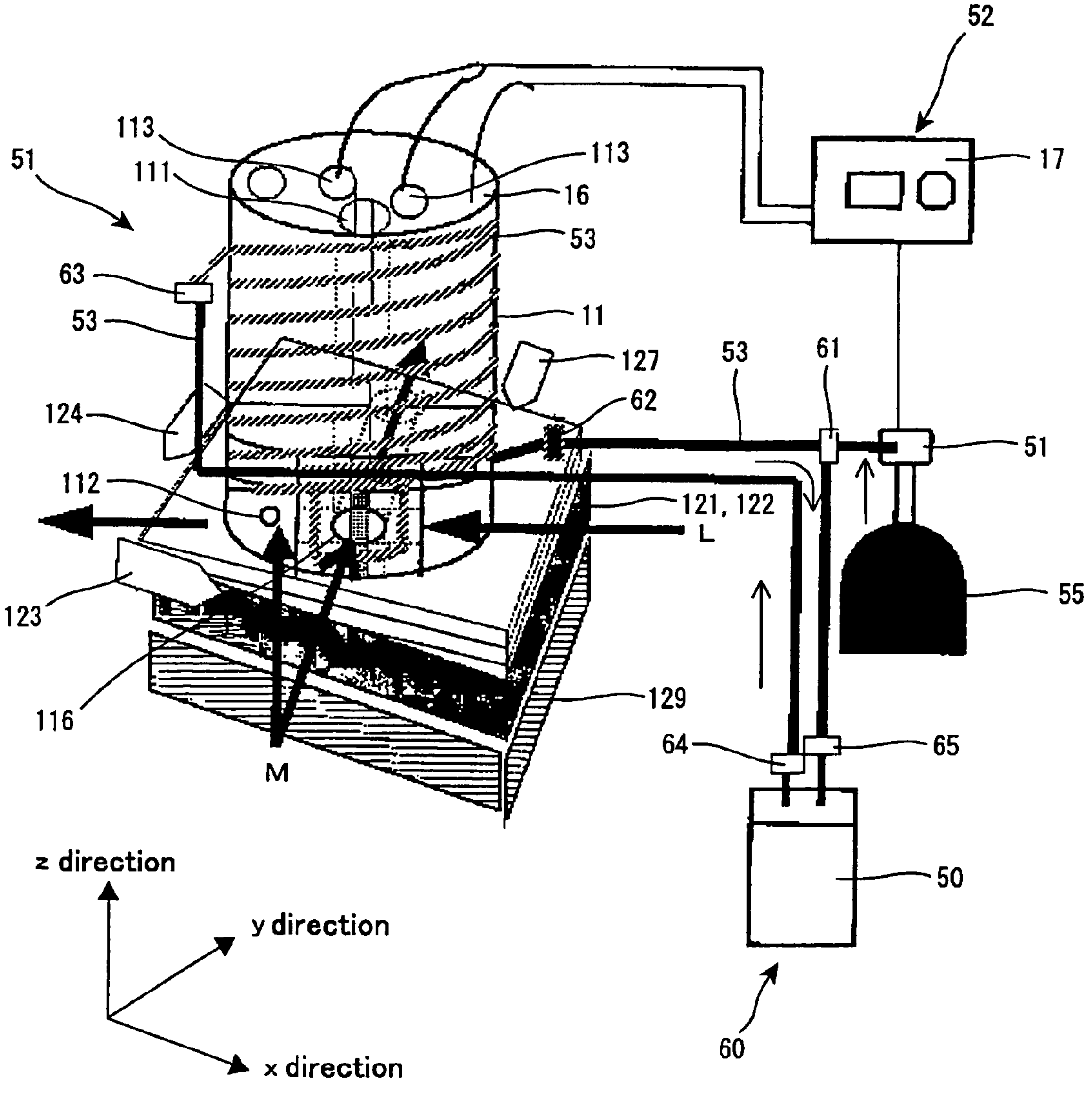
FIG. 9 is a diagram showing a specific structure of a sample holder 31 for spectrum measurement comprising an apparatus 51 for circulating a refrigerant 50 or liquid nitrogen 55 so as to keep the liquid sample at low temperature of 10° C. or less of the invention.

The sample holder for spectrum measurement of the invention may be the sample holder 31 for spectrum measurement having the apparatus 51 for circulating the refrigerant 50 in the holding block to keep the liquid sample at low temperature of 10° C. or less. As shown in FIG. 9, the holding block 11 preferably has the apparatus 51 for circulating the refrigerant 50 to cool the holding block 11 so as to keep the liquid sample at low temperature condition. More specifically, it is a configuration in which the refrigerant is circulated around the holding block 11 by means of a piping 53 by way of a valve for supplying the refrigerant 50 such as liquid nitrogen from a storage tank 55. The refrigerant may be circulated in the holding block 11 by means of the piping.

The liquid sample (polymerizable composition) to be used includes a composition in which the polymerization reaction is initiated at an ordinary temperature or a low temperature by incorporating the polymerization initiator and the accelerator. The sample holder for spectrum measurement of the invention can measure spectrum of such target of the measurement which is such a composition or does not require the temperature increasing. Because spectrum measurement can be carried out while irradiating the light other than the light for spectrum measurement to the liquid sample, the measurements under various conditions are feasible.

As the apparatus for circulating the refrigerant, a cooling water circulating apparatus, a liquid nitrogen circulating apparatus and the like are suitable. As the refrigerant, liquid nitrogen, ethylene glycol or the like may be used. An appropriate temperature range is slightly different between the low temperature state by circulation of liquid nitrogen and low temperature state by circulation of ethylene glycol or the like. The mechanism for circulating the refrigerant is also slightly different. Representative examples are shown in FIG. 9. FIG. 9 shows a configuration in which both a liquid nitrogen circulating apparatus 55 for circulating liquid nitrogen, and a cooling water circulating apparatus 60 for operating by switching to ethylene glycol or other refrigerant 50 can be used in combination. In the diagram, L denotes the irradiation light for spectrum measurement, and M shows irradiation light other than that for spectrum measurement such as UV, capable of being emitted to the liquid sample.

The sample holder 31 for spectrum measurement having the apparatus 51 for circulating the refrigerant 50 preferably has a configuration in which the refrigerant 50 is circulated by means of the cooling water circulating apparatus 60, using antifreeze liquid such as ethylene glycol as refrigerant, around the holding block 11 using the piping 53, in low temperature range of 10° C. to −30° C., to control the temperature of the holding block at specified low temperature state. It may be such configuration that the refrigerant 50 is introduced in the holding block to circulate by means of the piping to control the temperature of the holding block at low temperature state. When liquid nitrogen is used as a refrigerant, the holding block 11 can be controlled at a very low temperature range of −30° C. to −150° C. In the case of the liquid nitrogen, in FIG. 9, it is stored in a liquid nitrogen circulating apparatus 55, and is supplied to the piping 53 by way of a liquid nitrogen supply valve.

The above cooling water circulating apparatus may be one having the refrigerant cooling function and the refrigerant circulating function. The cooling water circulating apparatus is an apparatus sometimes referred to as a cool nix, a low-temperature circulator or the like. The cooling water circulating apparatus is preferably an apparatus for circulating the refrigerant comprising water and ethylene glycol. The liquid sample can be cooled to −30 to −100° C. by using the cooling water circulating apparatus. As the cooling water circulating apparatus, a cooling water circulating apparatus (product of Tokyo Rikakikai Co., Ltd.) or the like is preferable.

As the liquid nitrogen circulating apparatus, one having liquid nitrogen storing function and liquid nitrogen circulating function may be used. The liquid nitrogen circulating apparatus is preferably such configuration that an solenoid valve is provided to a container of liquid nitrogen for a thermal analyzer (product of Seiko Instruments Inc., Bruker AXS, and the like) or for a dynamic headspace sampler (product of Japan Analytical Industry Co., Ltd.), the container of liquid nitrogen is pressurized with nitrogen, the temperature is controlled by a temperature controller and the apparatus is turned on and off by means of the solenoid valve. By using liquid nitrogen, the liquid sample can be cooled to −30 to −150° C.

In FIG. 9, the respective direction operation units 123, 124, and 127 attached to the light introducing path position adjusting means of the invention are shown in a simplified form. As the respective direction moving stages, an X-direction moving stage 121, a Y-direction moving stage 122, and a Z-direction moving stage 129 are shown in a simplified form.

The liquid nitrogen supply valve is preferred to be a solenoid valve, and a temperature control device 17 and liquid nitrogen supply valve are connected by a relay circuit by way of a temperature sensor 16 provided in the holding block 11, and it is preferred to adjust the flow rate of the refrigerant by opening or closing the liquid nitrogen supply valve to adjust to a specified temperature.

As for the sample holder 31 for spectrum measurement having the apparatus 51 for circulating the refrigerant 50 for keeping the liquid sample at low temperature state of 10° C. or lower, it is also preferred to have the insulating means. Specifically, when controlling to a low temperature of 10° C. to −30° C., or when adjusting to a very low temperature in a range of −30° C. to −150° C., the insulating means is effective for preventing dew condensation in the light introducing path position adjusting means or the installation fixing stage as the mechanism for moving the moving stages in the X-direction, Y-direction or Z-direction. Similarly, when the insulating cover 14 is provided, low temperature control is easy especially when adjusting to a very low temperature in a range of −30° C. to −150° C. and dew condensation can also be prevented.

In particular, when cooled to −10° C. or less, dew (water drop) is likely to condense depending on the ambient humidity. Dew condensation is a serious problem depending on the object of measurement, and in such a case dew condensation may be prevented by blowing dry air into the measuring chamber or the holder. Dry air can be also supplied into the insertion hole for inserting the liquid sample, and it is preferable to have a piping for replacing the atmosphere in the insertion hole with dry air. It is particularly preferable and effective to prevent dew condensation by supplying dry air into the insulating cover or outside of the insulating cover to keep the atmosphere in dry state. In FIG. 9 showing an embodiment of the sample holder for spectrum measurement having the apparatus 51 for circulating the refrigerant 50 to keep the liquid sample at low temperature of 10° C. or less, the insulating cover and the piping for introducing the dry air is provided (not shown in FIG. 9).

The sample holder for spectrum measurement of the invention is preferred to have a second temperature sensor 18 to be used together with the temperature sensor 16. The second temperature sensor 18 may be used merely to measure the temperature of the liquid sample 40, but it is more effective to control the low temperature state strictly when it is connected to the temperature controller 17 and designed to adjust the solenoid valve for controlling the refrigerant flow rate by detecting the electric signal generated from the temperature sensor at the temperature controller 17 to operate the program, same as the temperature sensor 16. By an electric signal from the temperature controller 17, the cooling water circulating apparatus 60 or valve is adjusted, and the flow rate of the refrigerant or liquid nitrogen is adjusted so as to be controlled to a desired temperature. By operating the heater by a relay circuit as desired, a more precise temperature control is realized. Since dew condensation may occur in measurement in low temperature state, the electric route, heater and sensor are preferred to be in waterproof specification for prevention of current leak. In FIG. 9, although each of the cooling water circulating apparatus 60 containing the refrigerant 50 and the liquid nitrogen circulating apparatus 55 is shown independently, both of them are corresponded to the apparatus for circulating the refrigerant.

Preferred modes of temperature adjustment are explained below.

<Refrigerant Circulation Cooling System for IR Measurement (10° C. to −30° C.)>

(i) As for the cooling method of 10° C. to about −30° C., ethylene glycol is used as refrigerant 50, and the refrigerant cooled by the cooling water circulating apparatus 60 is circulated. The liquid nitrogen circulating apparatus 55 in FIG. 9 is replaced with the cooling water circulating apparatus 60.

(ii) Removing the joint 61, the container of liquid nitrogen is dismounted. Attaching each joint, the cooling water circulating apparatus 60 is set in placed.

(iii) Turning on the power source of the cooling water circulating apparatus, water and ethylene glycol both as refrigerant 50 is circulated in the piping 53, and the temperature is controlled in a range of 10° C. to about −30° C.

<Liquid Nitrogen Cooling System for IR Measurement (−30° C. to −150° C.)>

(A) Removing joints 61, 63, 64, 65, dry nitrogen is blow into the piping 53 for 5 minutes from the joint 63 to purge out the refrigerant remaining in the piping.

(B) Attaching the container of liquid nitrogen, it is connected to the piping 53 by the joint 61, and each joint is connected to the piping.

(C) Supply nitrogen gas, a pressure of about 0.1 MPa is applied by the gauge of the liquid nitrogen container.

(D) The temperature controller is set to a desired temperature of cooling, and the solenoid valve is turned on or off, and the liquid nitrogen circulates in the piping, and the holder 11 is cooled to the set temperature.

As explained above, the apparatus 51 for circulating the refrigerant 50 preferably has a joint which can switch the refrigerant to be used to control the temperature between 10° C. and −30° C., and the refrigerant to be used to control the temperature between −30° C. and −150° C.

The light introducing path position adjusting means 12 of the sample holder of the invention is preferred to comprise, as shown in FIG. 1(*a*), both the light introducing path horizontal position adjusting means 12-1 for adjusting the relative position of the light introducing path 112 relative to the propagating route L irradiated from the light irradiating means 21 in the X-direction and in the Y-direction orthogonal to the X-direction, and the light introducing path vertical direction position adjusting means 12-2 for adjusting the position in the Z-direction perpendicular to the X-direction and Y-direction.

By having the mechanism for finely adjusting the position of the sample holder more preferably in three directions of X-direction, Y-direction and Z-direction depending on the light irradiating unit, the sample holder for spectrum measurement of the invention can be applied in various structural analysis devices, and analytical devices (spectrophotometer) by different manufacturers somewhat different in the position of the light emitting unit.

FIG. 3 shows a side view of the position adjusting means in the lower part of the drawing showing the X-direction. It also shows a plan view as seen from above the position adjusting means in the upper part of the drawing showing the Y-direction. Although not shown in the plan view of the upper part, the side view of the lower part shows an example of the light introducing path vertical direction position adjusting means 12-2 capable of adjusting the position in the Z-direction (shaded area in the drawing).

Figure 8:
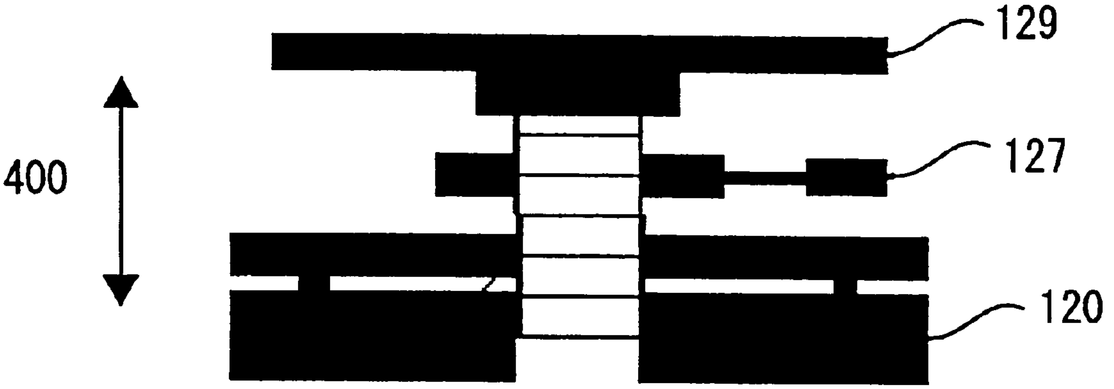
FIG. 8 is a magnified view showing the relation of Z-direction operation unit 127, Z-direction moving stage 129, and installation fixing stage 120.

FIG. 8 is a magnified view showing the relation of the Z-direction operation unit 127 as the Z-direction position adjusting means, the Z-direction moving stage 129, and the installation fixing stage 120. Reference numeral 400 is an arrow schematically showing the Z-direction. When the rotary nozzle of the Z-direction operation unit 127 is turned to the right, the Z-direction moving stage 129 moves up. When the rotary nozzle of the Z-direction operation unit 127 is turned to the left, the Z-direction moving stage 129 moves down.

The above light introducing path horizontal direction position adjusting means 12-1 preferably comprises an X-direction operation unit and an X-direction fixing unit as well as a Y-direction operation unit and a Y-direction fixing unit, and the light introducing path vertical direction position adjusting means preferably comprises a Z-direction operation unit and a Z-direction fixing unit.

Specifically, as shown in top view and bottom view of FIG. 3, the light introducing path position adjusting means 12 of the embodiment comprises the installation fixing stage 120, X-direction moving stage 121 disposed on the installation fixing stage 120 movably in the X-direction, Y-direction moving stage 122 disposed movably in the Y-direction, and Z-direction moving stage 129 disposed movably in the Z-direction. As shown in the top view of FIG. 3, it further comprises the X-direction operation unit 123 for moving the moving stage 121 in the X-direction, the Y-direction operation unit 124 for moving the moving stage 122 in the Y-direction, the Z-direction operation unit 127 for moving the moving stage 129 in the Z-direction, X-direction position fixing screw unit 125 for fixing after determining the position in the X-direction of the moving stage 121, Y-direction position fixing screw unit 126 for fixing after determining the position in the Y-direction of the moving stage 122, and Z-direction position fixing screw unit 128 for fixing after determining the position in the Z-direction of the moving stage 129. The order of installation of each moving stage 121, 122 and 129 is not particularly limited.

Figure 6:
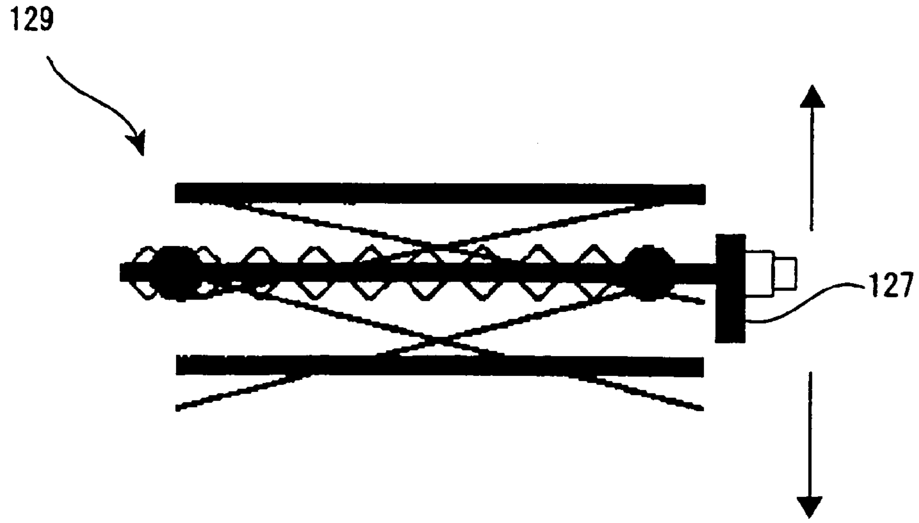
FIG. 6 is a diagram showing a structure of Z-direction moving stage 129 having a mechanism to move the Z-direction moving stage in the vertical direction, being designed to move vertically by a jack mechanism. The Z-direction operation unit 127 is rotated clockwise to move up, and counterclockwise to move down.

The Z-direction moving stage 129 disposed movably in the Z-direction has a structure which can move the internal jack mechanism vertically by rotating the Z-direction operation unit 127 as shown in FIG. 6. Moreover, the moving stage 129 disposed movably in the Z-direction may be concealed by the moving stage 121 or moving stage 122. In FIG. 3, to emphasize the location of the Z-direction moving stage 129, it is indicated in shaded area, and the installation fixing stage 120 is provided at the lowest position of the moving stage.

The specific shape of the installation fixing stage 120, X-direction moving stage 121, Y-direction moving stage 122, and Z-direction moving stage 129 may not be particularly limited, however, usually conform to the shape of the measuring chamber 23 as shown in FIG. 2 or FIG. 3, and all of them maybe square-shaped.

The operation mechanism of the X-direction operation unit 123, Y-direction operation unit 124, and Z-direction operation unit 127 is not particularly limited as far as it is designed to be able to move in each direction and adjust the position of the light introducing path 112 accurately to the propagating route L of the irradiation light for spectrum measurement. In this embodiment, as shown in FIG. 3, it is preferred to have a mechanism of moving each table in the X-direction or Y-direction by rotating, such as the micrometer provided at each side corresponding to the X-direction or Y-direction on the moving stage 121 or 122, or a jack mechanism for moving the moving stage 129 vertically by rotation in the Z-direction.

The mounting position of the Z-direction moving stage 129 may be in the sequence of the installation fixing stage, moving stage 129, moving stage 121, and moving stage 122 as shown in FIG. 3 or FIG. 5, or in an interposing configuration in the sequence of the installation fixing stage, moving stage 121, moving stage 129, and moving stage 122. In such configuration, the position of the holding block 11 disposed on the moving stages 121, 122, 129, that is, the position of the light introducing path 112 can be adjusted accurately and precisely in the X-direction, Y-direction and Z-direction. A magnified view of the Z-direction operation unit 127 and moving stage 129 is shown in FIG. 6 and FIG. 8.

A specific structure of the X-direction position fixing screw unit 125, Y-direction position fixing screw unit 126, and Z-direction position fixing screw unit 128 may be, as shown in FIG. 3, a configuration using a bolt (or a screw) provided at the side of the moving stage 122. The sample holder having a mechanism for adjusting in three directions of X-direction, Y-direction and Z-direction according to the light irradiating means is a preferred mode to be provided in the sample holder 31 for spectrum measurement having the apparatus 51 for circulating the refrigerant 50 to keep the liquid sample at low temperature of 10° C. or less. The detail is same as mentioned above and the explanation is omitted herein.

An alternative configuration of the X-direction or Y-direction position adjusting means (light introducing path horizontal direction position adjusting means 12-1) may be one in which an electric motor is provided instead of the micrometer as an operation unit to allow to move in X-direction or Y-direction automatically. In this case, the structure of the operation unit is preferably a screw-system or a gear-system. The position adjustment by the electromotive operation unit is preferably done by joystick, computer control while adjusting the position with looking the intensity of interferogram of the infrared or Raman light on the monitor. By using this configuration, the remote control is enabled and position adjustment becomes easy because the position can be adjusted while looking the intensity of the interferogram on the monitor.

An alternative configuration of the Z-direction position adjusting means includes a hydraulic press system. Such configuration is, for example, preferably one in which a central axis is provided at the center of the holding block 11 and the light introducing path position adjusting means 12, and the central axis is rendered as the hydraulic system, to thereby enable the movement of the holding block in vertical direction. It is also preferred the movement invertical direction is carried out remotely from the outside of the measuring chamber by computer control. The movement by hydraulic system is preferably done manually or automatically (electrically) to adjust the height. As same as the case using the electric motor as the alternative configuration of the X-Y direction position adjusting means (light introducing path position adjusting means 12-1), the remote control is enabled, and the position adjustment becomes easy because the position adjustment can be carried out while looking the intensity of the interferogram on a monitor. A position sensor may be provided to enable the movement of the holding block 11 by the rotating means 80, and the X-direction or Y-direction or Z-direction position adjusting means by computer control.

In the sample holder for spectrum measurement and spectrophotometer of the invention, as shown in FIG. 1(*a*), (*b*), a lower insulating means 13 is preferably disposed between the holding block 11 and the light introducing path position adjusting means 12, and further as shown in FIG. 1(*b*), an insulating cover 14 is provided so as to cover the surrounding of the holding block 11.

As the lower insulating means 13 and insulating cover 14 are provided, the holding block 11 and light introducing path position adjusting means 12 can be thermally insulated. As a result, the heat for heating the liquid sample 40, that is, the heat of the holding block 11 is prevented from being transferred to the light introducing path position adjusting means 12, measuring chamber 23 or the spectrophotometer, or such transfer can be suppressed. The insulating cover 14 also suppresses release of heat, and the temperature adjustment can be made easy. The above lower insulating means 13 and the insulating cover 14 has, when the holding block has the apparatus 51 for circulating the refrigerant, as described above, an effect for avoiding dew condensation.

Moreover, as the insulating cover 14 is provided so as to cover the surrounding of the holding block 11, release of heat from the holding block 11 to the measuring chamber 23 can be suppressed or prevented. As a result, similar to the lower insulating means 13, it is effective to suppress or prevent transfer of heat to the measuring chamber 23 or spectrophotometer. Accordingly, lowering of heating efficiency by the heater 15 can be avoided, and the load on the heater 15 can be lowered. Not only release of heat is prevented, but also effects of ambient atmosphere on the holding block 11 can be also prevented, and the temperature of the liquid sample 40 is prevented from being lower or unstable. When the holding block has the apparatus for circulating the refrigerant, since it is required to control the holder at low temperature, the insulating cover is very effective and useful.

By covering the surrounding of the holding block 11 by the insulating cover 14, heat release from the holding block 11 can be suppressed or prevented, and therefore the temperature of the holding block 11 can be controlled accurately by means of the heater 15, temperature sensor 16, and temperature controller 17. As a result, the temperature of the liquid sample 40 can be maintained constant.

Similarly for the holding block having the apparatus for circulating the refrigerant, by covering the surrounding of the holding block 11 by the insulating cover 14, external heat transmission to the holding block 11 in cooled condition can be prevented, and therefore the temperature of the holding block 11 can be controlled accurately by means of the heater 15, temperature sensor 16, and temperature controller 17. As a result, the temperature of the liquid sample 40 can be maintained at a specified low temperature. Moreover, it becomes possible to carry out the spectrum measurement under a condition of specific heating or cooling pattern by controlling with a program using an electric signal such as sensors. The sample holder for spectrum measurement of the invention may comprise the heating means and the apparatus 51 for circulating the refrigerant to keep at a low temperature condition of 10° C. or less concomitantly where necessary.

The heating means may be one to heat by providing a jacket at the periphery of the holding block 11 and circulating a heating medium such as silicone oil, Dowtherm oil or the like to the jacket by means of a heating medium circulating device. The heat medium may be circulated by using the same piping for the apparatus for circulating refrigerant. It may be such means that the heat medium is circulated by switching from the apparatus for circulating refrigerant.

The lower insulating unit 13 and insulating cover 14 are both the insulating means for suppressing or preventing heat release from the holding block 11, but as the configuration of the insulating means, for example, a plate or sheet member may be used for the lower insulating means 13. In stead of this configuration, a gap forming member maybe placed to keep a certain space between them between the holding block 11 and the light introducing path position adjusting means 12. As the material of the plate or sheet member, a heat-resistant resin may preferably be used. The heat-resistant resin preferably includes flouroresin, heat-resistant polypropylene, polyamide resin and the like. The material of the plate or sheet member may be a fiber reinforced resin.

The insulating means to be used as the lower insulating means 13 may be used by combining the plate or sheet member and the gap forming member. That is, by means of a fluororesin member, a certain space may be kept between the holding block 11 and the light introducing path position adjusting means 12. In this case, further, pores may be properly formed in the plate or sheet member, and nitrogen or other inert gas may be blown in, or a space may be formed by a double structure of plate or sheet members, and nitrogen or inert gas maybe blown into the space, so that the heat insulating effect may be further enhanced. The thickness of the above plate or sheet member is preferably about 3 to 50 mm. More preferably, it is 3 to 20 mm. Usually, the above insulating means can have an enough insulating effect with its thickness of about 10 mm when heat insulation between the holding block of the temperature of 200° C. and the light introducing path position adjusting means.

The lower insulating means 13 shown in FIG. 36 is a configuration in which a space is formed between fluororesin plates to improve the heat insulating effect. Inactive gas such as nitrogen or the like can be blown into such space for cooling. When the holding block has the apparatus for circulating the refrigerant, dew condensation can be prevented by injecting nitrogen gas or dried air into this space.

Regarding the lower insulating means, a configuration to form a space is preferably a structure in which a plate-shaped insulator is supported by a brace provided peripheral of the plate-shaped insulator. By using this structure, heat insulating and cooling effect of the heated holding block is enhanced so that heat is hardly be transferred to the light introducing path position adjusting means 12.

In the sample holder for spectrum measurement or spectrophotometer of the invention, as shown in FIG. 1(*b*), more preferably, a temperature measuring side hole 115 is formed to penetrate from the side of the holding block 11 toward a sample holding hole 111, and the temperature of the internal liquid sample 40 is directly measured by using a second temperature sensor 18 through this hole. The second temperature sensor 18 maybe used to merely measure the temperature of the liquid sample 40, but when it is connected to the temperature controller 17 so as to control the heating temperature of the heater 15, the liquid sample 40 can be heated at a more accurate temperature, hence it is preferable.

When the holding block has the apparatus for circulating the refrigerant, the second temperature sensor 18 may measure only the temperature of the liquid sample 40, but it is preferably connected to the temperature controller 17, similar to the temperature sensor 16, to adjust the solenoid valve for adjusting the circulation rate of the refrigerant, or to control the cooling water circulating apparatus 60 from the temperature controller 17 to adjust at a specific temperature.

In a mode of the sample holder of the invention, by inserting the temperature sensor 16 into the sample holding hole 111 not holding the sample container 30 (that is, the liquid sample 40), and measuring the temperature in the sample holding hole 111 (that is, the temperature of the holding block 11), it can be replaced with the temperature of the liquid sample 40. However, due to heat generation of the liquid sample 40 or the like, the temperature in the sample holding hole 111 may not always coincide with the temperature of the liquid sample 40. In this embodiment, accordingly, it is preferred to measure the temperature of the liquid sample 40 directly by forming the temperature measuring side hole 115.

There is a possibility of difference occurring between the heating temperature by the heater 15 or low temperature state by the refrigerant 50, and the temperature of the liquid sample 40, and as described below, when the chemical reaction of the liquid sample 40 is proceeding, in particular, a difference is likely to occur between the heating temperature and reaction temperature, or between the low temperature state and the reaction temperature. Accordingly, by using the second temperature sensor 18 and monitoring the temperature (reaction temperature, etc.) of the liquid sample 40 accurately, the temperature of the liquid sample 40 can be known accurately.

As the second temperature sensor 18 for measuring the temperature of the liquid sample 40 from the temperature measuring side hole 115, a structure capable of measuring the temperature of the liquid sample 40 without making contact is preferred, and such example includes an infrared sensor. In the sample holding hole 111, the liquid sample 40 is actually dispensed in the sample container 30, and it is difficult to measure the internal temperature by putting the temperature sensing element directly into the sample container 30. Accordingly, it is preferred to use a contact-free second temperature sensor 18 such as an infrared sensor. By measuring the temperature of the liquid sample 40 directly from the temperature measuring side hole 115, if the liquid sample 40 is undergoing a chemical reaction, the reaction temperature of the liquid sample 40 can be measured.

When heating the sample holder of the invention by heating means such as heater, the sample holder may be provided also with cooling means, aside from heating means. For example, the cooling means includes a structure of cooling the holding block 11 by using cooling water or other refrigerant (water cooling system), and a structure of cooling the holding block 11 by using a cooling fan (air cooling system). However, since the sample holder of the invention is limited in the space to be installed in the measuring chamber 23, this point must be taken into consideration as for the cooling means, too. For example, in an infrared spectrophotometer, the area of the measuring chamber 23 is about 20 cm×20 cm. Hence, if designed to be integrated with the sample holder, a water cooling system which can be made compact is relatively preferred, or if integrated with the spectrophotometer, air cooling type cooling means is provided in the measuring chamber 23.

The above cooling means can control the temperature of the liquid sample from room temperature to about 10° C., and it is separately described from the above apparatus for circulating the refrigerant to keep the liquid sample to the lower temperature of 10° C. or less.

When provided with such cooling means, it is possible to cool quickly if the holding block 11 is heated excessively by the heating means. Accordingly, the trouble of the temperature of the liquid sample 40 going out of the set temperature can be avoided, and the precision of temperature control can be enhanced. Depending on the liquid sample 40, it may be cooled, instead of being heated, during spectrum measurement, and it can be used in such application sufficiently. The holder for controlling at low temperature using the refrigerant may be also provided with heating means if necessary.

The spectrophotometer of the invention comprises such sample holder, but the species of the spectrum to be measured, that is, the type of the spectrophotometer is not particularly specified. In this embodiment, in particular, the infrared spectrophotometer for measuring near infrared or infrared spectrum, or the Raman spectrophotometer for measuring Raman spectrum may be preferably applied. Therefore, the light irradiating means 21 shown in FIG. 1(*a*) includes an infrared light source in the case of infrared spectrophotometer, or it includes various laser light source in the case of Raman spectrophotometer. Similarly, as for the light detecting means 22, optical sensor capable of detecting infrared ray may be provided in the case of infrared spectrophotometer, or optical sensor capable of detecting scattering light may be provided in the case of Raman spectrophotometer.

The light irradiating means 21 is preferred to comprise various optical systems for emitting the irradiation light from the light source to the liquid sample 40 in the holding block 11 via the light introducing path 112. Similarly, the light detecting means 22 is preferred to comprise various optical systems for introducing the irradiation light emitted from the liquid sample 40 in the holding block 11 to the optical sensor via the light introducing path 112. In the spectrophotometer of the invention, as far as the propagating route L of irradiation light can be formed along the light introducing path 112, it is not required that the light source, measuring chamber 23 and optical sensor should be always aligned straightly.

Regarding the sample holder for spectrum measurement of the invention, when the measurement spectrum is an infrared spectrum, the infrared spectrum transmitted from the liquid sample is to be measured; therefore, a configuration in which the light irradiating means 21 and the light detecting means 22 for the spectrum measurement are disposed linearly and opposingly is preferred. When the measurement spectrum is a Raman spectrum, the irradiation light for spectrum measurement is introduced into the liquid sample and then a scattering light irradiated from the liquid sample is detected by the light detecting means 22. Usually, the reflected scattering light is detected by the light detecting means provided together with the light irradiating means. The configuration in which the light detecting means 22 is disposed at an angle of 90 degrees relative to the light irradiating unit is also preferred.

When the Raman spectrum is measured, a configuration in which a Raman laser light detecting device provided together with a Raman laser light irradiating means is disposed at a position to block an exit of the light introducing path and the Raman spectrum is measured is a preferred configuration of the present invention.

In a measurement of spectrum by using the sample holder and spectrophotometer of the invention, while holding the liquid sample 40 stably in heated or cooled state, the spectrum can be measured instantly and in the time course. Therefore, preferably, it is possible to use a material mixture before synthesis of various organic compounds or polymers, that is a mixture of substances before progress of chemical reaction. Hence, for example, the spectrum can be measured in the time course in the process of synthesis of various organic compounds or polymers.

For example, in the synthesis of a polymer, solvent, monomer, catalyst and others are put into the sample container 30 to prepare a liquid sample 40, and it is heated or cooled in the sample holder depending on the condition of reaction. At this time, when the spectrum is measured in the time course, change from a pattern of a spectrum specific to monomer to a pattern of a spectrum specific to polymer can be measured in the time course. Similarly, in the synthesis of a compound, change from a pattern of a spectrum specific to a starting compound to a pattern of a spectrum specific to a produced compound can be measured in the time course. As a result, the mechanism of chemical reaction can be analyzed.

More specifically, as described in the exemplary embodiments below, for example, when the infrared spectrum of methyl acrylate monomer is measured, a peak of carbon-carbon double bond of vinyl group (C—H of C═C—H) is detected around 6100 $cm^{-1}$ to 6250 $cm^{-1}$. As polymerization of methyl acrylate is progressed, this peak decreases gradually. Accordingly, infrared spectra of known methyl polyacrylate and methyl acrylate monomer are measured preliminarily, and the speed of progress of the reaction can be analyzed according to the peak decrease on the basis of the prior measurement. Of course, there is a possibility of obtaining other findings from the peak changes, and the mechanism of polymerization reaction of methyl acrylate can be analyzed.

In the conventional spectrophotometer, it has been difficult to heat or cool (to very low temperature) the liquid sample 40 while measuring the spectrum, and hence time-course measurement of spectrum as mentioned above was usually difficult, but the invention allows to measure the spectrum while heating or cooling, so that the process of progress of chemical reaction can be analyzed by spectrum. Therefore, in the known chemical reaction, hitherto unknown findings can be obtained, and hence it can be effectively utilized in the research and development field of various compounds.

According to the invention, the liquid sample 40 is heated or cooled and held by the holding block 11. The irradiation light is emitted to the liquid sample 40 through the light introducing path 112. According to the embodiments and considering from the size of the measuring chamber 23, the tube having a small diameter may sometimes be used as the sample container 30 containing the liquid sample 40. In order to maintain such small sample container 30 stably in heated or cooled state, the size of the light introducing path 112 formed so as to intersect the sample holding hole 111 cannot be increased so much from the viewpoint of accurate control of temperature.

The invention comprises the light introducing path position adjusting means 12 in order that the irradiation light may reach accurately and securely up to such small irradiation target (the sample container 30 containing the liquid sample 40 and the light introducing path 112 leading thereto). By using this light introducing path position adjusting means 12, if the position of the holding block 11 is changed, the position of the light introducing path 112 relative to the propagating route L of irradiation light can be easily adjusted finely. Accordingly, the irradiation light emitted from the light irradiating means 21 can be securely introduced into the liquid sample 40 even when the diameter of the tube to be used is small and the irradiation target is small. In particular, owing to the adjusting means in the Z-direction, more accurate positioning is realized, and the irradiation light emitted from the light irradiating means 21 can be securely introduced into the liquid sample 40.

In this embodiment, in particular, the circular columnar holding block 11 having a plurality of sample holding holes 111 at equal distance from the center thereof as shown in FIG. 4 is preferably used. In such circular columnar holding block 11, by rotating it as mentioned above, spectra can be measured for four different liquid samples 40. However, along with the rotation of the holding block 11, the position of the light introducing path 112 may be deviated from the propagating route L of the irradiation light. To cope with this, by finely adjusting the position of the light introducing path 112 by the light introducing path position adjusting means 12, the irradiation light can be securely introduced into the liquid sample 40, and an accurate spectrum can be measured.

In the embodiment, as shown in FIG. 2, FIG. 3 and FIG. 5, it is preferred to use the light introducing path position adjusting means of X-Y-Z axis movable type (three-dimensional positioning type), which is the light introducing path position adjusting means 12 capable of adjusting the position in the X-direction along the propagating route L, Y-direction orthogonal to the X-direction, and Z-direction perpendicular to the X-direction and Y-direction. Accordingly, the irradiation light hits the liquid sample 40 securely by adjusting the distance or position between the liquid sample 40 and the exit position of irradiation light by the x-direction adjustment, and finely adjusting the relative distance or position of the light guide path 112 relative to the propagating route L by the Y-direction and Z-direction adjustment.

The using and setting method of in the sample holder for spectrum measurement of the invention is favorable to adjust the light introducing path 112 to the optical path by moving the light introducing path 112 in order to match light detecting sensitivity of the spectrophotometer by means of the light introducing path position adjusting means 12. And more favorably, to confirm that the near infrared light or infrared light is in the center of the optical path of the aluminum block, the sample holder of the X-Y-Z movable type is set in the sample chamber of the infrared spectrophotometer main body, and it is preferably adjusted so that the near infrared light or infrared light may be located in the center of the light introducing path 112 of the holding block by adjusting the light introducing path 112 to the optical path by moving the light introducing path 112 in order to match light detecting sensitivity of the spectrophotometer, while observing the intensity of the interferogram by the monitor of the infrared spectrophotometer and by way of the adjusting means in each direction of the light introducing path position adjusting means. In final fine adjustment, the highest sensitivity value (the value after setup) of the interferogram of the infrared spectrophotometer main body is adjusted to the center of the optical path.

Because the sample holder is needed to be such size that it is accommodated within the measuring chamber 23, as mentioned above, the sample container 30 to be used in the invention may sometimes be the tube having a small size of diameter to be suited to the sample holder size. Specifically, a small or thin tube such as a sampling tube for nuclear magnetic resonance (NMR) used in NMR spectroscopy can be used for sufficient measurement. The sampling tube for NMR is small or thin enough, and since it is manufactured for NMR measurement, it is free from any element having adverse effect on the spectrum measurement. The size of the sample container 30 is preferred to be settable into the hole 111. And it is preferred to be 10 mm or less in the diameter of the portion for irradiating the irradiation light for spectrum measurement, more preferably 5 mm or less. If the diameter of the portion for emitting the irradiation light for spectrum measurement exceeds 10 mm, spectrum measurement may sometimes be difficult, and it is not preferred. As the sample container 30, as far as the diameter of the portion for irradiating the irradiation light for spectrum measurement is within the specified range, it may also be the one in which only the portion for emitting the irradiation light for spectrum measurement is either thin or thick.

When an infrared light is used as the light for the spectrum measurement, excessively large diameter of the sample container sometimes cause such problem that a peak is saturated and becomes unclear or the infrared light is hard to be transmitted when the sample is discolored or polymerized and its transparency is decreased. Thus, the sample container preferably has a diameter of the portion for irradiating the irradiation light is 10 mm or less, more favorably, 5 mm or less. When a Raman light is used as the light for the spectrum measurement, a diameter of the sample container is not specifically limited since the scattering light is detected as the Raman spectrum; however, it is preferred to be 10 mm or less for the stable temperature control.

The above sample container may be any sample container as far as the liquid sample is held stably and includes, for example, a sample tube and it is preferably transparent and made from glass or quartz etc. The shape of the sample container includes tubular, stick-like, prismatic and the like. Preferably the shape is tubular.

Of course, the container used for containing the liquid sample 40 in the invention is not limited to a tubular container, but the tubular container is particularly preferred from the viewpoint of holding the container by forming a slot (sample holding hole 111) in the holding block 11. When it is a tubular container, the contact area between the inner wall of the sample holding hole 111 and the outer wall of the container can be increased, and it may be easy to hold stably, heat stably or keep at low temperature stably. When the conditions for spectrum measurement allows, the sample container may have other shape than tubular, such as prismatic and the like.

The disposed direction of the hole 111 for holding the liquid sample 40 may be any as far as the spectrum measurement is not obstructed; in the figures, the hole 111 is provided in a vertical direction to the horizontal plane and it may be provided in an oblique direction.

The liquid sample 40 can be also held by applying the same on a thin film holder component which having a region of transparency at the center of it. The thin film holder component is preferred to be a plate shape having a hole which allows the light for spectrum measurement to be passed.

The material for the thin film holder component includes aluminum, SUS, brass, copper and others, and aluminum, SUS and copper are preferred from the viewpoint of heating by heat conduction. The thickness of the thin film holder component is preferred to be 3 mm or less, or more preferably 1.5 mm or less.

In the thin film holder component, preferably, a transparent thin plate cell member for example a diamond cell or glass cell be mounted in the position where the liquid sample 40 is applied and the irradiation light for spectrum measurement is introduced from the light introducing path 112, for example, in the center of the thin film holder component. When the sample in liquid form is applied on the surface of the diamond cell, the sample 40 hardly reacts with the diamond cell or the glass cell and the diamond cell resists solvents (solvent resistant), hence the diamond cell is preferred. The diamond cell member is hardly damaged when scraping off or washed out after thermal polymerization or photocuring of the applied liquid sample because of its high surface hardness. When a material of the thin film holder component is SUS or the like, the polymerizable composition sometimes has a high adhesiveness to SUS or the like and the cured film adheres tightly to thin film holder component; however, by using the diamond cell to be set at the center of the thin film holder component, such polymerizable composition may be handled sufficiently. The diamond cell is preferably the one usually used in the prism or the like of infrared ray irradiation, and such cell has the absorption near 2000 $cm^{-1}$. The diamond cell is preferred to have a circular columnar shape, and the diameter of about 5 mm may be used. The thickness of 3 mm or less may be used. The liquid sample may be applied on the diamond cell surface and sandwiched between two diamond cells, and the diamond cells may be set to the thin film holder component and used. A glass thin plate cell may be used instead of the above diamond cell. It is easy to one-way use. It may be supported on the surface of the thin film holder component.

A potassium bromide (KBr) tablet may also be used instead of the above diamond cell. When the KBr tablet is used, the liquid sample can be applied on the surface of the KBr tablet and sandwiched between two KBr tablets, and these tablets can be set to the thin film holder component. KBr is low-cost and disposable. As the size of the KBr tablet, the diameter is preferably about 10 mm, and the thickness is preferably about 0.5 mm. The above KBr tablet is obtained by providing a predetermined pressure on KBr powder and molding into tablet-like shape. The spectrum may sometimes be difficult to transmit when the thickness of the tablet is too thick. The thickness of the KBr tablet and the pressure upon molding the tablet is controlled in order to enable sufficient spectrum measurement.

A plate-like material produced with a material having less inference to the spectrum measurement such as NaCl or KBr can be used as the thin film holder component. It is a plate-like material which is made from NaCl or KBr. In this case, too, the liquid sample may be applied on one piece of the plate-like material, or the liquid sample may be sandwiched between two pieces of plate-like materials, where necessary. A flame-like structure may be applied to the plate-like material and used.

The thin film holder component may be provided at any position where the light for spectrum measurement passes through when it is inserted in the holding block before a lower part thereof is cut out; and is preferred to be installed in the sector columnar gap formed in a way of the propagating route of the irradiation light. When the thin film holder component is used, the liquid sample is preferably used by applying the same on the surface of the thin film holder component and a configuration in which the transmitted spectrum is measured by feeding and emitting the irradiation light for spectrum measurement from the light introducing path 112 without placing the liquid sample 40 in the sample holding hole 111 to the liquid sample applied on the thin film holder component.

Figure 22:
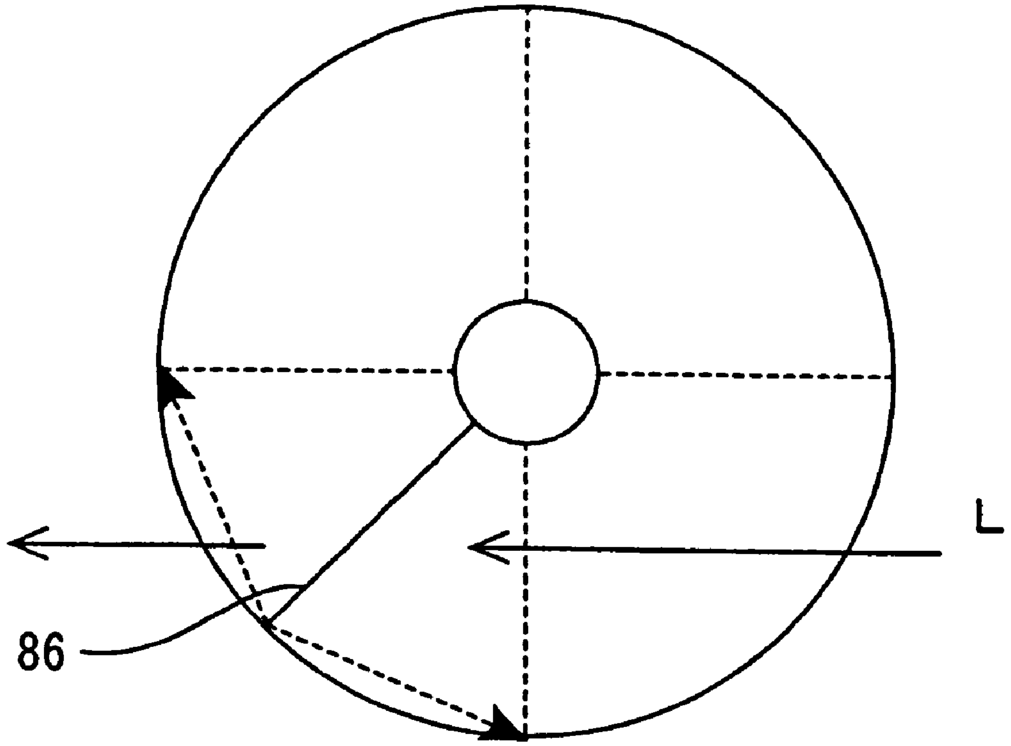
FIG. 22 is a plan view of sample holder for spectrum measurement of the invention as seen from above, showing the angle of the thin film holder component and the light for spectrum measurement.

The thin film holder component may be provided at the position of to decrease an interference (fringe) during the spectrum measurement. And is preferably the one an angle of the thin film holder component relative to the propagating route L of the irradiation light for spectrum measurement introduced from the light introducing path 112 is changeable. The thin film holder component may be detached in order to be disposed with a specific angle. The above angle is preferably between 0 to 90 degrees. More preferably, it is between 30 to 70 degrees and still more preferably, 45 to 60 degrees. By installing the thin film holder component as being changed of its angle, noise is extinct and the occurrence of a fringe phenomenon is avoided. FIG. 22 is a plan view of seeing the lower parts of holding block from the top when the thin film holder component is installed (the figure is a perspective plan). As shown in FIG. 22, a thin film holder component 86 can move in the direction of arrow indicated by dotted line in a range of 0 to 90 degrees, and is preferred to be adjusted to have a preferred angle relative to the light L for spectrum measurement in order to decrease the fringe phenomenon to a minimum extent. The occurrence of the fringe phenomenon may sometimes disturb the clear spectrum measurement.

In this case, it is a preferable configuration that the thin film holder is designed the size by adjusting the height of the gap and the height of the thin film holder component so as to the thin film holder component fits and is supported in the sector columnar gap, and then the thin film holder component is provided in the sector columnar gap. By providing the thin film holder component so as to be supported in the sector columnar gap, the above-mentioned angle adjustment and installation are rendered to be easy. Moreover, by providing, where necessary, a frame-like structure having a thickness of not less than the thickness of the thin film holder component itself peripheral of the thin film holder component, the thin film holder can be supported more stably in the sector columnar gap, and the angle can be adjusted more easily, whereby this is the preferable mode of the thin film holder component of the invention.

The above thin film holder component maybe a configuration to be installed in the holding block by providing an insertion hole at the predetermined site without cutting out a lower part of the holding block 11 to be provided with the light introducing path 112 as another arrangement. In this case, the insertion hole may be provided so as to the angle of the thin film holder component is constant relative to the propagating route L of the light for spectrum measurement.

More specifically of the above described another arrangement, it is preferable for the holding block of the present invention that, when the light introducing path 112 as the propagating route L of the light for spectrum measurement and the ray introducing path 116 as the propagating route M of the ray other than the light for spectrum measurement are provided, a thin film holder component inserting port in which the thin film holder component can be inserted is formed at a portion where the light introducing path 112 and the ray introducing path 116 are intersect. An angle of the above inserting port relative to the propagating route L is preferably 30 to 70 degrees. More preferably, it is 45 to 60 degrees. It may be 45 degrees in general. By providing the inserting port, an interference (fringe) during the spectrum measurement can be decreased.

Preferably, the sample holder for spectrum measurement of the invention has the configuration in which, as the irradiating means 6 of a ray other than the light for spectrum measurement, the ray or the electron beam irradiating means 6 of at least one species of ray or electron beam selected from a group consisting of electron beam, gamma-ray, laser beam, X-ray, ultraviolet ray, visible ray, and far infrared ray is externally provided to the sample holder for spectrum measurement. This configuration is explained by referring to FIG. 10 to FIG. 12. However, the invention is not limited to these embodiments.

Figure 10:
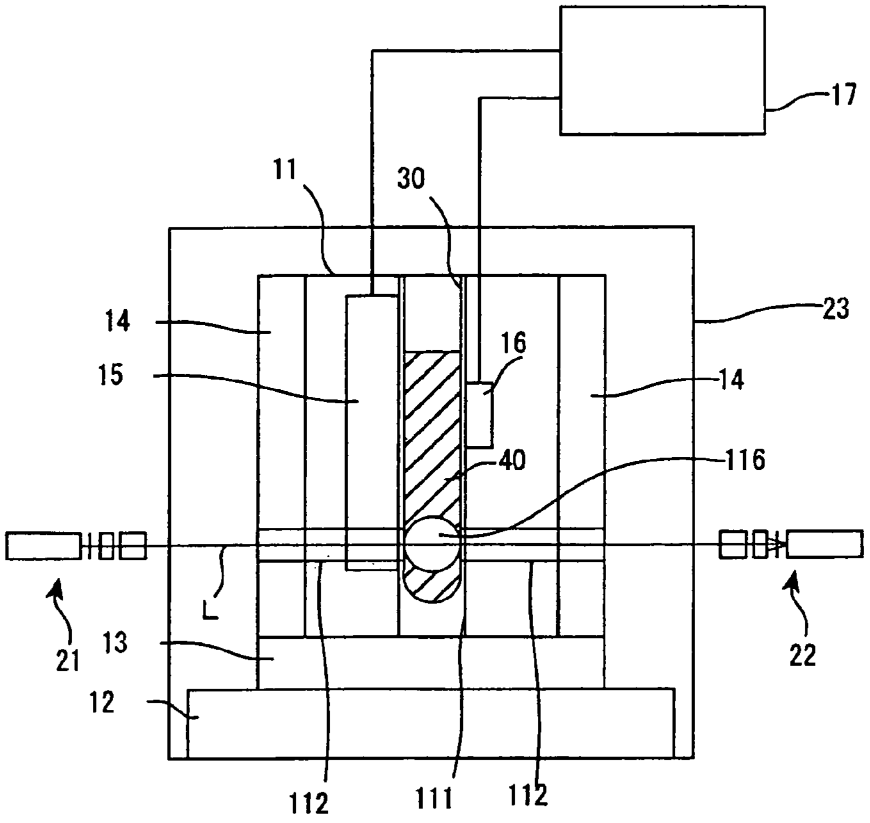
FIG. 10(*a*) is a schematic diagram of an example of configuration of the sample holder in an embodiment of the invention, and (b) is a perspective view showing an example of configuration of the holding block of the sample holder of (a) Aside from the light introducing path 112 for spectrum measurement, there is a ray introducing path 116 of the ray other than for spectrum measurement.
Figure 10:
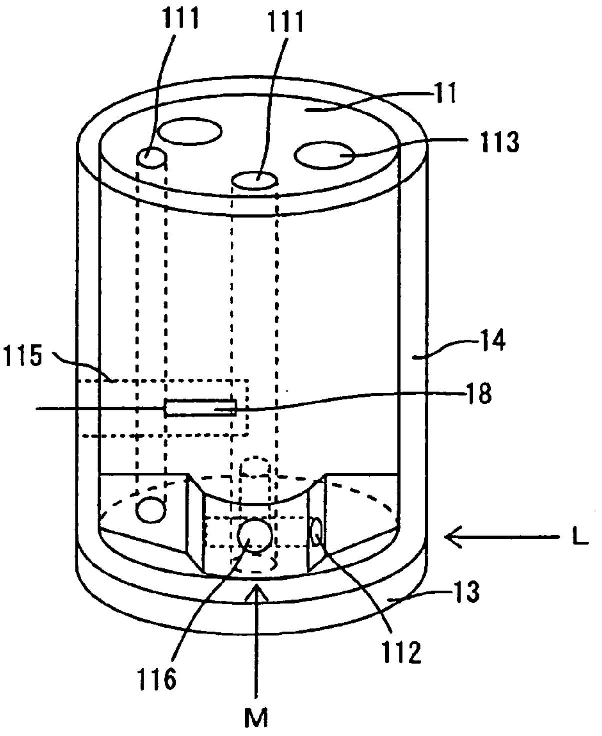

A specific example of the sample holder for spectrum measurement of the invention is schematically shown in FIG. 10 (a), which shows the sample holder for spectrum measurement comprising the columnar holding block 11 and the light introducing hole position adjusting mechanism (light introducing path position adjusting means) 12 provided under the holding block 11.

The sample holder for spectrum measurement may comprise, aside from the holding block 11 and light introducing path position adjusting means 12, further a lower insulating unit 13, an insulating cover 14, a heater 15, and a temperature sensor 16 as shown schematically in FIG. 10(*a*), (*b*). In addition, a ray introducing path 116 is disposed in order to introduce the ray other than the light for spectrum measurement, the light selected from gamma-ray, laser beam, X-ray, ultraviolet ray, visible ray, and far infrared ray, or the electromagnetic wave selected from microwave, radio wave, radio frequency, and electron beam from the irradiating means 6, to the liquid sample. Preferably, the ray introducing path 116 guiding the light or electromagnetic wave at wavelength of $10^{-16}$ to $10^{-6}$ cm, or $10^{-1}$ to $10^{10}$ cm is disposed aside from the light introducing path 112. More preferably, the ray introducing path 116 is disposed for introducing an ultraviolet ray into the liquid sample. Of course, other structure or member may be also disposed.

The size of the ray irradiating hole (ray introducing path) 116 may be enough to emit the light or electromagnetic wave other than for spectrum measurement to the liquid sample to be used, supposing the sample container (container for measurement) 30 containing the liquid sample 40 is a glass container of 5 mm in outside diameter and 15 mm in height. If the ray irradiating hole 116 is too small, the light or electron beam other than light for spectrum measurement irradiated to the liquid sample is not enough, and change behavior of liquid sample may not be measured accurately. Considering the size of the sample container for measurement, the size of the ray irradiating hole 116 is determined. For example, when the size of the sample container (container for measurement) 30 containing the liquid sample 40 is a glass container of 5 mm in outside diameter and 15 mm in height, the diameter of the ray irradiating hole 116 may be 5 mm.

The shape of the ray irradiating hole of the ray other than the light for spectrum measurement is not particularly specified as far as the light or electromagnetic wave for other than spectrum measurement is sufficiently emitted to the liquid sample, and it is preferred to be a slot from the viewpoint of ease of emission of light or electromagnetic wave other than for spectrum measurement to the entire sample.

The amount of the content indicated by broken line pattern of the sample container (container for measurement) 30 containing the liquid sample 40 in FIG. 10(*a*), and the size of the sample container (container for measurement) 30 may be determined in consideration of the size or feed volume of liquid sample, when measuring the change behavior of the liquid sample by light or electron beam by irradiating the ray or electron beam other than the light for spectrum measurement to the liquid sample. Specifically, depending on the size of the ray irradiating hole 116, the size of the sample container (container for measurement) 30 or the amount of the liquid sample should be determined so that the ray or electron beam may be sufficiently emitted to the entire liquid sample, which is a preferred embodiment of the invention. Specifically, the size of the light irradiating hole 116 is 0.6 times or more of the inside diameter of the sample container (container for measurement) 30, and more preferably 0.8 times or more, and most preferably 1 times or more of the diameter.

The amount of the liquid sample to be contained in the sample container (container for measurement) is preferred to be equivalent to a height of up to three times of the diameter of the light irradiating hole 116. More preferably, the height is up to 1.5 times. If the amount of the liquid sample is excessive, it may be difficult to measure accurately the change behavior by irradiation of ray or electron beam other than the light for spectrum measurement. When the sample container (container for measurement) 30 containing the liquid sample is viewed from the side, the side surface area calculated by the height from the bottom of the sample container (container for measurement) 30 of the liquid sample in the sample container (container for measurement) 30 containing the liquid sample is preferred to be three times or less of the effective inner surface area of the ray irradiating hole 116 other than the light for spectrum measurement. More preferably, it is two times or less. When the side surface area of the sample container (container for measurement) 30 filled with the liquid sample as calculated by the height from the bottom of the sample container (container for measurement) 30 of the liquid sample is the same as or less than the effective inner area of the ray irradiating hole 116 of the ray other than the light for spectrum measurement, the ray or electron beam other than the spectrum measurement light (infrared, near infrared, Raman light) of a sufficient amount is emitted to the liquid sample, which is a preferred embodiment in the invention.

The above sample holder for spectrum measurement is preferably a configuration in which the thin film holder component is installed in the sector columnar gap formed in a way of the propagating route of the irradiation light passing through the light introducing path 112 in the holding block 11 in a manner that the irradiation light for spectrum measurement transmits a film obtained by applying the liquid sample as a thin film, and further the ray or electron beam other than the light for spectrum measurement is introduced into the film applied on the thin film holder component from the irradiating means 6. The thin film holder component is the same as the one described above.

In a preferred embodiment of the spectrophotometer of the invention, as shown schematically in FIG. 10(*a*), a spectrum light irradiating means 21 and a spectrum light detecting means 22 disposed linearly in opposite configuration, and a measuring chamber 23 disposed between them are provided, and the above sample holder for spectrum measurement is disposed in the measuring chamber 23. As shown in FIG. 10(*a*), the spectrum light introducing path 112 provided in the sample holder for spectrum measurement is disposed in the position nearly coinciding with the propagating route L of the spectrum irradiation light, that is, at a position nearly coinciding with the linear route to reach the light detecting means 22 emitted from the spectrum light irradiating means 21.

In FIG. 10(*a*), by using the ray irradiating hole 116, the ray or electron beam other than the light for spectrum measurement light (infrared, near infrared, Raman light) is irradiated to the liquid sample, and it is in a relative position orthogonal to the propagating route L of the spectrum irradiation light provided in the sample holding block 11. The relative position or setting angle of the ray irradiating hole 116 for other than spectrum measurement and the propagating route L of the spectrum irradiation light is not particularly specified when using the liquid sample container having a circular columnar shape. It can be determined in consideration of the position of the sample holding hole 111 in the holding block 11 and the position of the hole for inserting the heater 15.

The holding block 11 is preferred to introduce the ray selected from gamma-ray, laser beam, X-ray, ultraviolet ray, visible ray, and far infrared ray, excluding the spectrum measuring light (infrared, near infrared, Raman light), or electromagnetic waves selected from microwave, radio wave, audio frequency, and electron beam, to the liquid sample, from the ray irradiating hole 116, in a state of stably holding the liquid sample 40 (that is, the sample container 30 containing the liquid sample 40) in the sample holding hole 111. It is more preferable to emit the ray or electromagnetic wave of a wavelength range of $10^{-16}$ to $10^{-6}$ cm, or $10^{-1}$ to $10^{10}$ cm from the ray irradiating hole 116 to the liquid sample. It is further preferred to emit an ultraviolet ray to the liquid sample. In the case of measuring the liquid sample of photocurable resin or photocurable monomer blended with photopolymerization initiator, since the photocurable resin or photocurable monomer is a compound having an unsaturated double bond responding to the ray in such wavelength, by emitting the ray other than the spectrum measuring light, extinction or change behavior of the unsaturated double bond such as vinyl group can be measured by the spectrum. The photopolymerization initiator may be a known agent. A proper photopolymerization initiator may be selected from the known agents depending on the characteristics of the photocurable resin or photocurable monomer.

Known photopolymerization initiators include, for example, azo photopolymerization initiators such as 2,2'-azobis (2-aminodinopropane), and the following examples. Specific examples include benzophenone, benzoin isobutyl ether, benzoin isopropyl ether, benzyl dimethyl ketal, 2,2-diethoxy acetophenone, 1-hydroxy cyclohexyl phenyl ketone, ethyl phenyl glioxylate, 2-chlorothioxanthone, 2,4-diisopropyl thioxane, 2,4,6-trimethyl benzoyl diphenoyl phosphine oxide, etc., and various onium salt type photopolymerization initiators can be also used. These exemplified compounds may be used either alone or in combination of two or more species, in consideration of the liquid sample to be measured or the measuring condition. Depending on the measuring condition, when measuring in the condition together with thermal radical polymerization initiator, it may be also used together with thermal radical polymerization initiator such as benzoyl peroxide (BPO) or methyl ethyl ketone peroxide.

In the present invention, it is also possible to heat or cool together with emission of ray or electron beam excluding the spectrum measuring light (infrared, near infrared, Raman light). In this case, the holding block 11 is designed to heat or cool the liquid sample 40 in the sample container 30 by heating the entire piece by the heater 15 or by cooling the entire piece by the apparatus for circulating the refrigerant while holding the liquid sample 40 (that is, the sample container 30 containing the liquid sample 40) stably in the sample holding hole 111. The material of the holding block is the same as those mentioned above.

The shape of the holding block 11 is not particularly specified, as far as it is designed to emit the spectrum irradiation light from the spectrum light irradiating means 21 securely and efficiently to the liquid sample 40 and detect the irradiation light from the liquid sample 40 securely and efficiently in the spectrum light detecting means 22. It is also preferred to be designed to emit the ray or electron beam excluding the spectrum measuring light (infrared, near infrared, Raman light) securely and efficiently to the liquid sample.

Also in the embodiment, as shown in FIG. 10(*b*), the holding block 11 having a circular columnar shape is preferably used. In this case, as shown in FIG. 10(*b*) and FIG. 11, the ray irradiating hole 116 of the ray other than the light for spectrum measurement is provided so that the ray or electron beam excluding the spectrum measuring light (infrared, near infrared, Raman light) may be emitted from the side of the holding block 11. A lateral slot is provided so that the ray or electron beam may pass to the opposite side of the holding block 11 relative to the ray irradiating hole 116 for other than spectrum measurement. The bottom of FIG. 10(*b*) shows its mode. The holding block 11 of the invention includes a transmission route for allowing the ray or electron beam excluding the spectrum measuring light (infrared, near infrared, Raman light) to pass through the liquid sample. For example, if there are four sample insertion holes 111, since the transmission route intersect on the diagonal lines, and the ray or electron beam excluding the spectrum measuring light may be emitted not only to one liquid sample, but also to plural liquid samples. In FIG. 10(*b*), there are two sample insertion holes. In the holding block 11 of the invention, it is preferred to design the angle and setting position of the lateral slots (light irradiating holes 116) of the holding block in order to keep the transmission route so that the ray or electron beam excluding the spectrum measuring light (infrared, near infrared, Raman light) may pass through the liquid sample.

Figure 11:
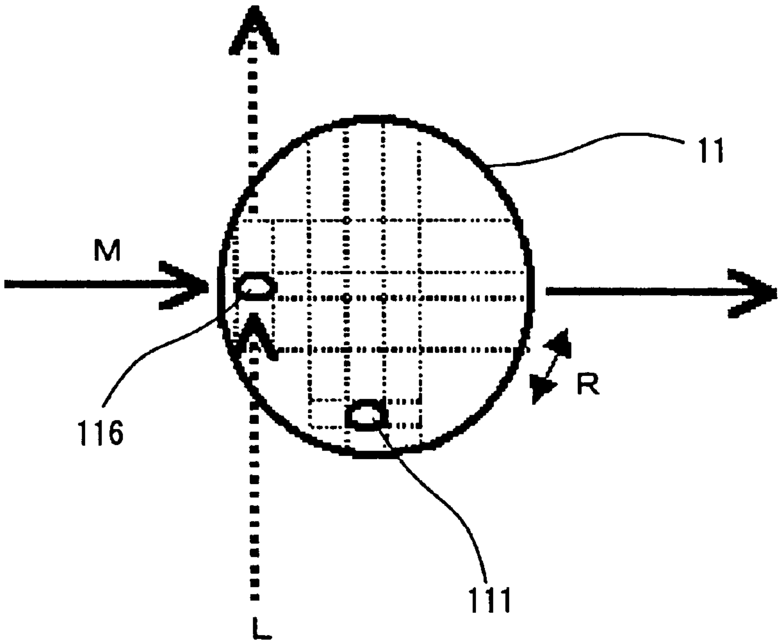
FIG. 11 is a plan view of the holding block seen from above.
Figure 12:
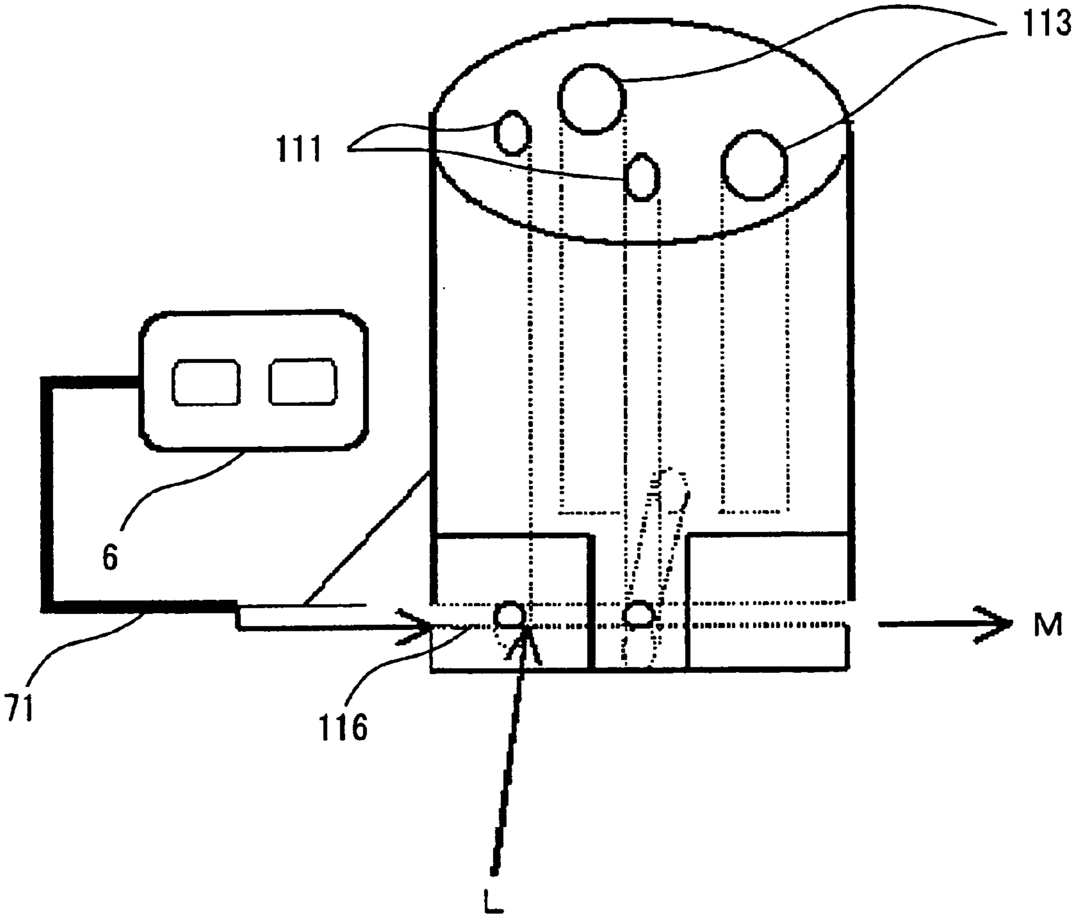
FIG. 12 is a diagram showing the relative positions of the sample holding hole 111 for holding a sample container of a liquid sample and a hole 113 for a heater to be equipped with the heater, showing a state that the ultraviolet ray is introduced into the liquid sample by way of an optical fiber sensor light from the ray irradiating device 6 of the ray other than the light for spectrum.

The light irradiating hole 116 preferably penetrates the holding block 11, as shown in FIG. 11 or FIG. 12. In this case, when the ray other than for spectrum measurement is introduced, the liquid sample may preferably not be provided in the sample holding hole 111 which intersects the ray irradiating hole 116. For example, the sample holder having 4 sample holding holes 111 preferably is not inserted with the liquid sample into the sample holding hole 111 provided at the opposite side on the diagonal line of the sample holding hole 111 holding the liquid sample to be measured.

The sample may be heated as required. In the measuring apparatus of the invention, when measuring the state change of the liquid sample changed by ultraviolet ray, usually it is measured at room temperature. It is also possible to measure while emitting the ultraviolet ray and heating. It is also possible to repeat ultraviolet irradiation and heating, or perform ultraviolet irradiation and heating intermittently at specific time setting, or perform ultraviolet irradiation and heating in arbitrary condition.

The liquid sample is preferred to contain a compound having an unsaturated double bond responding to light. By irradiating such liquid sample with the photo-energy (for example, irradiating with ultraviolet ray), the extinction or status change of unsaturated double bond such as vinyl group can be observed by means of the analytical technique of infrared, near infrared or Raman light. The sample holder or spectrophotometer of the invention can be preferably used as the instrument for carrying out such observation favorably. More specifically, the photopolymerization reaction or photochemical reaction initiated by irradiating the compound having an unsaturated double bond responding to light such as photocurable resin or photocurable monomer with photo-energy of ultraviolet ray or the like can be observed as the extinction or status change of the unsaturated double bond by the analytical technique of infrared, near infrared or Raman light, and thereby the reaction speed, reaction rate or reaction behavior of the compound having unsaturated double bond responding to light can be traced.

Herein, according to the invention, while irradiating the liquid sample 40 with ray or electromagnetic wave of specified wavelength for other than spectrum measurement, the liquid sample 40 can be held by the holding block 11, or being heated at the same time as required, but the irradiation ray or electromagnetic wave in the case of irradiation of the sample with the ray or electromagnetic wave in specified wavelength for other than spectrum measurement is emitted to the liquid sample 40 through the ray irradiating path 116 for other than spectrum measurement, aside from the light introducing path 112 for spectrum measurement. However, seeing from the size of the measuring chamber 23, the sample container 30 containing the liquid sample 40 is limited in size and in order to heat and hold such small sample container 30 stably, the size of the light introducing path 112 formed to intersect with the sample holding hole 111 is also limited. Similarly, it is hard to increase the size of the ray introducing path 116 for other than spectrum measurement. The location of installation of the ray irradiating path 116 for other than spectrum measurement should be selected properly at the light introducing path 116 so that the ray for other than spectrum measurement may be guided toward the outside of the sample holder or heating block by transmitting the liquid sample.

In the invention, the light introducing path position adjusting means 12 is provided in order that the irradiation light for spectrum measurement may reach accurately and securely up to the small irradiation target as mentioned above (the sample container 30 containing the liquid sample 40 and the light introducing path 112 for spectrum measurement reaching up thereto). By using the light introducing path position adjusting means 12, if the position of the holding block 11 is changed, the position of the light introducing path 112 relative to the propagating route L of the irradiation light can be easily adjusted finely. Accordingly, the irradiation light emitted from the light introducing means 21 can be securely introduced to the liquid sample 40. Moreover, in order to introduce the ray for other than spectrum measurement into the ray irradiating path 116 of the ray other than the light for spectrum measurement, a ray irradiating device (FIG. 12) is preferably provided outside of the sample holder as the means for emitting at least one species of ray or electron beam selected from electron beam, gamma-ray, laser beam, X-ray, ultraviolet ray, visible ray, and far infrared ray. The ray for other than spectrum measurement is preferred to be guided into the ray introducing path (ray irradiating hole) 116 of the ray other than that for spectrum measurement by using an optical fiber light sensor as shown in FIG. 12 and FIG. 18. If the position is slightly deviated because of using the optical fiber light sensor, sufficient ray or electromagnetic wave for changing the liquid sample can be guided.

In particular, for the sample holder for spectrum measurement of the invention, a circular columnar holding block 11 in which a plurality of sample holding holes 111 are formed at positions at equal distance from the center is preferably used. In such circular columnar holding block 11, as mentioned above, by rotating it horizontally, as an axis of the center of the holding block 11, the spectra can be measured from four different liquid samples 40. However, along with rotation of the holding block 11, the position of the light introducing path 112 relative to the propagating route L of the irradiation light may be deviated. To cope with this, by finely adjusting the position of the light introducing path 112 to the optical path by moving the light introducing path 112 in order to match light detecting sensitivity of the spectrophotometer by means of the light introducing path position adjusting means 12, the irradiation light can be securely guided into the liquid sample 40, and an accurate spectrum can be measured.

Figure 20:
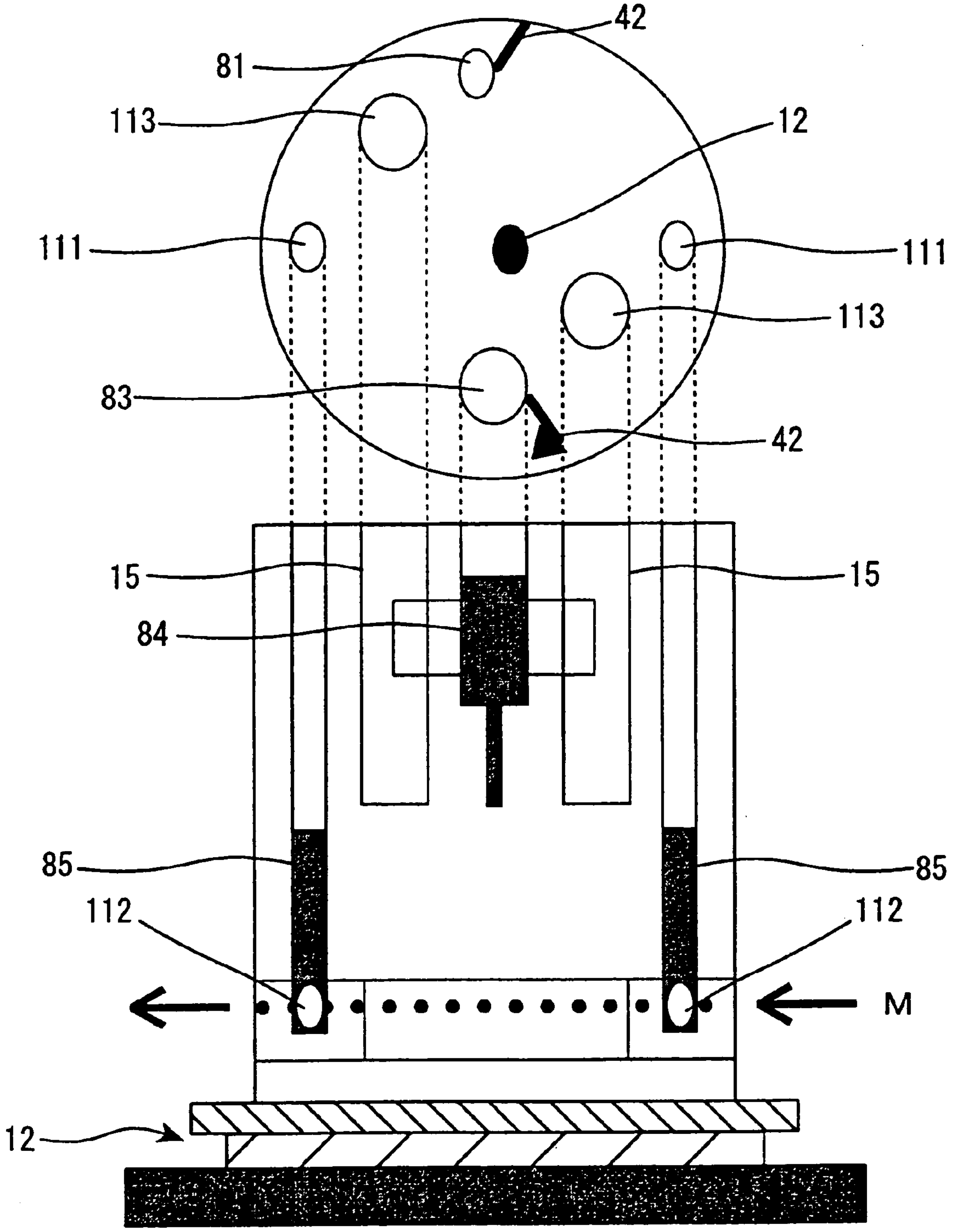
FIG. 20 is a diagram showing a preferred embodiment of the sample holder for spectrum measurement of the invention.
Figure 21:
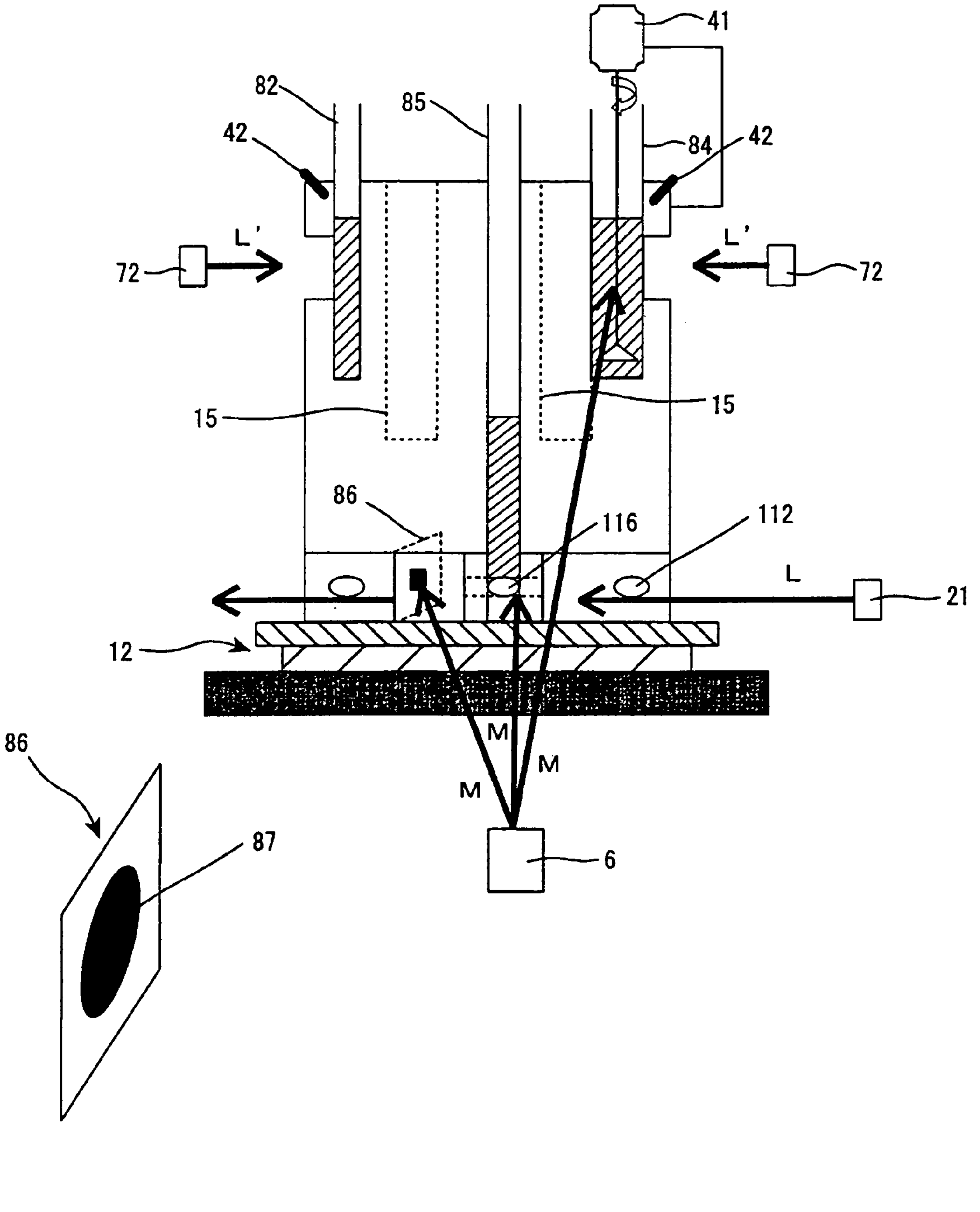
FIG. 21 shows a preferred embodiment of the sample holder for spectrum measurement of the invention in its top view, and its bottom view is a magnified diagram of the thin film holder component.

The sample holder for spectrum measurement of the invention can be used in a measurement using a laser light (also called Raman light) for Raman measurement as the light for spectrum measurement. FIGS. 19, 20 and 21 are preferred embodiments showing the use of Raman light as the light for spectrum measurement. In FIG. 19, laser light L' for Raman measurement is emitted to the liquid sample held in a Raman measurement sample container 84, and the scattering light is measured. The liquid sample held in the Raman measurement sample container may be heated by the heater 15 to initiate thermal polymerization, or ultraviolet curing or photocuring reaction may be induced by emitting ultraviolet ray or ray for other than spectrum measurement. By using the sample holder for spectrum measurement of the invention, a specific spectrum in thermal polymerization, photocuring or other reaction can be measured.

The Raman measurement sample container is preferred to be 10 mm or less in the diameter of the portion for emitting Raman light, or more preferably 5 mm or less. The Raman measurement sample container is preferred to be used together with a device for mixing the liquid sample supplied in the sample container. Such device for mixing the liquid sample is preferably an agitating device 41 or a stirring device 41, having an agitation or stirring motor as shown in FIG. 19. By installing the device for mixing the liquid sample, the liquid sample held in the sample container can be mixed evenly. The insertion hole for Raman measurement sample container may be provided at one or two or more positions per holding block.

Figure 31:
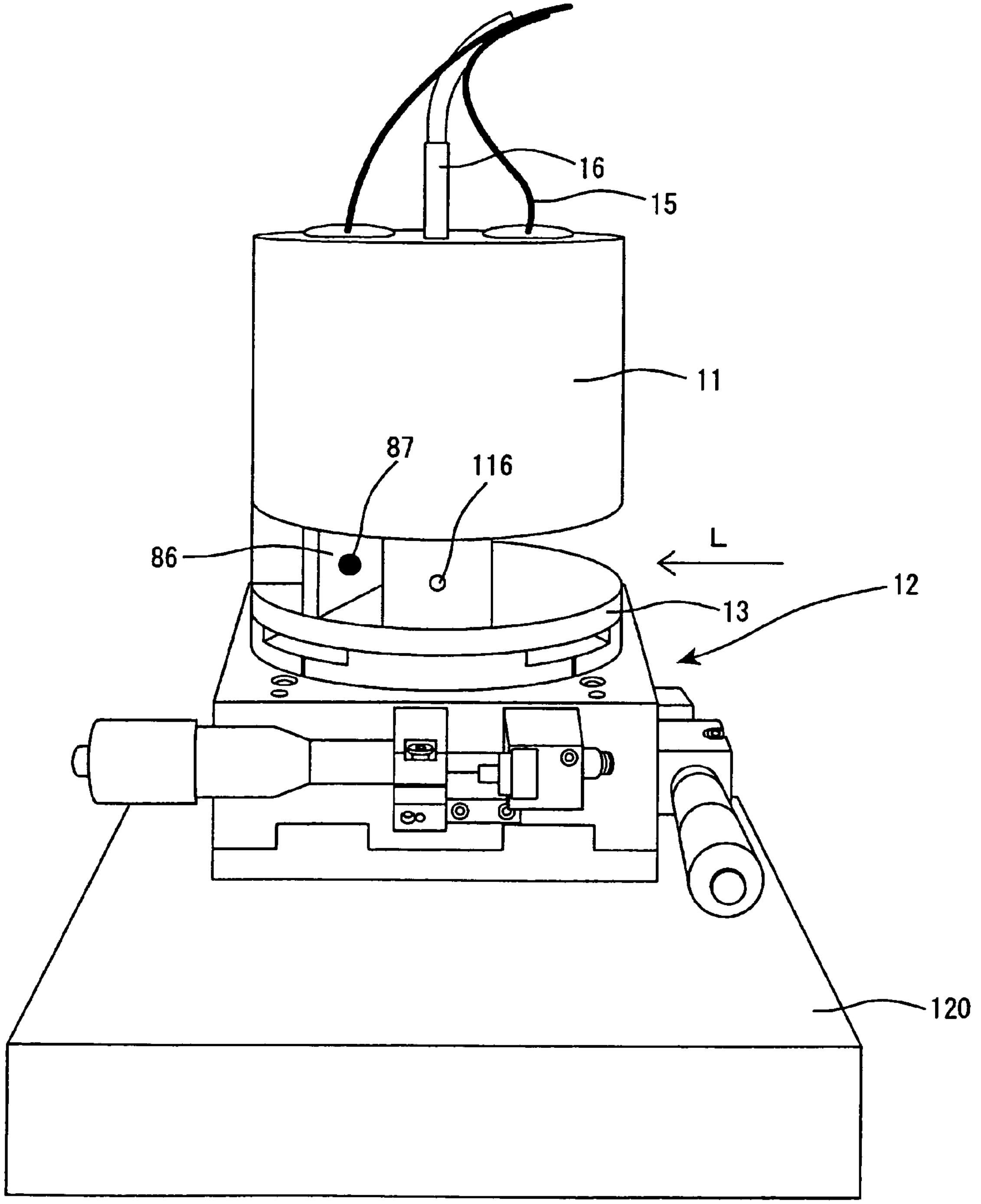
FIG. 31 is a diagram showing a mode of the sample holder for spectrum measurement provided with a thin film holder component.

The mode in FIG. 19 can measure by using a thin film holder component. In FIG. 19, the liquid sample is applied on a thin film holder component 86, and placed in a part of the lower part of the circular columnar bottom of the holding block 11 cut out in a sector columnar shape. In this mode, light M for other than spectrum measurement is emitted to the liquid sample and the liquid sample is cured optically, and light L for spectrum measurement is emitted to the liquid sample held on the thin film holder component through the light introducing path 112, so that the spectrum of the liquid sample can be measured. The liquid sample applied on transparent region of the thin film holder component is heated by the heater and polymerized thermally, and the spectrum of the liquid sample can be measured by introducing the light L for spectrum measurement from the light introducing path 112. In FIG. 31, ultraviolet ray or ray for other than spectrum measurement is preferred to be irradiated from the front side in the drawing.

The sample holder for spectrum measurement of the invention can measure by using Raman light and infrared light as the light for spectrum measurement. FIG. 20 shows a preferred mode of the sample holder for spectrum measurement when using Raman light and infrared light. In FIG. 20, as the light for spectrum measurement, for example, infrared light can be irradiated from the front side of the holding block, and guided into the liquid sample container 85 from the light introducing path 112, or Raman light can be emitted from the front side of the holding block to the Raman light introducing port 74 provided to the holding block 11 and guided into the Raman measurement sample container 82 or 84 held in the Raman measurement sample container holding hole 81 or the like. In this case, the ray M for other than spectrum measurement is irradiated to the Raman light introducing port 74 and introduced to the sample. Therefore, the ray is preferably irradiated from the side of the holding block as indicated by arrow. FIG. 20 shows a mode of combined use of Raman sample container 82 and 84. The Raman measurement sample container 84 and Raman sample container 82 may be same or different in the size of the portion for emitting Raman light. In FIG. 20, the Raman measurement sample container holding hole 81 is not shown, but the Raman measurement sample container 82 is inserted to the Raman measurement sample container sample holding hole 81. A nitrogen blow piping 42 for rotating the sample container is connected to the side of the Raman measurement sample container holding hole 81. By blowing nitrogen from the nitrogen blow piping 42 for rotating the sample container, the sample container floats and rotates. In such mode, the Raman light can be irradiated while rotating the Raman measurement sample container, and it is possible to measure favorably if the liquid sample is damaged by the laser beam. The nitrogen is preferably dry nitrogen gas. Gas used for rotating the sample container may be air or other gas, however, it is preferably dry nitrogen gas.

The diameter of the Raman measurement sample container 82 is preferably 5 to 10 mm, as same as the size of the container of the liquid sample, however, it may be, for example, 5 to 15 mm. The diameter of the Raman measurement sample holding hole 81 to which the Raman measurement sample container is inserted and held is preferably bigger than the diameter of the Raman measurement sample container 82 by approximately 1 mm. By providing a clearance of about 1 mm between the Raman measurement sample container 82 and the Raman measurement sample container holding hole 81 and blowing nitrogen or dry gas to the Raman measurement sample container holding hole 81 from an upper side direction by means of the nitrogen blow piping 42 for rotating sample container, swirl gas flow is generated periphery of the Raman measurement sample container 82 to thereby sufficiently float and rotate the Raman measurement sample container 82 in the Raman measurement sample container holding hole. Therefore, it is preferable for the holding block of the invention that it has an apparatus which can blow nitrogen or dry gas from upper side into the Raman measurement sample container holding hole 81. When the Raman spectrum is to be measured, the ray M other than the light for spectrum measurement may be introduced from the Raman light introducing port. The position, installing angle, and the amount of nitrogen flow maybe such that the sample container can float and rotate, and these can be selected appropriately. The mechanism for rotating and floating the sample container other than the one stated above may be employed. It is also possible to blow nitrogen or dry gas into the Raman measurement sample container holding hole 83 from the upper side direction by means of the nitrogen blow piping 42 for rotating sample container to thereby float and rotate the Raman measurement sample container 84.

FIG. 21 shows a preferred embodiment of the sample holder for spectrum measurement of the invention, thin film holder component, and diamond cell. In FIG. 21, the liquid sample may be in mode (1) to be held in the liquid sample container 85, light L for spectrum measurement being introduced from the light introducing path 112, and ray M for other than spectrum measurement being introduced from the ray introducing path 116 of the ray other than the light for spectrum measurement thereto, mode (2) to be applied on the thin film holder component 86, light L for spectrum measurement and/or ray M for other than spectrum measurement being irradiated, mode (3) to be held in the Raman sample container 84, Raman light L' and/or ray other than the light for spectrum measurement being irradiated, or mode (4) to be held in the Raman measurement sample container 82, Raman light L' being irradiated, and all of these modes may be employed, but when measuring by using the thin film holder component, it is preferred not to feed the liquid sample into the liquid sample container 85. In FIG. 21, the Raman measurement sample container 84 and Raman measurement sample container 82 are both provided with the agitating device and nitrogen blow piping for rotating the sample container, but one Raman measurement sample container may be provided with the agitating device and nitrogen blow piping for rotating the sample container. FIG. 21 shows the configuration in which the light introducing path 112 is located at a lower part of the holding block and the light introducing path for irradiating the Raman light L' is located in an upper part of the holding block, however, the light introducing path for irradiating the Raman light L' is one of configurations of the light introducing path 112 and the position of these light introducing paths on the holding block is not limited to the configuration in figures.

Thus, in the sample holder and spectrophotometer of the invention, by measuring the spectrum by holding the liquid sample 40, in particular, a mixture of substances before reaction, while heating, the spectrum can be measured in the process of reaction. As a result, in-situ spectrum measurement not known hitherto and analysis on the basis thereof are realized. Accordingly, in the known chemical reactions, hitherto unknown findings may be obtained, and this technology can be effectively utilized in research and development fields of various compounds.

Preferred embodiments of measuring method of Raman spectrum measurement and measuring method of infrared spectrum by using thin film holder component are described below while referring to FIG. 21.

<In-Situ Raman Measuring Method>

1) An in-situ attachment (sample holder for spectrum measurement of the invention) is installed in a measuring chamber of a Raman spectrum measuring apparatus.

2) Height and focus are adjusted by the light introducing path position adjusting means 12.

3) Liquid sample is poured into Raman measurement sample container 82 and Raman measurement sample container 84.

4) In the case of thermal polymerization reaction, the power source of the heater 15 is turned on to heat to a specified temperature.

5) In the case of photocuring reaction, the power source of a ray irradiating device 6 of the ray other than that for spectrum measurement is turned on, and ray for other than spectrum measurement (UV, EB, etc.) is emitted.

6) Laser beam is emitted from a laser light irradiating device 72 for Raman measurement, and the Raman spectrum before reaction is measured.

7) The motor of the agitating device 41 is turned on and the monomer synthesis reaction is carried out with agitation.

8) When heated to a specified temperature, or when irradiating the ray other than that for spectrum measurement, data is collected by multi-measurement.

9) Extinction or growth of the radical intended to observe, such as vinyl group, is traced by multi-measurement.

<In-Situ Thin Film Infrared Measuring Method>

1) An in-situ attachment (sample holder for spectrum measurement of the invention) is installed in a measuring chamber of an infrared spectrum measuring apparatus.

2) Adjusting the Z-axis and X-Y axis by the light introducing path position adjusting means 12, the infrared light is adjusted to come to the center of the light introducing path 112.

3) A thin film holder component alone is measured as a background.

4) A sample for measurement is sparingly applied and spread on the front of a thin film holder component 86.

5) An infrared sample container 85 is taken out.

6) In the case of thermal polymerization reaction, the power source of the heater 15 is turned on to heat to a specified temperature.

7) In the case of photocuring reaction, the power source of a ray emitting device 6 for other than spectrum measurement is turned on, and ray for other than spectrum measurement (UV, EB, etc.) is irradiated.

8) Infrared light is emitted from a light irradiating means 21, and the spectrum before reaction is measured.

9) When heated to a specified temperature, or when irradiating the ray other than that for spectrum measurement, data is collected by multi-measurement.

10) Extinction or growth of the radical intended to observe, such as vinyl group, is traced by multi-measurement.

Thus, in the sample holder for spectrum measurement and spectrophotometer of the invention, the sample holder comprises the light introducing path for introducing the irradiation light into the liquid sample, and the light introducing path is preferably formed at a position parallel to the propagating route of the irradiation light, and it further comprises the heating means for heating the liquid sample, and the light introducing path position adjusting means for changing the relative position of the light introducing path to the propagating route at least in one direction of the X-direction along the propagating route, Y-direction orthogonal to the X-direction, and Z-direction perpendicular to the X-direction and Y-direction. Since the sample holder for spectrum measurement comprises the light introducing path position adjusting means in the Z-direction, it can be easily applied in the spectrophotometers by various manufacturers.

Further, by adjusting by the light introducing path position adjusting means capable of changing the relative position of the light introducing path relative to the propagating route, with the sample holder installed in the measuring chamber but not containing the sample, in at least one direction of the X-direction along the propagating route, Y-direction orthogonal to the X-direction, and Z-direction perpendicular to the X-direction and Y-direction, confirmation of the light of the spectrophotometer being detected as passing through the center of the light introducing path, and confirmation of the sensitivity of the spectrophotometer and energy of the interferogram may be more secured.

In this configuration, while heating the liquid sample, the irradiation light emitted from the light irradiating means can be securely introduced into the liquid sample by the light introducing path and light introducing path position adjusting means. In particular, since the light introducing path position adjusting means is capable of adjusting the position of the light introducing path in at least one direction of the X-direction and Y-direction, and Z-direction perpendicular to the X-direction and Y-direction, a more accurate position adjustment can be realized. Accordingly, if the sample holder is removed and installed in a measuring chamber of other apparatus, the spectrum can be detected instantly and in the time course more securely from the liquid sample held stably in heated state.

Therefore, the sample holder for spectrum measurement of the invention is capable of guiding the irradiation light irradiated from the light irradiating means securely into the liquid sample, while heating the liquid sample, by the light introducing path and light introducing path position adjusting means. In particular, when the light introducing path position adjusting means is capable of adjusting the position of the light introducing path at least in one direction of the X-direction and Y-direction, and Z-direction vertical to the X-direction and Y-direction, a more accurate position adjustment is realized. Accordingly, the spectrum can be detected instantly and in the time course more securely from the liquid sample held stably in heated state.

As a result, spectrum measurement not known hitherto and analysis on the basis thereof are realized. Accordingly, in the known chemical reactions, hitherto unknown findings may be obtained, and this technology can be effectively utilized in research and development fields of various compounds.

By using the sample holder 31 for spectrum measurement of the invention and the spectrophotometer comprising this sample holder, the liquid sample can be controlled in low temperature state, in particular, in a very low temperature state, and various spectra can be analyzed in low temperature state or very low temperature state. Position adjustment is much easier because it further comprises the light introducing path horizontal direction position adjusting means 12-1 and/or the light introducing path vertical direction position adjusting means 12-2 for adjusting so that the liquid sample may be guided according to the propagating route of the irradiation light for spectrum measurement.

The sample holder for spectrum measurement and spectrophotometer of the invention further comprise the irradiating means of the ray or electron beam other than the light for spectrum measurement, and other ray introducing path capable of guiding the ray irradiated from the ray irradiating means into the liquid sample, aside from the light introducing path for introducing the irradiation light for spectrum measurement into the liquid sample, and since the light irradiating means is disposed at a position capable of irradiating the light emitted from the light irradiating means into the liquid sample, changes of the liquid sample can be detected by the spectrum while irradiating the liquid sample with ray or electromagnetic wave in specified wavelength, in addition to light for spectrum measurement. As a result, spectrum measurement of changes of state of the liquid sample by ray or electromagnetic wave in specified wavelength, which was difficult in the conventional measurement, and analysis on the basis thereof are realized. Accordingly, in the known chemical reactions, hitherto unknown findings may be obtained, and this technology can be effectively utilized in research and development fields of various compounds. Besides, by using the spectrum measuring apparatus comprising the sample holder for spectrum measurement of the invention, optical changing characteristics of novel photopolymerizable compound can be analyzed, and the development will be promoted. It may also comprise a device capable of heating or cooling as required, and spectra can be measured in varied conditions.

The spectrum measuring apparatus comprising the sample holder for spectrum measurement of the invention, the measuring method of spectrum of liquid sample by using the spectrum measuring apparatus comprising the sample holder for spectrum measurement of the invention, and the developing method of liquid sample by using the spectrum measuring apparatus comprising the sample holder for spectrum measurement of the invention are preferred embodiments. A quality management method of various photopolymerizable compounds to be manufactured (for example, the method of managing the products by measuring quality management data such as photopolymerization characteristic, photopolymerization speed, photopolymerization speed by ray of specific wavelength, or photosensitive performance by ray of specific wavelength) is also a preferred embodiment.

BEST MODE FOR CARRYING OUT THE INVENTION

The present invention is more specifically described below by way of the Examples. It must be noted, however, that the invention is not limited to these Examples alone.

SAMPLE HOLDER EXAMPLE 1

Using an infrared spectrophotometer (IR meter) comprising the sample holder of the invention, the infrared spectrum was measured on polymerization process of methyl acrylate.

The holding block was made of aluminum, in a circular columnar shape of 90 mm in diameter and 62 mm in height. The heater hole diameter was 20 mm, the sample holding hole diameter was 6 mm, the protrusion height of the cross bottom was 28 mm, and the light introducing path diameter was 4 mm. The lower insulating unit was made of fluororesin, and the insulating cover was made of aluminum. The sample container was an NMR sampling tube of 5 mm in diameter.

The heater output was 500 W, the temperature sensor was CA wire, and the temperature controller was heater controller of Tokyo Rikosha or microcontroller X model PTZ of Fuji Electric.

MEASUREMENT EXAMPLE 1

Figure 7:
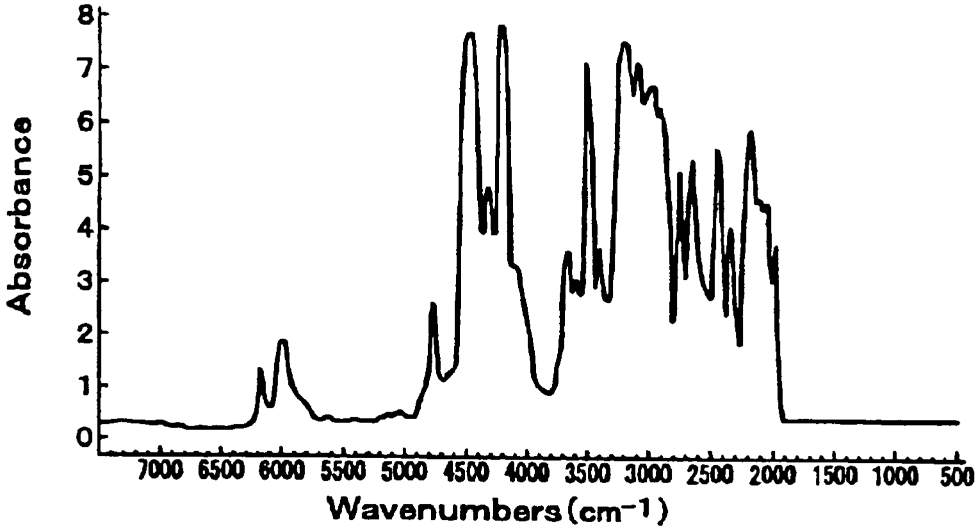
FIG. 7(*a*) is a chart showing infrared and near infrared absorption spectra of methyl acrylate used as sample of measurement in an embodiment of the invention, (b) is a graph showing time-course changes of absorption intensity of a peak of vinyl group specific to methyl acrylate obtained by using the sample holder and spectrophotometer of the invention, and (c) is a chart comparing the absorption spectrum of polymethyl acrylate and absorption spectrum of methyl acrylate monomer.
Figure 7:
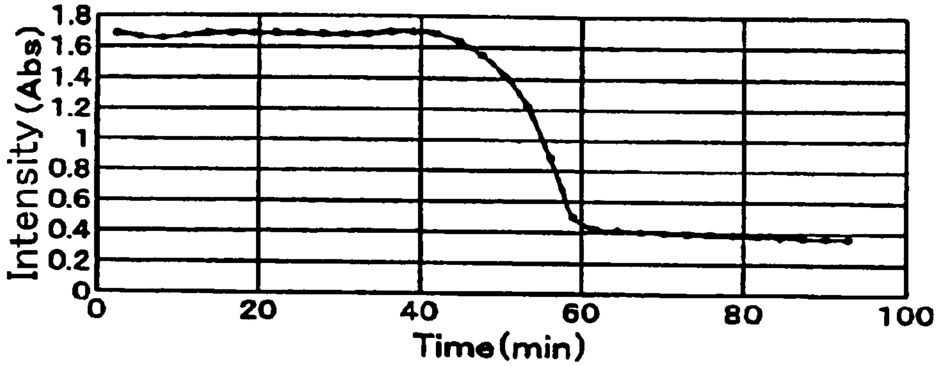
Figure 7:
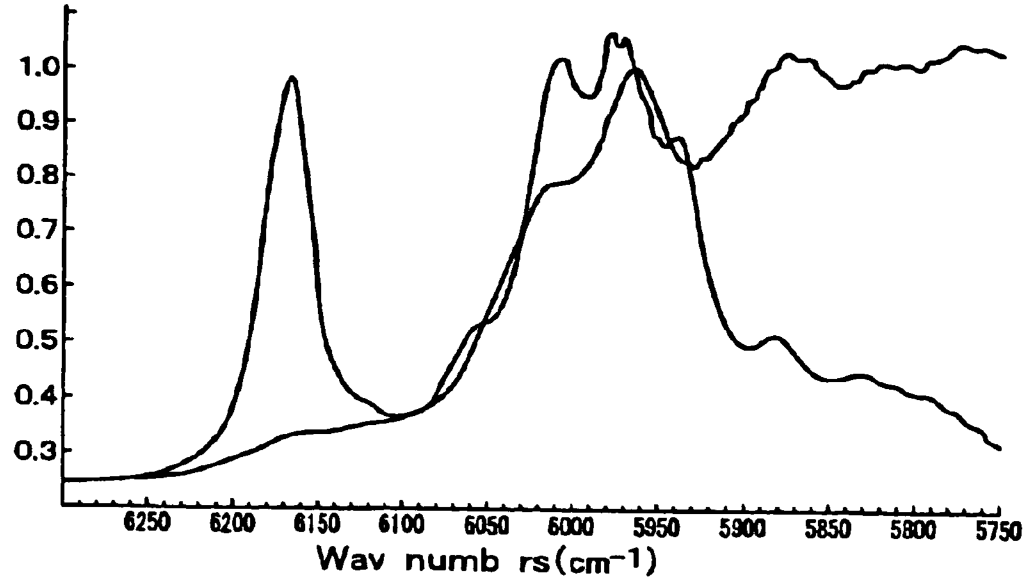

The infrared spectrum of methyl acrylate ($CH_2{=}CHCOOCH_3$) was measured. The result is shown in FIG. 7(*a*). In FIG. 7(*a*), the x-axis denotes the wave number (unit: $cm^{-1}$), and the y-axis represents the absorption intensity (unit: Abs). In this spectrum, being derived from the carbon-carbon double bond of vinyl group (C—H in C═C—H), an absorption peak of vinyl radical (hereinafter called vinyl peak) specific to methyl acrylate was observed around 6100 $cm^{-1}$ to 6250 $cm^{-1}$.

Afterwards, in 10 ml of methyl acrylate, 0.02 g of benzoyl peroxide was added, and by bubbling for 15 seconds in nitrogen, a liquid sample 40 for measurement was prepared. This liquid sample 40 was poured into the NMR sampling tube. On the other hand, the sample holder was placed in the measuring chamber of the IR meter, and the NMR sampling tube was set in the sample holding hole of this sample holder. Heating up to 70° C. by the heater, the infrared spectrum was measured in the time course by multiscanning. The measuring range of wave number was an overtone absorption range of C—H of 5800 $cm^{-1}$ to 6300 $cm^{-1}$, and the wave number for measuring the absorption intensity was 6170 $cm^{-1}$. The result is shown in the time course changing graph in FIG. 7(*b*). In FIG. 7(*b*), the x-axis is the time (unit: minutes) and the y-axis shows the absorption intensity of vinyl peak.

The liquid sample 40 before the reaction and liquid sample 40 after the reaction were compared in spectrum. The result is shown in FIG. 7(*c*). In FIG. 7(*c*), the x-axis denotes the wave number (unit: $cm^{-1}$) and the y-axis represents the absorption intensity (unit: Abs).

As clear from FIG. 7(*b*), by using the sample holder and IR meter conforming to the invention, it is known that the absorption intensity of the vinyl peak of methyl acrylate decreases along with progress of reaction. Hence, from this change of absorption intensity, the polymerization speed and other properties of methyl acrylate can be analyzed.

Also as shown in FIG. 7(*c*), the vinyl peak which was strong enough before the reaction was almost completely lost after the reaction. Thus, by using the absorption peak which is obviously changed before and after the reaction, the chemical reaction can be analyzed by infrared spectrum or near infrared spectrum. Same measurement was attempted in the infrared spectrophotometer of other manufacture than the infrared spectrophotometer used in this measurement example. Because the manufacturers were different, it was required to adjust the height of irradiation light (position adjustment in the Z-direction). However, the spectrum could be measured similarly, and it was found that the height of irradiation light (position adjustment in the Z-direction) can be adjusted easily even in the case of an infrared spectrophotometer of different manufacturers.

MEASUREMENT EXAMPLE 2

As a measurement example using the sample holder 31 for spectrum measurement having the holding block 11 provided with the apparatus 51 for circulating the refrigerant 50 to keep the liquid sample at low temperature of 10° C. or less, the behavior of polymerization of the polymer of ultra-high molecular weight of not less than 10,000,000 of weight-average molecular weight (Mw) was measured in the same manner as in the measurement example 1, except that the holder having the holding block as shown in FIG. 9 was used. As the apparatus for circulating the refrigerant, a cooling water circulating device was set at −5° C., the refrigerant was circulated, polymerization was started, and its behavior was observed. As a result, polymerization behavior of MMA at low temperature was observed. Ethylene glycol was used as the refrigerant.

Since the polymerization temperature of the polymer of butadiene or rubber is generally low, using the sample holder 31 for spectrum measurement having the holding block 11 provided with the apparatus 51 for circulating the refrigerant 50 to keep the liquid sample at low temperature of 10° C. or less, the polymerization behavior of the rubber polymer could be analyzed, and data for determining the polymerization condition and structural condition of rubber polymers of various structures could be obtained.

SAMPLE HOLDER EXAMPLE 2

Using an infrared spectrophotometer (IR meter) comprising the sample holder shown in FIG. 10, the infrared spectrum was measured on polymerization process of methyl acrylate.

The holding block was made of aluminum, in a circular columnar shape of 90 mm in diameter and 62 mm in height. The heater hole diameter was 20 mm, the sample holding hole diameter was 6 mm, the protrusion height of the cross bottom was 28 mm, and the light introducing path diameter for spectrum measurement was 4 mm. The lower insulating means was made of fluororesin, and the insulating cover was made of aluminum. The sample container was an NMR sampling tube of 5 mm in diameter. As the light emitting means 6 of the light other than that for spectrum measurement, LC5 UV spot light source LIGHTNING CURE of Hamamatsu Photonics was used. Using an optical fiber light sensor, an ultraviolet ray was irradiated to the liquid sample from a light irradiating path 116 of the light other than the light for spectrum measurement.

The heater output was 500 W, the temperature sensor was CA wire, and the temperature controller was heater controller of Tokyo Rikosha or microcontroller X model PTZ of Fuji Electric.

MEASUREMENT EXAMPLE 3

The infrared spectrum of methyl methacrylate ($CH_2$═C($CH_3$)—$COOCH_3$) was measured beforehand. The result is shown in FIG. 14.

Figure 13:
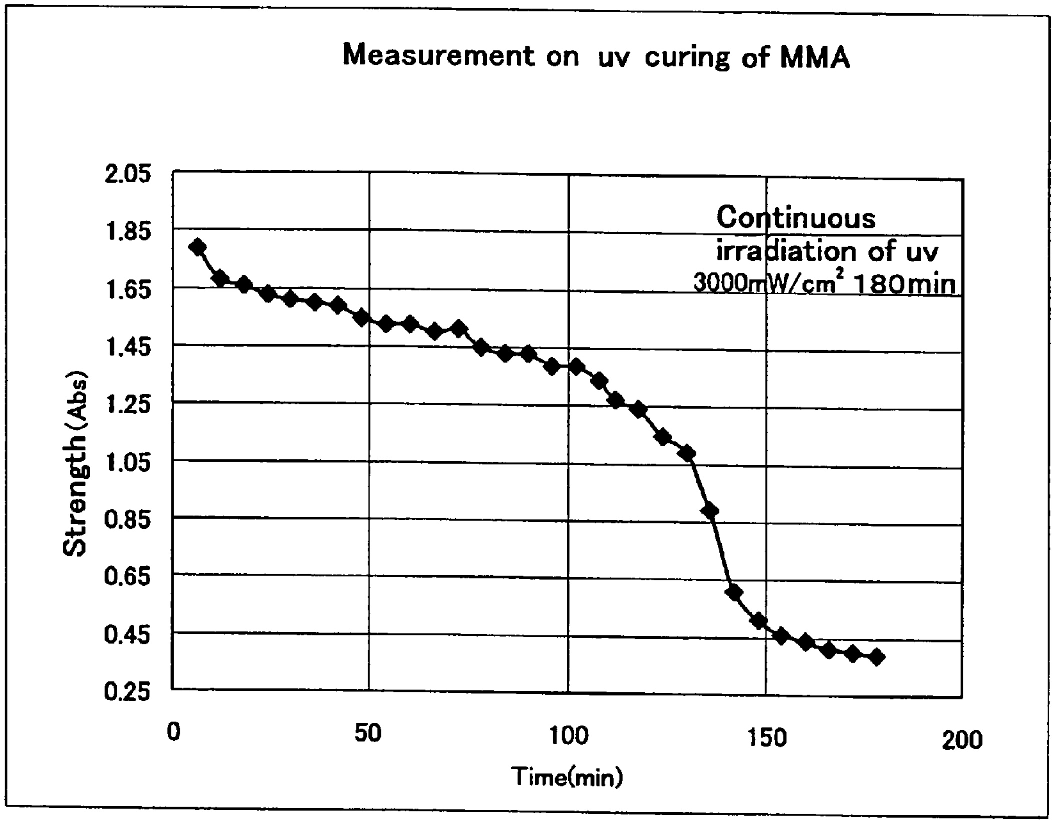
FIG. 13 is a graph showing changes of curing state of methyl methacrylate (MMA) by continuous irradiation of ultraviolet ray.

Afterwards, in 10 ml of methyl methacrylate, 5 g of solution of 2% methyl methacrylate of Darocure 1173 (Ciba Specialty Chemicals) was added, and by bubbling for 15 seconds in nitrogen, a liquid sample 40 for measurement was prepared. This liquid sample 40 was poured into the NMR sampling tube. On the other hand, the sample holder was placed in the measuring chamber of the IR meter, and the NMR sampling tube was set in the sample holding hole of this sample holder. An ultraviolet ray was emitted from the light irradiating device continuously for about 180 minutes at 3000 $mW/cm^2$, and the infrared spectrum was measured in the time course by multi-scanning. The measuring range of wave number was an overtone absorption range of C—H of 5800 $cm^{-1}$ to 6300 $cm^{-1}$, and the wave number for measuring the absorption intensity was 6170 $cm^{-1}$. The result is shown in the time course changing graph in FIG. 13. In FIG. 13, the x-axis is the time (unit: minutes) and the y-axis shows the absorption intensity of vinyl peak.

The liquid sample 40 before the reaction and liquid sample 40 after the reaction were compared in spectrum in the time course. The result is shown in FIG. 14. In FIG. 14, the x-axis denotes the wave number (unit: $cm^{-1}$) and the y-axis represents the absorption intensity (unit: Abs).

Figure 14:
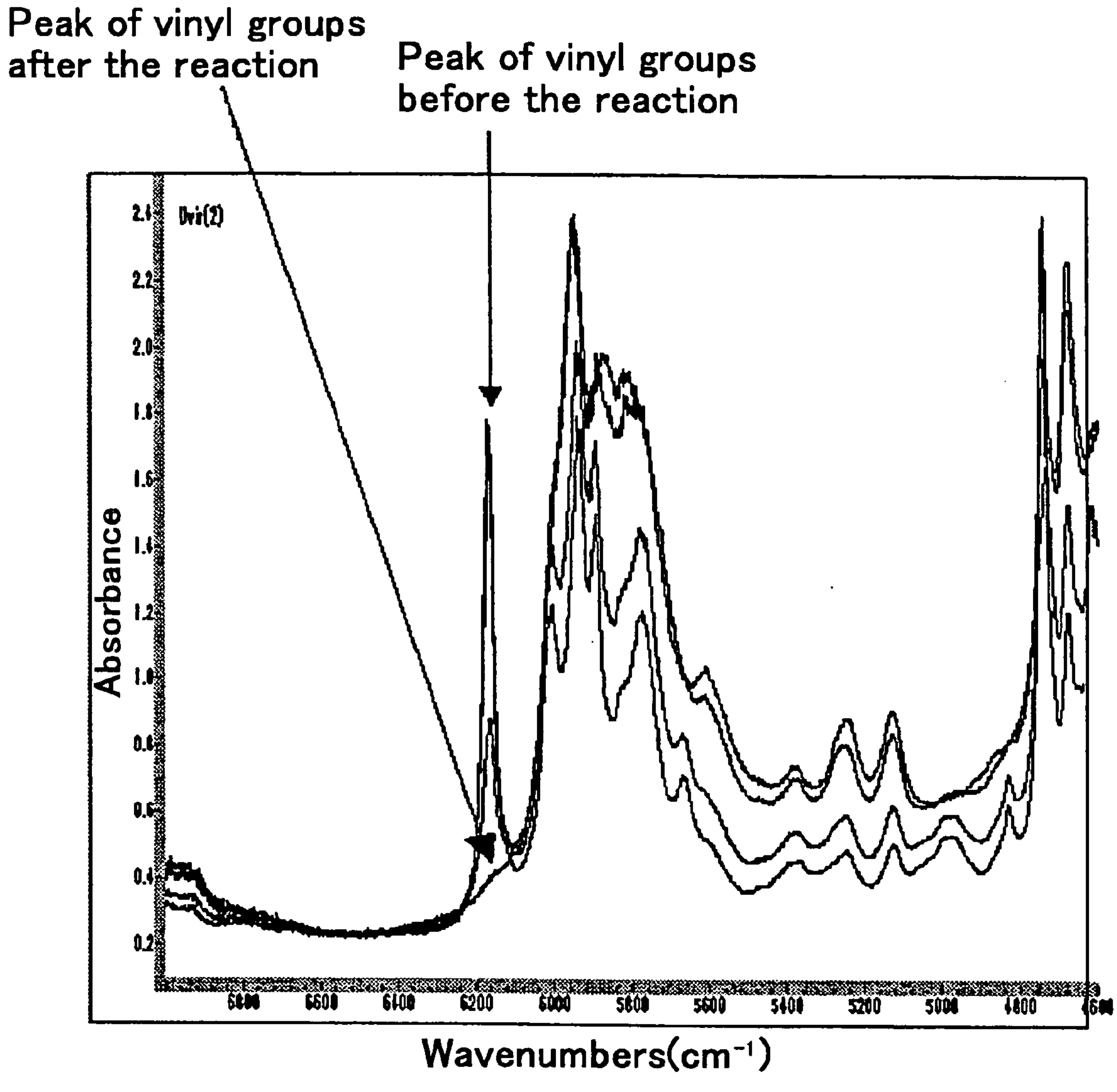
FIG. 14 is a chart showing infrared and near infrared absorption spectra of methyl methacrylate used as sample of measurement in an embodiment of the invention. This diagram shows time-course changes of absorption intensity of peak of vinyl group specific to methyl methacrylate, which is obtained by using the sample holder and spectrophotometer of the invention.

As clear from FIG. 13 and FIG. 14, by using the sample holder and IR meter conforming to the invention, it is known that the absorption intensity of the vinyl peak of methyl methacrylate due to irradiation with ultraviolet ray can be measured along with progress of reaction. Hence, from this change of absorption intensity, the polymerization speed and other properties of methyl methacrylate can be analyzed.

Also as shown in FIG. 14, the vinyl peak which was strong enough before the reaction was almost completely lost after the reaction. Thus, by using the absorption peak which is obviously changed before and after the reaction, the chemical reaction can be analyzed by infrared spectrum or near infrared spectrum.

One of measuring methods is introduced below.

(1) Mixing MMA/photopolymerization catalyst in a ratio of 13 g/1 g, the mixture is stirred in touch mixer for about 1 minute.

(2) About 0.5 ml of the sample (1) is taken, and put into an NMR tube of 5 mm in outside diameter, and this tube is set in the sample insertion hole of the light irradiating type attachment.

(3) The infrared spectrum of the sample before irradiation with light (UV) is measured, and this spectrum peak is obtained as the base spectrum peak.

(4) While emitting ultraviolet ray by using mercury xenon lamp, loss of vinyl group of MMA monomer is measured in real time by the infrared spectrophotometer. In a measurement example, for example, the measurement continued while emitting ultraviolet ray continuously for about 180 minutes.

The specification of the lamp for emitting ultraviolet ray was as follows.

Mercury xenon lamp (HPK: L67121)

Lamp power: 200 W

Condensing method: By elliptical reflective mirror

Light intensity adjustment: 0% to 100%

Ultraviolet ray emission intensity: Average 3500 mW/cm$^2$ (at 365 nm)

Irradiation time: 0.1 sec (100 mm/sec) or more; relay can be incorporated arbitrarily.

SAMPLE HOLDER EXAMPLE 3

Using the Raman spectrophotometer comprising the sample holder having the structure shown in FIG. 21, the process of thermal polymerization of in ethyl methacrylate (MMA) was measured by Raman spectrum.

The holding block was made of aluminum, in a circular columnar shape of 90 mm in diameter and 62 mm in height. The heater hole diameter was 20 mm, the sample holding hole diameter was 6 mm, the protrusion height of the cross bottom was 28 mm, and the light introducing path diameter for spectrum measurement was 4 mm. The lower insulating unit was made of fluororesin, and the insulating cover was made of aluminum.

The heater output was 500 W, the temperature sensor was CA wire, and the temperature controller was heater controller of Tokyo Rikosha or microcontroller X model PTZ of Fuji Electric.

MEASUREMENT EXAMPLE 4

Thermal Polymerization Reaction Measurement of MMA Monomer by In-Situ Raman Spectrum Measurement Methyl methacrylate (MMA), 10 ml, and benzoyl peroxide (BPO), 0.15 g, as a polymerization initiator were weighed. Mixing the weighed MMA and BPO, the mixture was bubbled for 15 seconds with nitrogen. The obtained liquid sample for measurement was put in a glass reaction tube of 50 mm in length and 5 mmϕ in diameter, and the nitrogen was blown in and the tube was closed. The sample holder of sample holder example 3 was set in the measuring chamber of the Raman spectrophotometer, and the glass reaction tube containing the liquid sample was put into the Raman measurement sample tube. By turning on the power source of the heater, the temperature was raised to 70° C. Nitrogen was blow in from the nitrogen blow piping for rotating the sample container, and the Raman measurement sample tube was rotated.

Figure 23:
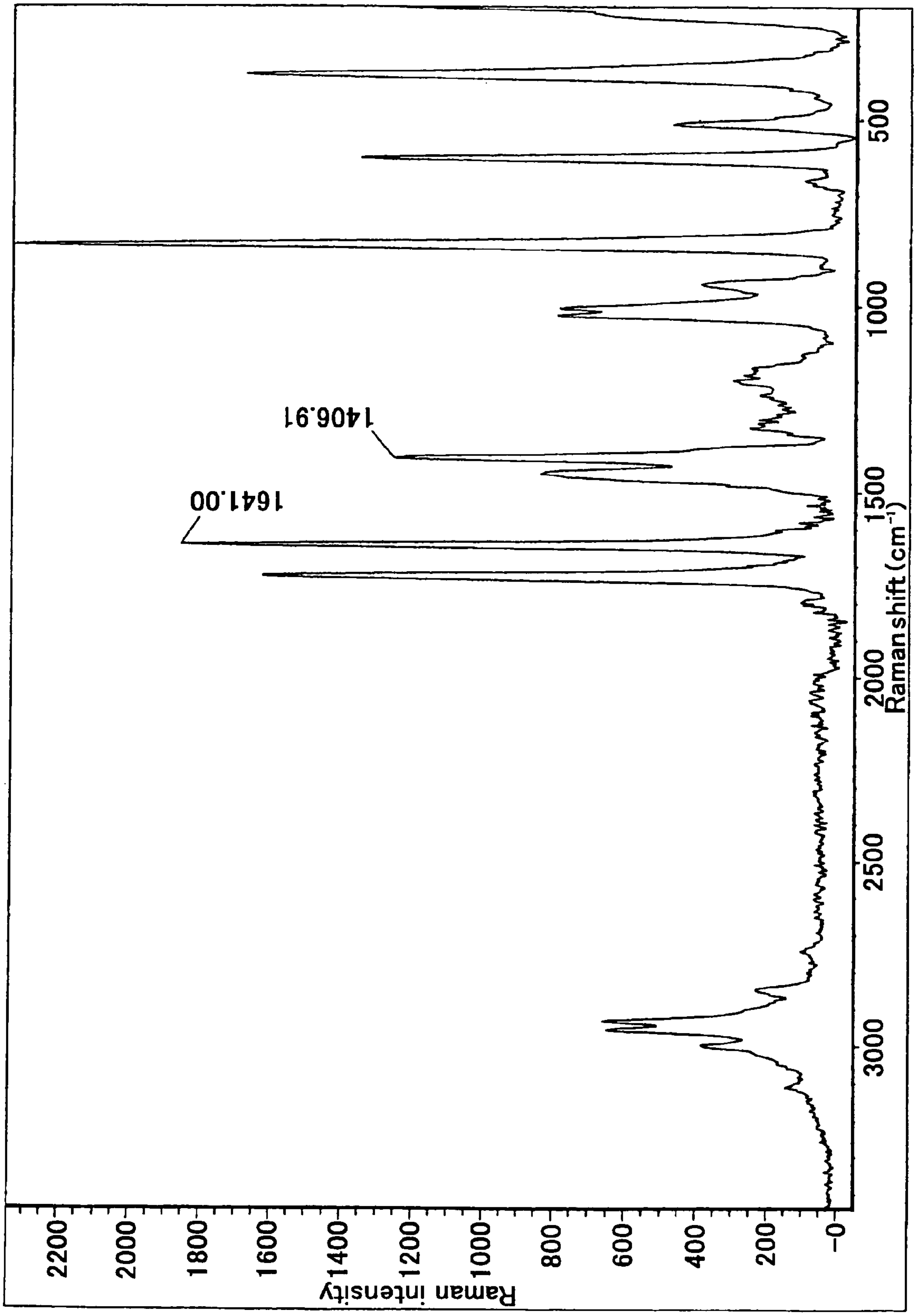
FIG. 23 is a graph showing Raman absorption before thermal polymerization of methyl methacrylate (MMA).
Figure 24:
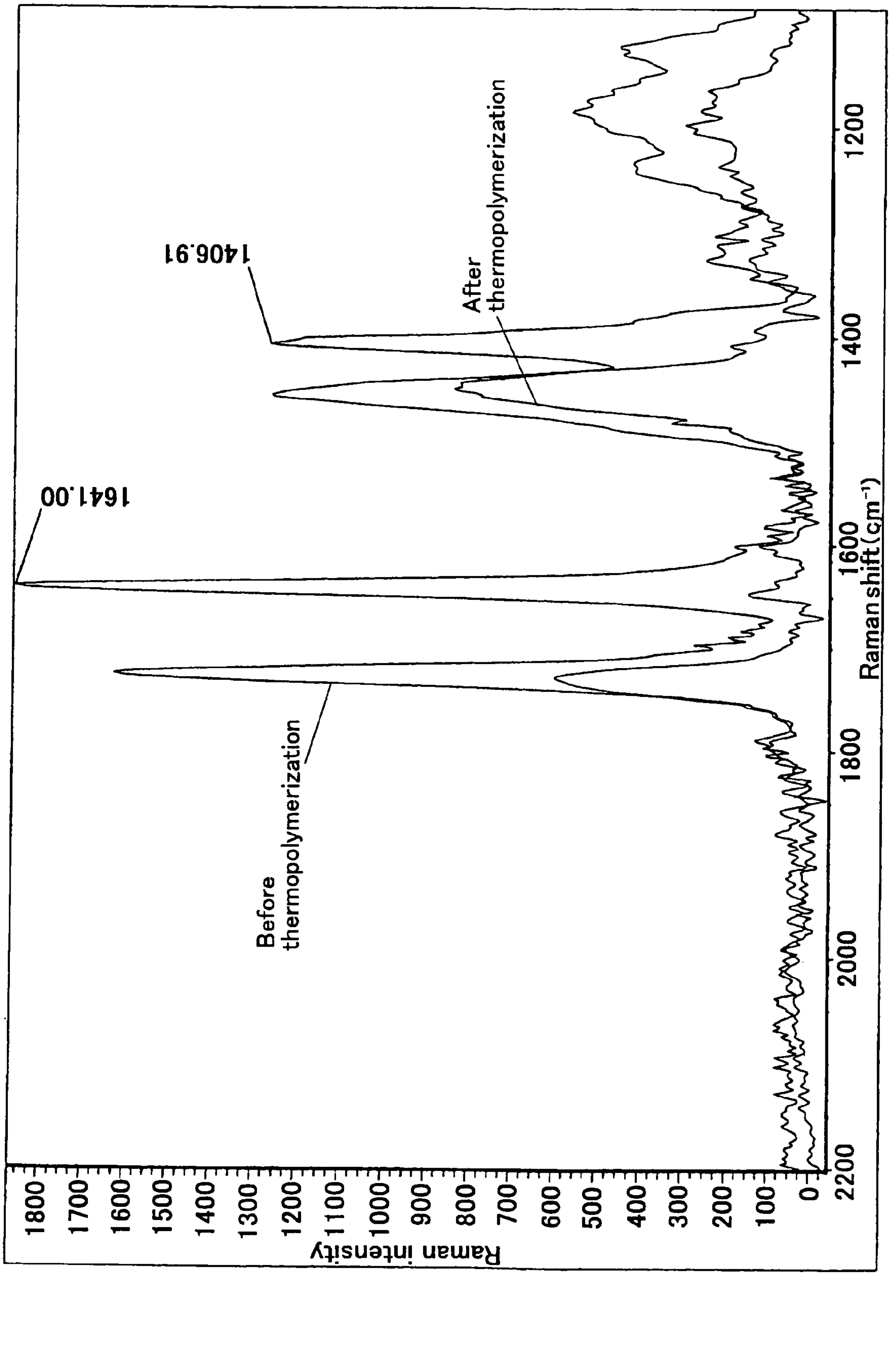
FIG. 24 is a graph showing Raman absorption spectra before thermal polymerization and after thermal polymerization of MMA.
Figure 25:
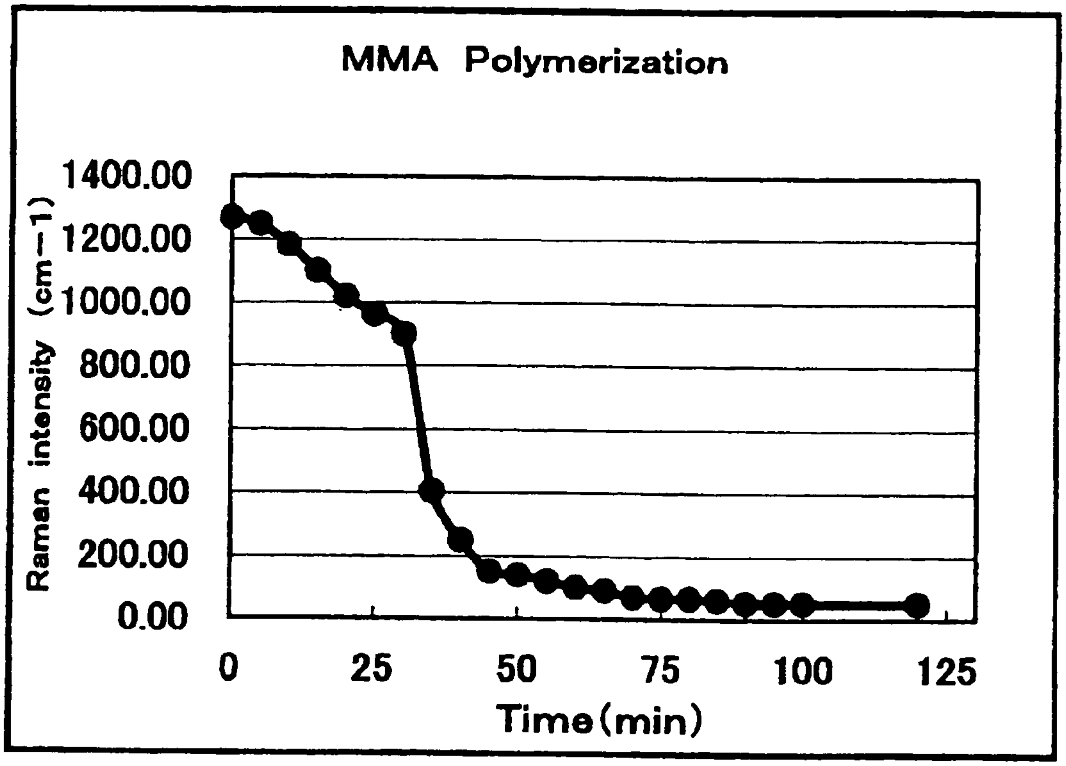
FIG. 25 is a graph showing time-course changes of Raman intensity at 1406 $cm^{-1}$ in thermal polymerization of MMA.
Figure 26:
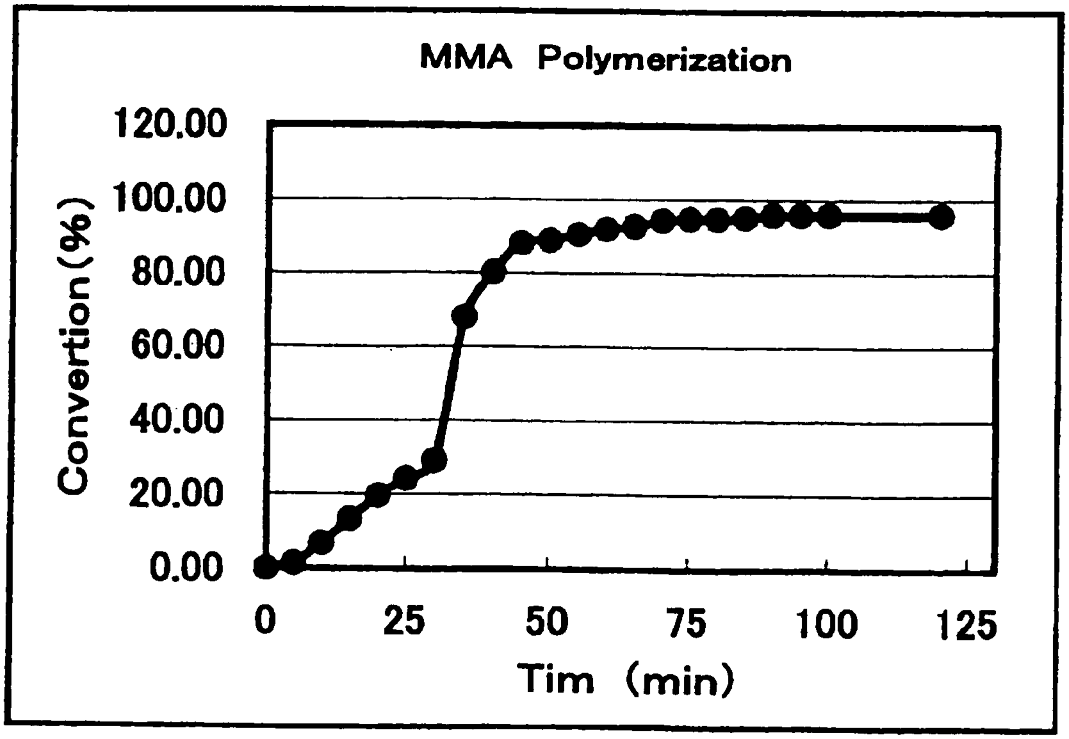
FIG. 26 is a graph showing the reactivity calculated from the Raman intensity at 1406 $cm^{-1}$ in thermal polymerization of MMA.

By emitting a laser light from laser light irradiating device for Raman measurement, the Raman spectrum of the sample before the reaction was measured. The result is shown in FIG. 23. As shown in FIG. 23, the Raman absorption spectrum before thermal polymerization reaction shows Raman absorption of carbon-carbon double bond of MMA ($—C(CH_3)═CH_2$) at 1406 cm$^{-1}$ and 1641 cm$^{-1}$. Raman spectra before and after thermal polymerization are shown in FIG. 24. As the thermal polymerization reaction progresses, the absorption at 1406 cm$^{-1}$ and 1641 cm$^{-1}$ was lost. Tracing the loss of absorption at 1406 cm$^{-1}$, the reaction behavior and reaction rate were measured. The results are shown in FIG. 25 and FIG. 26.

The structure of MMA and poly(methylmethacrylate) (PMMA) obtained in thermal polymerization is shown below.

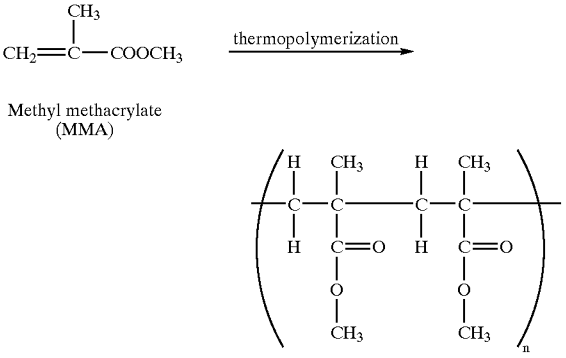

Methyl methacrylate (MMA)

Poly (methyl methacrylate) (PMMA)

MEASUREMENT EXAMPLE 5

Figure 27:
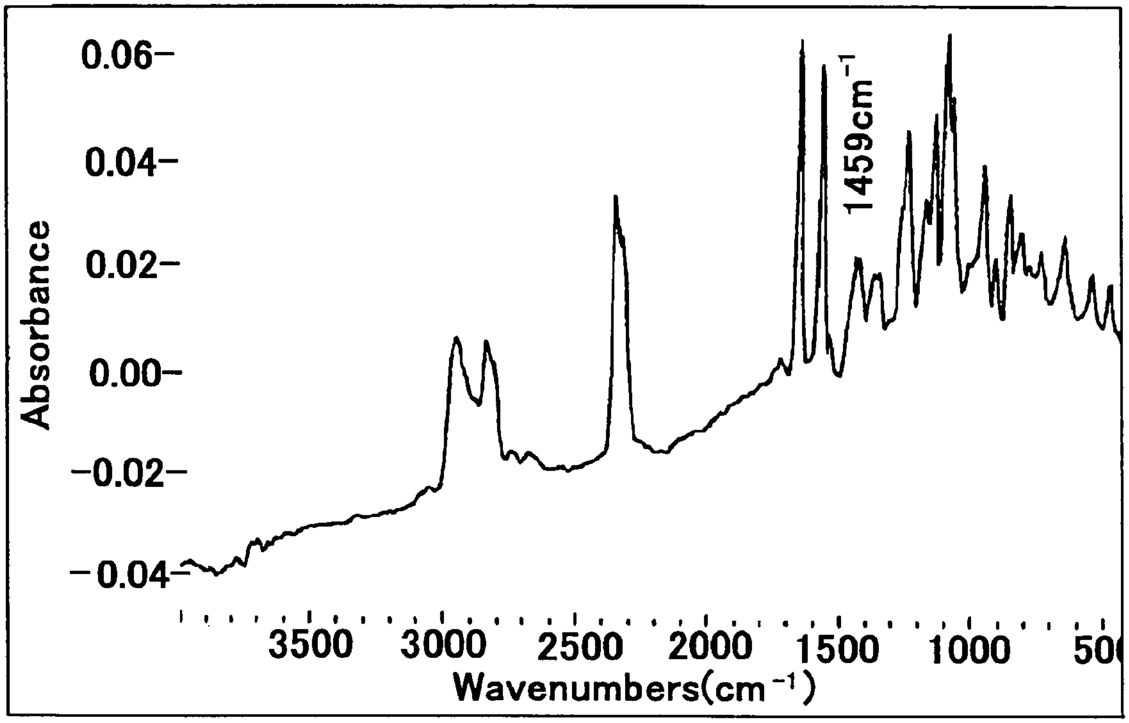
FIG. 27 is a graph showing infrared absorption before ultraviolet (UV) curing of MMA.

UV Curing Reaction Measurement of MMA Monomer by In-Situ Infrared (IR) Measurement Methyl methacrylate (MMA), 1 mole, and Irga Cure 907 (Ciba Specialty Chemicals), 0.1 mole, as a photopolymerization initiator were mixed and stirred well to obtain a liquid sample for measurement. An aluminum thin film holder component having a diamond cell in the central part was set in the cross bottom of the sample holder of sample holder example 3, and it was placed in the measuring chamber of the infrared spectrophotometer (IR meter). By adjusting the X-axis, Y-axis, and Z-axis by the light introducing path position adjusting means, the infrared ray was adjusted to be irradiated to the center of the diamond cell. Emitting an infrared ray, the IR spectrum was measured with the diamond cell only, which was obtained as the background. The liquid sample was sparingly applied on the surface of the diamond cell of the thin film holder component, and it was set in the sample holder. Without UV irradiation, an infrared ray was emitted, and the infrared spectrum of the sample before UV curing reaction was measured. The result is shown in FIG. 27. As shown in FIG. 27, in the infrared absorption spectrum before UV curing reaction, an IR absorption of carbon-carbon double bond of MMA (—$C(CH_3)=CH_2$) was confirmed at 1459 $cm^{-1}$.

Figure 28:
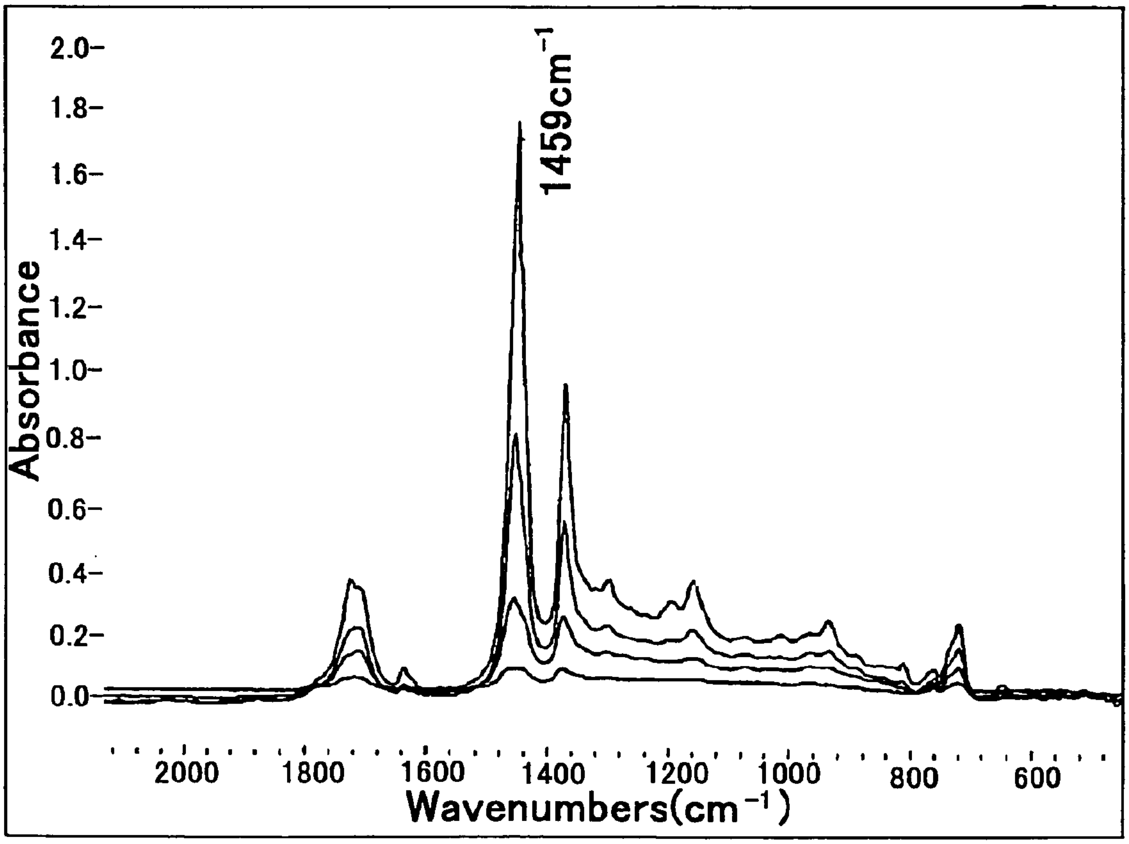
FIG. 28 is a graph showing time-course changes of infrared absorption in UV curing of MMA.
Figure 29:
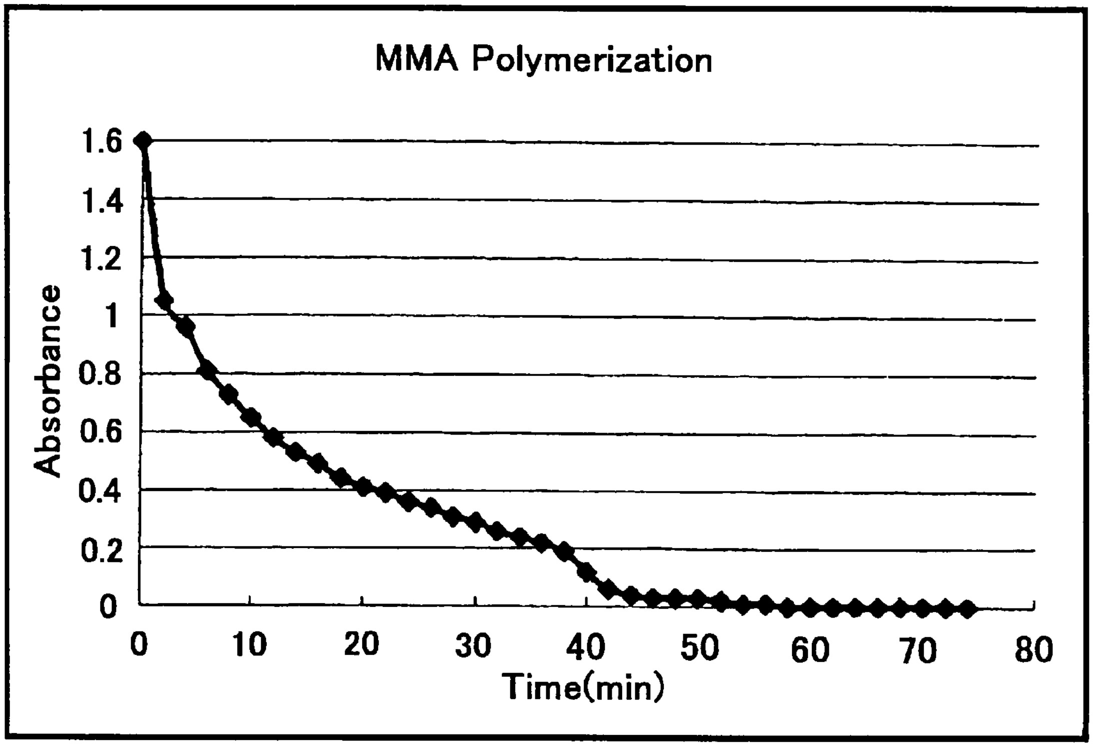
FIG. 29 is a graph showing time-course changes of infrared absorption at 1459 $cm^{-1}$ in UV curing of MMA.
Figure 30:
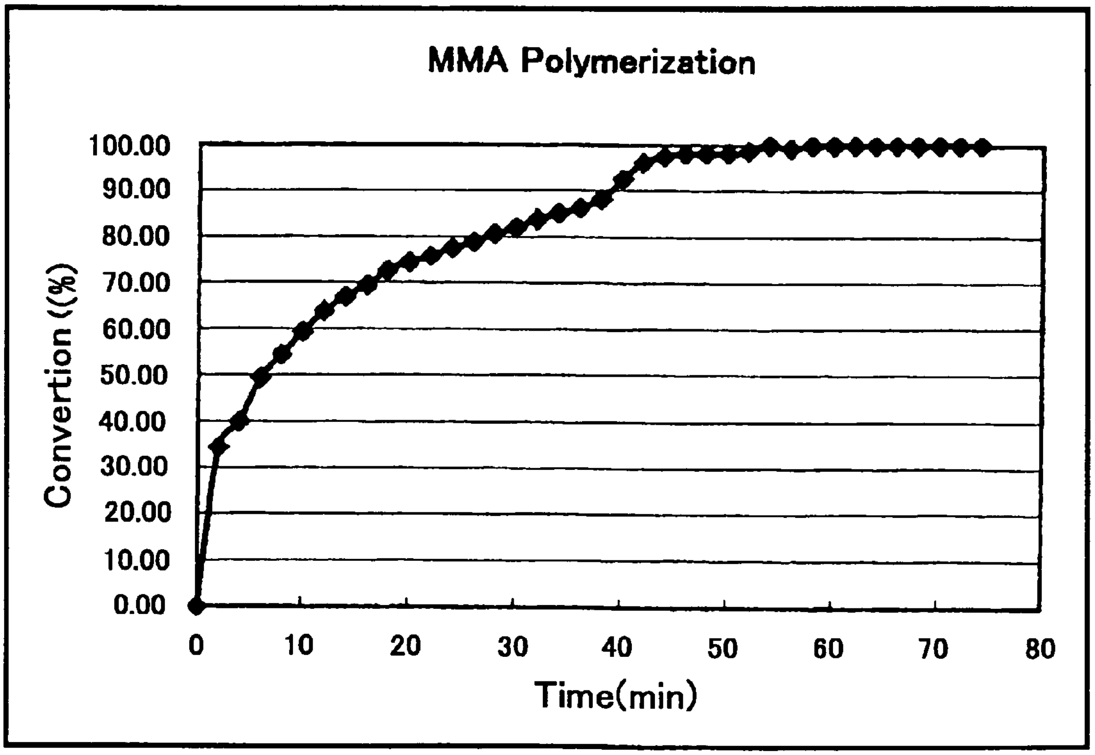
FIG. 30 is a graph showing the reactivity calculated from infrared absorption at 1459 $cm^{-1}$ in UV curing of MMA.

In succession, by turning on the power source of the ultraviolet ray irradiating device, multimeasurement was started at the same time by using the infrared ray. The result is shown in FIG. 28. As the UV curing reaction progressed, the absorption at 1459 $cm^{-1}$ was lost. Tracing the loss of absorption at 1459 $cm^{-1}$, the reaction behavior and reaction rate were measured. The results are shown in FIG. 29 and FIG. 30.

The present application claims priority under 35 U.S.C. § 119 to Japanese Patent Application No.2002-306057, filed Oct. 21, 2002, entitled "SAMPLE HOLDER FOR SPECTRUM MEASUREMENT AND SPECTROPHOTOMETER". The content of this application is incorporated herein by reference in its entirety.

What is claimed is:

1. A sample holder for spectrum measurement settable in a measuring chamber of a spectrophotometer and being used for measuring a spectrum of a liquid sample, said measuring chamber being provided in a way of an irradiation light being emitted from a light irradiating means (21) to a light detecting means (22) for spectrum measurement, which comprises a holding block (11) having a hole (111) and a light introducing path (112) being provided crosswise, said the hole (111) being for holding a sample container (30) filled with the liquid sample, said the light introducing path (112) being for introducing the irradiation light for spectrum measurement into the liquid sample held by said hole (111), said the irradiation light for spectrum measurement being emitted from the light irradiating means (21) toward the liquid sample held by the hole (111) by passing through the light introducing path (112) and reaching to the light detecting means (22) of the spectrophotometer, a light introducing path position adjusting means (12) being located under the holding block (11), said the light introducing path position adjusting means (12) comprising a light introducing path horizontal direction position adjusting means (12-1) and/or a light introducing path vertical direction position adjusting means (12-2), for adjusting so as to the irradiation light is introduced into the liquid sample by aligning a position of the light introducing path (112) with a propagating route of the irradiation light for spectrum measurement, when the sample holder for spectrum measurement is set in the measuring chamber of the spectrophotometer, said the light introducing path vertical direction position adjusting means (12-2) adjusting the position of the light introducing path (112) in a vertical direction relative to the propagating route of the irradiation light for spectrum measurement, said the holding block (11) further comprising a device for controlling a temperature of said liquid sample.

2. The sample holder for spectrum measurement according to claim 1, wherein the device for controlling a temperature of the liquid sample is a heating device (15) for heating the liquid sample.

3. The sample holder for spectrum measurement according to claim 1, wherein said the device for controlling a temperature of the liquid sample is an apparatus (51) for introducing and circulating a refrigerant (50) to the holding block (11) for keeping the liquid sample at a low temperature of 10° C. or less.

4. The sample holder for spectrum measurement according to claim 1, wherein a lower insulating means (13) is provided between the holding block (11) and the light introducing path position adjusting means (12).

5. The sample holder for spectrum measurement according to claim 4, which further comprises an insulating cover (14) outside of the holding block (11).

6. The sample holder for spectrum measurement according to claim 1, wherein said the light introducing path horizontal direction position adjusting means (12-1) adjusts a position in an X-direction and a Y-direction orthogonal to the X-direction, and wherein the light introducing path vertical direction position adjusting means (12-2) adjusts a position in a Z-direction perpendicular to the X-direction and the Y-direction, a plane which is parallel to the horizontal direction including the X-direction, and a plane which is parallel to the horizontal direction including the Y-direction being on the same plane or parallel.

7. The sample holder for spectrum measurement according to claim 6, wherein the light introducing path horizontal direction position adjusting means (12-1) comprises an X-direction operation unit and an X-direction fixing unit, as well as comprises a Y-direction operation unit and a Y-direction fixing unit, and wherein the light introducing path vertical direction position adjusting means (12-2) comprises a Z-direction operation unit and a Z-direction fixing unit.

8. The sample holder for spectrum measurement according to claim 1, wherein said the hole (111) is provided plurally, and wherein said the holding block (11) comprises a rotating means (80), said rotating means (80) being used for measuring spectra of two or more liquid samples serially, rotating said the holding block (11) around a center of the holding block (11) as an axis horizontally, and aligning a position of the light introducing path (112) to the propagating route of the irradiation light for spectrum measurement, and adjusting again.

9. The sample holder for spectrum measurement according to claim 8, wherein a lower insulating means (13) is provided between the holding block (11) and the light introducing path position adjusting means (12), and wherein the rotating means (80) comprises the lower insulating means (13) and the holding block (11) being fixed together, and rotates the holding block (11) and the lower insulating means (13) together horizontally on an upper plane of the light introducing path position adjusting means (12), said the lower insulating means (13) being provided to the light introducing path position adjusting means (12), by a bolt (66), so as the bolt (66) to be a center of the lower insulating means (13) as an axis.

10. The sample holder for spectrum measurement according to claim 8, wherein a lower insulating means (13) is provided between a lower part of the holding block (11) and the light introducing path position adjusting means (12), and wherein said rotating means (80) comprises the lower insulating means (13) and the light introducing path position adjusting means (12) being fixed together in a manner that a center axis of the lower insulating means (13) is penetrated by a bolt (66), and rotates the holding block (11) alone on an upper plane of the lower insulating means (13), the bolt (66) being embed to the holding block (11) and supporting the holding block (11).

11. The sample holder for spectrum measurement according to claim 8, wherein said holding block (11) is circular columnar or polygonal columnar in a shape.

12. The sample holder for spectrum measurement according to claim 11, wherein a lower part of the holding block having said the light introducing path (112), is formed by cutting out one or more sector columnar shape parts so as to form a sector columnar gap in the lower part of the holding block (11), so that a bottom of the hole (111) is still held at the lower part of the holding block (11), and also is still remained in the lower part of the holding block.

13. The sample holder for spectrum measurement according to claim 11, wherein a thin film holder component (86) is settable in a way of the propagating route of the irradiation light, passing through said the light introducing path (112) in said the holding block (11), so that the irradiation light for spectrum measurement transmits a film obtained by applying the liquid sample as a thin film.

14. The sample holder for spectrum measurement according to claim 12, wherein said the thin film holder component (86) is settable in the sector columnar gap formed in a way of the propagating route of the irradiation light passing through the light introducing path (112) in the holding block (11) at the lower part of the holding block (11), and is detachable and/or changeable with an angle relative to the propagating route of the irradiation light.

15. The sample holder for spectrum measurement according to claim 14, wherein a diamond cell or a KBr tablet is mounted in said thin film holder component, and wherein the angle of the thin film holder component relative to the propagating route of the irradiation light for spectrum measurement is changeable between 0 to 90 degrees.

16. The sample holder for spectrum measurement according to claim 1, wherein said the irradiation light for spectrum measurement being emitted from the light irradiating means (21) and reaching to the light detecting means (22) reaches to the light detecting means (22), by transmitting or scattering from the liquid sample after entering into the liquid sample.

17. The sample holder for spectrum measurement according to claim 16, wherein said the irradiation light for spectrum measurement is an infrared spectrum, wherein said the light irradiating means (21) and said the light detecting means (22) are disposed linearly and opposingly, and wherein said the irradiation light for spectrum measurement reaches to the light detecting means (22) by transmitting from the liquid sample after entering into the liquid sample.

18. The sample holder for spectrum measurement according to claim 16, wherein said the irradiation light for spectrum measurement is a Raman spectrum, and wherein said the irradiation light for spectrum measurement is introduced into the liquid sample and then a scattering light irradiated from the liquid sample is detected by the light detecting means (22).

19. The sample holder for spectrum measurement according to claim 18, wherein the scattering light is detected by using an optical sensor as the light detecting means (22) provided with the light irradiating means (21), or detected by the light detecting means (22) provided at an angle of 90 degrees direction relative to the irradiation light irradiated from the light irradiating means (21).

20. The sample holder for spectrum measurement according to claim 1, wherein the sample holder for spectrum measurement is externally provided with a irradiating means (6) of at least one species of ray or electron beam selected from a group consisting of electron beam, gamma-ray, laser beam, X-ray, ultraviolet ray, visible ray and far infrared ray in a position to be introduced the ray into the liquid sample, and further provided with a ray introducing path (116) for introducing the ray irradiated from the irradiating means (6) into the liquid sample other than the light introducing path (112), said the ray being other than the light for spectrum measurement, said the sample holder for spectrum measurement being used for measuring a state of the liquid sample changed by the ray irradiated from the irradiating means (6).

21. The sample holder for spectrum measurement according to claim 20, wherein said holding block (11) is circular columnar or polygonal columnar in a shape, and wherein a lower part of the holding block having the light introducing path (112), is formed by cutting out one or more sector columnar shape parts so as to form a sector columnar gap in the lower part of the holding block (11), so that a bottom of the hole (111) is still held at the lower part of the holding block (11), and also is still remained in the lower part of the holding block.

22. The sample holder for spectrum measurement according to claim 21, wherein a thin film holder component (86) is settable in the sector columnar gap formed in a way of the propagating route of the irradiation light which passes through said the light introducing path (112) in said the holding block (11), so that the irradiation light for spectrum measurement transmits a film obtained by applying the liquid sample as a thin film, and wherein the ray other than the light for spectrum measurement is introduced into the film applied on the thin film holder component from said irradiating means (6), said the thin film holder component (86) being detachable and/or changeable with an angle relative to the propagating route of the irradiation light.

23. The sample holder for spectrum measurement according to claim 22, wherein a diamond cell or a KBr tablet is mounted in the thin film holder component (86), and wherein an angle of the thin film holder component (86) relative to the propagating route of the irradiation light for spectrum measurement is changeable between 0 to 90 degrees.

24. The sample holder for spectrum measurement according to claim 20, wherein said irradiating means (6) is an ultraviolet ray irradiating means.

25. A spectrum measuring method which comprises setting the sample holder for spectrum measurement according to claim 1 in a spectrophotometer, adjusting the light introducing path (112) to the optical path by moving the light introducing path (112) in order to match light detecting sensitivity of the spectrophotometer by means of the light introducing path horizontal direction position adjusting means (12-1) and/or the light introducing path vertical direction position adjusting means (12-2), introducing the irradiation light for spectrum measurement into a liquid sample controlled with temperature, and measuring the spectrum of the liquid sample by detecting the irradiation light for spectrum measurement by means of the light detecting means (22), said the irradiation light for spectrum measurement being emitted from the light irradiating means (21) and reaching to the light detecting means (22) of the spectrophotometer.

26. A spectrum measuring method which comprises setting the sample holder for spectrum measurement according to claim 20 in a spectrophotometer, introducing the ray other than the light for spectrum measurement into a liquid sample from the irradiating means (6), adjusting the light introducing path (112) to the optical path by moving the light introducing path (112) in order to match light detecting sensitivity of the spectrophotometer by means of the light introducing path horizontal direction position adjusting means (12-1) and/or the light introducing path vertical direction position adjusting means (12-2), introducing the irradiation light for spectrum measurement into the liquid sample controlled with temperature, and measuring the spectrum of the liquid sample changed by the ray irradiated from the irradiating means (6), by detecting the irradiation light for spectrum measurement by means of the light detecting means (22), said the irradiation light for spectrum measurement being irradiated from the light irradiating means (21) and reaching to the light detecting means (22) of the spectrophotometer.

27. A spectrophotometer which comprises the sample holder for spectrum measurement according to claim 1.

28. A spectrophotometer which comprises the sample holder for spectrum measurement according to claim 20.

* * * * *